(12) United States Patent
Tidwell et al.

(10) Patent No.: US 6,413,938 B1
(45) Date of Patent: Jul. 2, 2002

(54) BENZIMIDAZOLE DERIVATIVES FOR THE TREATMENT OF VIRAL INFECTIONS

(75) Inventors: Jeffrey H. Tidwell, Raleigh; Stanley D. Chamberlain, Research Triangle Park; George A. Freeman, Research Triangle Park; Joseph H. Chan, Research Triangle Park; George W. Koszalka, Research Triangle Park, all of NC (US); Leroy B. Townsend; John C. Drach, both of Ann Arbor, MI (US)

(73) Assignees: The Regents of the University of Michigan, Ann Arbor, MI (US); Glaxo Wellcome Inc., Research Triangle Park, NC (US)

( * ) Notice: Subject to any disclaimer, the term of this patent is extended or adjusted under 35 U.S.C. 154(b) by 0 days.

(21) Appl. No.: 09/367,260

(22) PCT Filed: Feb. 13, 1998

(86) PCT No.: PCT/GB98/00448

§ 371 (c)(1),
(2), (4) Date: Aug. 25, 1999

(87) PCT Pub. No.: WO98/35977

PCT Pub. Date: Aug. 20, 1998

Related U.S. Application Data

(60) Provisional application No. 60/037,992, filed on Feb. 13, 1997.

(30) Foreign Application Priority Data

Feb. 14, 1997 (GB) .............................. 9703134

(51) Int. Cl.$^7$ ...................... A61K 31/70; A61K 31/415; C07H 19/04; C07D 235/04
(52) U.S. Cl. .................. 514/43; 514/394; 514/934; 536/24.1; 536/28.9; 548/304.7
(58) Field of Search ................. 514/43, 934, 394; 536/28.9, 24; 548/304.7

(56) References Cited

U.S. PATENT DOCUMENTS

| | | | |
|---|---|---|---|
| 3,399,987 A | 9/1968 | Woods et al. | 514/394 X |
| 3,555,040 A | 1/1971 | Frick et al. | 514/394 X |
| 3,655,901 A | 4/1972 | Jensen et al. | 424/273 |

(List continued on next page.)

FOREIGN PATENT DOCUMENTS

| | | |
|---|---|---|
| DE | A2 130 030 | 12/1972 |
| EP | 0 136 938 | 4/1985 |
| EP | A 0 304624 | 3/1989 |
| EP | 0 350 467 | 1/1990 |
| EP | 0 515 156 | 11/1992 |
| WO | WO A92 07867 | 5/1992 |
| WO | 92/18517 | 10/1992 |
| WO | 93/18009 | 9/1993 |
| WO | WO 94 08456 | 4/1994 |
| WO | 96/01833 | 1/1996 |
| WO | WO96/07646 | 3/1996 |
| WO | WO97/25316 | 7/1997 |
| WO | WO 97 25337 | 7/1997 |
| WO | WO97/27204 | 7/1997 |

OTHER PUBLICATIONS

Gosselin et al., "Synthesis and biological evaluation of new 5,6–dichlorobenzimidazole nucleoside derivatives," Antiviral Chem. Chemotherapy, vol. 5, pp. 243–256 (1994).

Revankar et al., The synthesis of 2–chloro–1–(β–D–ribofuranosyl)benzimidazole and certain related derivatives (1), J. Heterocycles, vol. 5, pp. 477–483 (1968).

Revankar et al., The synthesis of 2–chloro–1–β–D–ribofuranosyl–5,6–dimethylbenzimidazole and certain related derivative (1), J. Heterocycles, vol. 5, No. 4, pp. 615–620 (1968).

Gordon et al., "Kinetics of Decay in the Expression of Interferon–Dependent mRNAs Responsible for Resistance to Virus," Proc. Natl. Acad. Sci. USA, 77(1) pp. 452–456 (1980).

(List continued on next page.)

*Primary Examiner*—Floyd D. Higel
*Assistant Examiner*—Ebenezer Sackey
(74) *Attorney, Agent, or Firm*—Nixon & Vanderhye P.C.

(57) ABSTRACT

According to a first aspect of the invention there is provided compounds of formula (I):

(I)

wherein:

$R^1$ is hydroxy; O-acetyl; or a halo atom;

$R^2$ is hydroxy; O-acetyl; or a halo atom;

$R^3$ is hydrogen; a halo atom; azido; $C_{2-6}$alkenyl; $C_{2-6}$alkynyl; $C_{6-14}$aryl $C_{2-6}$alkenyl; $C_{6-14}$aryl$C_{2-6}$alkynyl —$NR^8R^9$ (where $R^8$ and $R^9$ may be the same or different and are hydrogen, $C_{1-8}$alkyl, cyano$C_{1-8}$alkyl, hydroxy$C_{1-8}$alkyl, halo$C_{1-8}$alkyl, $C_{3-7}$cycloalkyl, $C_{1-8}$alkyl$C_{3-7}$cycloalkyl, $C_{2-6}$alkenyl, $C_{3-7}$cycloalkyl$C_{1-8}$alkyl, $C_{2-6}$alkynyl, $C_{6-14}$aryl, $C_{6-14}$aryl$C_{1-8}$alkyl, heterocycle$C_{1-8}$alkyl, $C_{1-8}$alkylcarbonyl, $C_{6-14}$arylsulfonyl, $C_{1-8}$alkysulfonyl, or $R^8R^9$ together with the N atom to which they are attached form a 3,4,5 or 6 membered heterocyclic ring); —$OR^{10}$ (where $R^{10}$ is hydrogen, $C_{1-8}$alkyl, $C_{6-14}$aryl, or $C_{6-14}$aryl$C_{1-8}$alkyl, $C_{2-6}$alkenyl, $C_{2-6}$alkynyl, $C_{6-14}$aryl $C_{2-6}$alkenyl or $C_{6-14}$aryl$C_{2-6}$alkynyl); or —$SR^{11}$ (where $R^{11}$ is hydrogen, $C_{1-8}$alkyl, $C_{6-14}$aryl, or $C_{6-14}$aryl$C_{1-8}$alkyl).

10 Claims, No Drawings

U.S. PATENT DOCUMENTS

| | | | |
|---|---|---|---|
| 4,002,623 A | 1/1977 | Kadin | 424/248 X |
| 5,248,672 A | 9/1993 | Townsend et al. | 514/43 |
| 5,360,795 A | 11/1994 | Townsend et al. | 514/43 |
| 5,399,580 A | 3/1995 | Daluge | 514/394 |
| 5,473,063 A | 12/1995 | Classon et al. | 536/122 |
| 5,534,535 A | 7/1996 | Townsend et al. | 514/394 |
| 5,574,058 A | 11/1996 | Townsend et al. | 514/394 |
| 5,646,125 A | 7/1997 | Townsend et al. | 514/43 |
| 5,654,283 A | 8/1997 | Townsend et al. | 514/43 |
| 5,665,709 A | 9/1997 | Townsend et al. | 514/43 |
| 5,705,490 A | 1/1998 | Townsend et al. | 514/43 |
| 5,712,255 A | 1/1998 | Townsend et al. | 514/43 |
| 5,874,413 A | 2/1999 | Townsend et al. | 514/43 |

OTHER PUBLICATIONS

Devivar et al., "Benzimidazole Ribonucleosides: Observation of an Unexpected Nitration When Performing Non–Aqueous Diazotizations with t–butyl Nitrite," Biorganic Et Medicinal Chem. Letters, 2(9), pp. 1105–1110 (Sep. 1992).

Tigges et a., "Human CD8+ Herpes Simplex Virus–Specific Cytotoxic T–Lymphocyte Clones Recognize Diverse Viron Protein Antigens," J. Virology, 66(3), pp. 1622–1634 (1992).

Devivar et al., "Benzimidazole Ribonucleosides: Design, Synthesis, and Antiviral Activity of Certain 2–(Alkylthio)– and 2–(Benzylthio)–5,6–dichloro–1–(β–D–ribofuranosyl) benzimidazoles," J. Med. Chem. 37(18), pp. 2942–2949 (Sep. 1994).

Townsend et al., "Design, Synthesis and Antiviral Activity of Certain 2,5,6–Trihalo–1–(β–D–ribofuranosyl)benzimidazoles," J. Med. Chem. 38(20), pp. 4098–4105 (Sep. 1995).

Yankulov et al., "The Transcriptional Elongation Inhibitor 5,6–Dichloro–1–β–D–ribofuranosylbenzimidazole Inhibits Translation Factor IIH–Associated Protein Kinase," J. Biol. Chem., 270(41), pp. 23922–23925 (Oct. 1995).

Nassiri et al., "Comparison of Benzimidazole Nucleosides and Ganciclovir on the In Vitro Proliferation and Colony Formation of Human Bone Marrow Progenitor Cells," British J. Haematology, 93(2), pp. 273–279 (May 1996).

Gundmundsson et al., "Synthesis and Antiviral Activity of Certain 5'–Modified Analogs of 2,5,6–Trichloro–1– (β–D–ribofuranosyl)benzimidazole," J. Med. Chem. 40(5), pp. 785–793 (Feb. 1997).

Zou et al., "Design, Synthesis, and Antiviral Evaluation of 2–Chloro–5, 6–dihalo–1–(β–D–ribofuranosyl)benzimidazoles as Potential Agents for Human Cytomegalovirus Infections," J. Med. Chem. 40(5), pp. 811–818 (Feb. 1997).

Physician's Desk Reference, 52nd Ed., Arky and Sifton (eds.), Medical Economics Co., Montvale, NJ, 1998, pp. 2452–2454 (see "Cytovene").

The Merck Index, 11th Ed., Budavari et al., (eds.) Merck Et Co., Rahway, NJ, 1989, p. 682.

Methods of Nucleoside Synthesis. Vorbrueggen, Helmut. Res. Lab., Schering A.–G., Berlin, D–1000/65, Fed. Rep. Ger. NATO Adv. Study Inst. Ser., Ser. A (1979), A26(Nucleoside Analogues: Chem., Biol., Med. Appl.), 35–69.

Vorbrüggen et al., "Nucleoside Synthesis with Trimethylsilyl Triflate and Perchlorate as Catalysts," Chem. Ber. 114, pp. 1234–1255 (1981).

Vorbrüggen et al., "New Catalysts for the Synthesis of Nucleosides," Angew. Chem. Internat. Edit. 14(6), pp. 421–422 (1974).

F. Meggio et al., European Journal of Biochemistry, vol. 187, No 1, Jan. 1990, pp. 89–94, "Ribofuranosyl–benzimidazole derivatives as inhibitors of casein kinase–2 and casein kinase–1".

M. Olivanen et al., Nucleosides Et Nucleotides, vol. 8, No. 1, 1989, pp. 133–144, "Mechanism for acid–catalyzed hydrolysis of nucleoside and acylonucleoside analogues of benzimidazole".

Bucknall, R.A., Journal Gen. Virology, vol. 1, 1967, pp. 89–99, "The effect s of substituted benzimidazoles on the growth of viruses and the nucleic acid metabolism of host cells".

Dobrowolska G. et al., Biochimica Et Biophysica ACTA, vol. 1080, No. 3, Nov. 15, 1991, pp. 221–226, "Benzimidazole Nucleoside Analogues As Inhibitors of Plant (Maze Seedling) Casein Kinases".

F. Seela et al., Helvetica Chimica ACTA, vol. 79, Mar. 20, 1996, pp. 488–498, "Synthesis of 4–substituted 1H–benzimidazole 2'–deoxyribonucleosides and utility of the 4–nitro compound as universal base".

Dawson, W.O. Et C. Boyd, "Phytopathology", vol. 77, No. 3, 1987, pp. 477–480, "Modifictions of nucleic acid precursors that inhibit plant virus modification".

BENZIMIDAZOLE DERIVATIVES FOR THE TREATMENT OF VIRAL INFECTIONS

This application is a 371 of PCT/GB98/00448, filed Feb. 13, 1998. This application claims the benefit of U.S. provisional Application No. 60/037,992, filed Feb. 13, 1997.

FIELD OF THE INVENTION

The present invention relates to certain benzimidazole derivatives and their use in medical therapy particularly for the treatment or prophylaxis of virus infections such as those caused by herpes viruses. The invention also relates to the preparation of the benzimidazole derivatives and pharmaceutical formulations containing them.

BACKGROUND OF THE INVENTION

Of the DNA viruses, those of the herpes group are the source of the most common viral illnesses in man. The group includes herpes simplex virus types 1 and 2 (HSV), varicella zoster virus (VZV), cytomegalovirus (CMV), Epstein-Barr virus (EBV), human herpes virus type 6 (HHV-6) and human herpes virus type 7 (HHV-7). HSV-1 and HSV-2 are some of the most common infectious agents of man. Most of these viruses are able to persist in the host's neural cells; once infected, individuals are at risk of recurrent clinical manifestations of infection which can be both physically and psychologically distressing.

HSV infection is often characterized by extensive and debilitating lesions of the skin, mouth and/or genitals. Primary infections may be subclinical although tend to be more severe than infections in individuals previously exposed to the virus. Ocular infection by HSV can lead to keratitis or cataracts thereby endangering the host's sight. Infection in the new-born, in immunocompromised patients or penetration of the infection into the central nervous system can prove fatal. VZV is a herpes virus which causes chickenpox and shingles. Chickenpox is the primary disease produced in a host without immunity, and in young children is usually a mild illness characterized by a vesicular rash and fever. Shingles or zoster is the recurrent form of the disease which occurs in adults who were previously infected with VZV. The clinical manifestations of shingles are characterized by neuralgia and a vesicular skin rash that is unilateral and dermatomal in distribution. Spread of inflammation may lead to paralysis or convulsions. Coma can occur if the meninges become affected. VZV is of serious concern in patients receiving immunosuppressive drugs for transplant purposes or for treatment of malignant neoplasia and is a serious complication of AIDS patients due to their impaired immune system.

In common with other herpes viruses, infection with CMV leads to a lifelong association of virus and host. Congenital HCMV disease is characterized by jaundice, hepatosplenomegaly, petechial rash and multiple organ dysfunction and is associated with long-term sequelae such as hearing loss and mental deficiency. Infection can result in retinitis leading to blindness or, in less severe forms, failure to thrive, and susceptibility to chest and ear infections. CMV infection in patients whose immune systems are immature or who are immunocompromised for example as a result of malignancy, treatment with immunosuppressive drugs following transplantation or infection with Human Immunodeficiency Virus, may give rise to retinitis, colitis, esophagistis, hepatitis, meningoencephalitis, pneumonitis, gastrointestinal disorders and neurological diseases. In addition, these CMV disease syndromes can affect patients who are not immunocompromised.

The main disease caused by EBV is acute or chronic infectious mononucleosis (glandular fever). Examples of other EBV or EBV associated diseases include lymphoproliferative disease which frequently occurs in persons with congenital or acquired cellular immune deficiency, X-linked lymphoproliferative disease which occurs namely in young boys, EBV-associated B-cell tumors, Hodgkin's disease, nasopharyngeal carcinoma, Burkitt lymphoma, non-Hodgkin B-cell lymphoma, thymomas and oral hairy leukoplakia. EBV infections have also been found in association with a variety of epithelial-cell-derived tumors of the upper and lower respiratory tracts including the lung.

HHV-6 has been shown to be a causative agent of infantum subitum in children and of kidney rejection and interstitial pneumonia in kidney and bone marrow transplant patients, respectively, and may be associated with other diseases such as multiple sclerosis. There is also evidence of repression of stem cell counts in bone marrow transplant patients. HHV-7 is of undetermined disease etiology.

Hepatitis B virus (HBV) is a viral pathogen of world-wide major importance. The virus is etiologically associated with primary hepatocellular carcinoma and is thought to cause 80% of the world's liver cancer. Clinical effects of infection with HBV range from headache, fever, malaise, nausea, vomiting, anorexia and abdominal pains. Replication of the virus is usually controlled by the immune response, with a course of recovery lasting weeks or months in humans, but infection may be more severe leading to persistent chronic liver disease outlined above.

WO 92/07867 describes certain polysubstituted benzimidazole derivatives and their activity against HSV and CMV. U.S. Pat. Nos. 5,399,580 and 5,534,535 disclose antiviral nucleoside analogues containing a substituted benzimidazole base attached to a carbocyclic ring in place of the conventional sugar residue. U.S. Pat. No. 5,360,795 describes 2,5,6,-trichloro-1-(β-D-5-deoxyribofuranosyl) benzimidazole and 2-bromo-5,6-dichloro-1-(β-D 5-deoxyribofuranosyl)benzimidazole and their activity against HSV and CMV.

DETAILED DESCRIPTION OF THE INVENTION

It has now been discovered that certain 5'-deoxy polysubstituted benzimidazole analogues are useful for the treatment or prophylaxis of viral infections.

According to a first aspect of the invention there is provided compounds of formula (I):

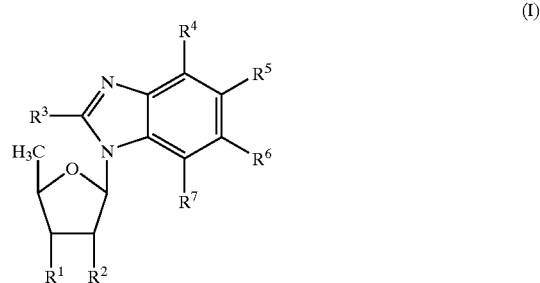

wherein:

$R^1$ is hydroxy; O-acetyl; or a halo atom;

$R^2$ is hydroxy; O-acetyl; or a halo atom;

$R^3$ is hydrogen; a halo atom; azido; $C_{2-6}$alkenyl; $C_{2-6}$alkynyl; $C_{6-14}$aryl $C_{2-6}$alkenyl; $C_{6-14}$aryl$C_{2-}$ ₆alkynyl —NR⁸R⁹ (where R⁸ and R⁹ may be the same or different and are hydrogen, $C_{1-8}$alkyl, cyano$C_{1-8}$alkyl, hydroxy$C_{1-8}$alkyl, halo$C_{1-8}$alkyl, $C_{3-7}$cycloalkyl, $C_{1-8}$alkyl$C_{3-7}$cycloalkyl, $C_{2-6}$alkenyl, $C_{3-7}$cycloalkyl$C_{1-8}$alkyl, $C_{2-6}$alkynyl, $C_{6-14}$aryl, $C_{6-14}$aryl$C_{1-8}$alkyl, heterocycle$C_{1-8}$alkyl, $C_{1-8}$alkylcarbonyl, $C_{6-14}$arylsulfonyl, $C_{1-8}$alkylsulfonyl, or R⁸R⁹ together with the N atom to which they are attached form a 3,4,5 or 6 membered heterocyclic ring); —OR¹⁰ (where R¹⁰ is hydrogen, $C_{1-8}$alkyl, $C_{6-14}$aryl, or $C_{6-14}$aryl$C_{1-8}$alkyl, $C_{2-6}$alkenyl, $C_{2-6}$alkynyl, $C_{6-14}$aryl $C_{2-6}$alkenyl or $C_{6-14}$aryl$C_{2-6}$alkynyl); or —SR¹¹ (where R¹¹ is hydrogen, $C_{1-8}$alkyl, $C_{6-14}$aryl, or $C_{6-14}$aryl$C_{1-8}$alkyl);

R⁴, R⁵, R⁶, and R⁷, which may be the same or different, are each independently selected from hydrogen; a halo atom; cyano; nitro; $C_{6-14}$aryl; $C_{6-14}$aryl$C_{1-8}$alkyl; —NR⁸R⁹ (where R⁸ and R⁹ may be the same or different and are hydrogen, $C_{1-8}$alkyl, cyano$C_{1-8}$alkyl, hydroxy$C_{1-8}$alkyl, halo$C_{1-8}$alkyl, $C_{3-7}$cycloalkyl, $C_{1-8}$alkyl$C_{3-7}$cycloalkyl, $C_{2-6}$alkenyl, $C_{3-7}$cycloalkyl$C_{1-8}$alkyl, $C_{2-6}$alkynyl, $C_{6-14}$aryl, $C_{6-14}$aryl$C_{1-8}$alkyl, heterocycle$C_{1-8}$alkyl, $C_{1-8}$alkylcarbonyl, —$C_{6-14}$arylsulfonyl, $C_{1-8}$alkylsulfonyl, or R⁸R⁹ together with the N atom to which they are attached form a 3,4,5 or 6 membered heterocyclic ring); —OR¹⁰ (where R¹⁰ is hydrogen, $C_{1-8}$alkyl, $C_{6-14}$aryl, $C_{6-14}$aryl$C_{1-8}$alkyl, $C_{2-6}$alkenyl, $C_{2-6}$alkynyl, $C_{6-14}$aryl $C_{2-6}$alkenyl or $C_{6-14}$aryl$C_{2-6}$alkynyl); —SR¹² (where R¹² is hydrogen, $C_{1-8}$alkyl, $C_{6-14}$aryl, or $C_{6-14}$aryl$C_{1-8}$alkyl); trifluoromethyl; —S(O)₂R¹³ (where R¹³ is hydrogen, $C_{1-8}$alkyl, $C_{6-14}$aryl, or $C_{6-14}$aryl$C_{1-8}$alkyl); C(O)NR¹⁴R¹⁵ (where R¹⁴ and R¹⁵ may be the same or different and are hydrogen, $C_{1-8}$alkyl, $C_{6-14}$aryl, or $C_{6-14}$aryl$C_{1-8}$alkyl); heterocycle or heterocycle$C_{1-8}$alkyl;

provided that when R⁵ and R⁶ are Cl, R⁴ and R⁷ are hydrogen and R³ is Cl or Br; then R¹ and R² are not hydroxy or O-acetyl;

or a pharmaceutically acceptable derivative thereof.

Preferred compounds of formula (I) are the beta anomers of compounds of formula (I).

In a further aspect of the invention there is provided compounds of formula (Ia)

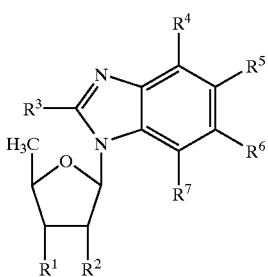

(Ia)

wherein:
R¹ is hydroxy or O-acetyl;
R² is hydroxy, O-acetyl, or a fluorine atom;
R³ is a halo atom or —NR⁸R⁹ (wherein R⁸ and R⁹ are as hereinbefore defined).
R⁴ is hydrogen, a halo atom, nitrile, trifluoromethyl, or nitro;
R⁵ and R⁶ may be the same or different and are hydrogen, a halo atom, nitrile, trifluoromethyl, nitro, or —SR¹² (wherein R¹² is as hereinbefore defined);
R⁷ is hydrogen or a halo atom;
provided that when R⁵ and R⁶ are Cl, R⁴ and R⁷ are hydrogen and R³ is Cl or Br; then R¹ and R² are not hydroxy or O-acetyl;
or a pharmaceutically acceptable derivative thereof.

Preferred compounds of formula (Ia) are the beta anomers of compounds of formula (Ia).

In a further aspect of the invention there is provided compounds of formula (Ib):

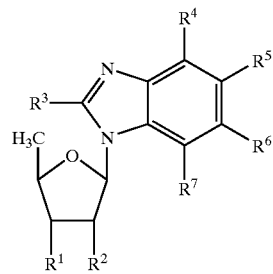

(Ib)

wherein:
R¹ is hydroxy or O-acetyl;
R² is hydroxy, O-acetyl, or a fluorine atom;
R³ is a halo atom, or —NR⁸R⁹, wherein R⁸ is hydrogen and R⁹ is a $C_{1-6}$ alkyl, or $C_{3-7}$cycloalkyl;
R⁴ is hydrogen or a halo atom;
R⁵ and R⁶ may be the same or different and are hydrogen, a halo atom, nitro, nitrile, trifluoromethyl or —SR¹² wherein R¹² is $C_{1-6}$alkyl;
R⁷ is hydrogen or fluorine;
provided that when R⁵ and R⁶ are Cl, R⁴ and R⁷ are hydrogen and R³ is Cl or Br; then R¹ and R² are not hydroxy or O-acetyl;
or a pharmaceutically acceptable derivative thereof.

Preferred compounds of formula (Ib) are the beta anomers of compounds of formula (Ib).

In a further aspect of the invention, there is provided compounds of formula (Ic)

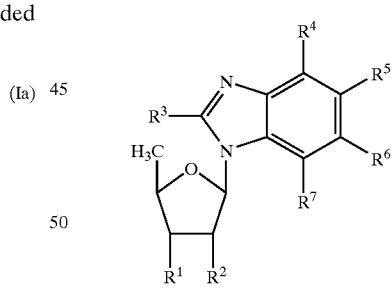

(Ic)

wherein:
R¹ is hydroxy;
R² is hydroxy, or a fluorine atom;
R³ is a halo atom, or —NR⁸R⁹, wherein R⁸ is hydrogen and R⁹ is a $C_{1-6}$ alkyl, or $C_{3-7}$cycloalkyl;
R⁴ is hydrogen or a halo atom;
R⁵ and R⁶ may be the same or different and are hydrogen, a halo atom, nitro, nitrite, trifluoromethyl, CH₃, or —SR¹² wherein R¹² is $C_{1-6}$alkyl;
R⁷ is hydrogen or fluorine;
provided that when R⁵ and R⁶ are Cl, R⁴ and R⁷ are hydrogen and R³ is Cl or Br, then R¹ and R² are not hydroxy or O-acetyl;

or a pharmaceutically acceptable derivative thereof.

Preferred compounds of formula (Ic) are the beta anomers of compounds of formula (Ic).

In a further aspect of the invention there is provided compounds of formula (Id):

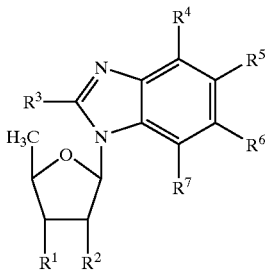

(Id)

$R^1$ is hydroxy;
$R^2$ is hydroxy, or a fluorine atom;
$R^3$ is a halo atom, or —$NR^8R^9$, wherein $R^8$ is hydrogen and $R^9$ is a $C_{1-6}$ alkyl, or $C_{3-7}$cycloalkyl;
$R^4$ is hydrogen or a halo atom;
$R^5$ and $R^6$ may be the same or different and are hydrogen, a halo atom, nitro, nitrile, trifluoromethyl, $CH_3$, or —$SR^{12}$ wherein $R^{12}$ is $C_{1-6}$alkyl;
$R^7$ is hydrogen or fluorine;
provided that $R^1$ and $R^2$ are cis to each other; and further provided that when $R^5$ and $R^6$ are Cl, $R^4$ and $R^7$ are hydrogen and $R^3$ is Cl or Br; then $R^1$ and $R^2$ are not hydroxy or O-acetyl;
or a pharmaceutically acceptable derivative thereof.

Preferred compounds of formula (Id) are the beta anomers of compounds of formula (Id).

In a further aspect of the present invention there is provided compounds of formula (Ie)

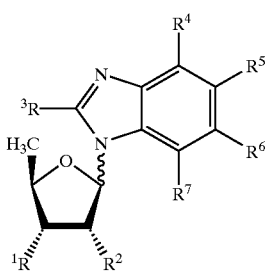

(Ie)

wherein:
$R^1$ is hydroxy; O-acetyl; or a halo atom;
$R^2$ is hydroxy; O-acetyl; or a halo atom;
$R^3$ is hydrogen; a halo atom; azido; $C_{2-6}$alkenyl; $C_{2-6}$alkynyl; aryl $C_{2-6}$alkenyl; $C_{6-14}$aryl $C_{2-6}$alkynyl; —$NR^8R^9$ (where $R^8$ and $R^9$ may be the same or different and are hydrogen, $C_{1-8}$alkyl, cyano$C_{1-8}$alkyl, hydroxy$C_{1-8}$alkyl, halo$C_{1-8}$alkyl, $C_{3-7}$cycloalkyl, $C_{1-8}$alkyl$C_{3-7}$cycloalkyl, $C_{2-6}$alkenyl, $C_{3-7}$cycloalkyl$C_{1-8}$alkyl, $C_{2-6}$alkynyl, $C_{6-14}$aryl, $C_{6-14}$aryl$C_{1-8}$alkyl, heterocycleC$_{1-8}$alkyl, $C_{1-8}$alkylcarbonyl, $C_{6-14}$arylsulfonyl, $C_{1-8}$alkylsulfonyl, or $R^8R^9$ together with the N atom to which they are attached form a 3,4,5 or 6 membered heterocyclic ring); —$OR^{10}$ (where $R^{10}$ is hydrogen, $C_{1-8}$alkyl, $C_{6-14}$aryl, or $C_{6-14}$aryl$C_{1-8}$alkyl, $C_{2-6}$alkenyl, $C_{2-6}$alkynyl, $C_{6-14}$aryl $C_{2-6}$alkenyl or $C_{6-14}$aryl $C_{2-6}$alkynyl); or —$SR^{11}$ (where $R^{11}$ is hydrogen, $C_{1-8}$alkyl, $C_{6-14}$aryl, or $C_{6-14}$aryl$C_{1-8}$alkyl);

$R^4$, $R^5$, $R^6$, and $R^7$, which may be the same or different, are each independently selected from hydrogen; a halo atom; cyano; nitro; $C_{6-14}$aryl; $C_{6-14}$aryl$C_{1-8}$alkyl; —$NR^8R^9$ (where $R^8$ and $R^9$ may be the same or different and are hydrogen, $C_{1-8}$alkyl, cyano$C_{1-8}$alkyl, hydroxy$C_{1-8}$alkyl, halo$C_{1-8}$alkyl, $C_{3-7}$cycloalkyl, $C_{1-8}$alkyl$C_{3-7}$cycloalkyl, $C_{2-6}$alkenyl, $C_{3-7}$cycloalkyl$C_{1-8}$alkyl, $C_{2-6}$alkynyl, $C_{6-14}$aryl, $C_{6-14}$aryl$C_{1-8}$alkyl, heterocycleC$_{1-8}$alkyl, $C_{1-8}$alkylcarbonyl, $C_{6-14}$arylsulfonyl, $C_{1-8}$alkylsulfonyl, or $R^8R^9$ together with the N atom to which they are attached form a 3,4,5 or 6 membered heterocyclic ring); —$OR^{10}$ (where $R^{10}$ is hydrogen, $C_{1-8}$alkyl, $C_{6-14}$aryl, $C_{6-14}$aryl$C_{1-8}$alkyl, $C_{2-6}$alkenyl, $C_{2-6}$alkynyl, $C_{6-14}$aryl $C_{2-6}$alkenyl or $C_{6-14}$aryl$C_{2-6}$alkynyl); —$SR^{12}$ (where $R^{12}$ is hydrogen, $C_{1-8}$alkyl, $C_{6-14}$aryl, or $C_{6-14}$aryl$C_{1-8}$ alkyl); trifluoromethyl; —$S(O)_2R^{13}$ (where $R^{13}$ is hydrogen, $C_{1-8}$alkyl, $C_{6-14}$aryl, or $C_{6-14}$aryl$C_{1-8}$alkyl); $C(O)NR^{14}R^{15}$ (where $R^{14}$ and $R^{15}$ may be the same or different and are hydrogen, $C_{1-8}$alkyl, $C_{6-14}$aryl, or $C_{6-14}$aryl$C_{1-8}$alkyl); heterocycle; or heterocycle $C_{1-8}$alkyl.
provided that when $R^5$ and $R^6$ are Cl, $R^4$ and $R^7$ are H and $R^3$ is Cl or Br; then $R^1$ and $R^2$ are not hydroxy or O-acetyl;
or a pharmaceutically acceptable derivative thereof.

The compounds of formula (I) including compounds of formula (Ia), (Ib), and (Ic), (Id), and Ie) above and their pharmaceutically acceptable derivatives are hereinafter referred to as the compounds according to the invention.

The compounds according to the invention contain one or more asymmetric carbon atoms and thus occur as racemates and racemic mixtures, single enantiomers, diastereomeric mixtures and individual diastereomers, and regioisomers. All such isomeric forms of these compounds are expressly included in the present invention. Each stereogenic carbon may be of the R or S configuration. Although the specific compounds exemplified in this application may be depicted in a particular stereochemical configuration, compounds having either the opposite stereochemistry at any given chiral center or mixtures thereof are also envisioned.

The present invention includes within its scope each possible alpha and beta anomer of the compounds of formula (I) and their physiologically functional derivatives, substantially free of the other anomer, that is to say no more than about 5% w/w of the other anomer. Compounds of formula (I) in the beta ribofuranosyl anomeric form are preferred.

Preferred compounds according to the invention include:
5,6-Dichloro-1-(5-deoxy-beta-D-ribofuranosyl)-N-(cyclopropyl)-1H-benzimidazol-2-amine;
5,6-Dichloro-1-(5-deoxy-beta-D-ribofuranosyl)-N-(1-methylethyl)-1H-benzimidazol-2-amine;
2-Azetidino-5,6-dichloro-1-(5-deoxy-beta-D-ribofuranosyl)1H-benzimidazole;
5,6-Dichloro-1-(5-deoxy-beta-D-ribofuranosyl)-N-(cyclopentyl)-1H-benzimidazol-2-amine;
5,6-Dichloro-1-(5-deoxy-beta-D-ribofuranosyl)-O-(isopropyl)-1H-benzimidazol-2-one;
5,6-Dichloro-1-(5-deoxy-beta-D-ribofuranosyl)-N-(n-hexyl)-1H-benzimidazol-2-amine;
5,6-Dichloro-1-(5-deoxy-beta-D-ribofuranosyl)-N-((R)-sec-butyl)-1H-benzimidazol-2-amine;
5,6-Dichloro-1-(5-deoxy-beta-D-ribofuranosyl)-N-((S)-sec-butyl)-1H-benzimidazol-2-amine;

6-Trifluoromethyl-1-(5-deoxy-beta-D-ribofuranosyl)-N-(1-methylethyl)-1H-benzimidazol-2-amine;
2-Bromo-6-trifluoromethyl-1-(5-deoxy-beta-D-ribofuranosyl)-1H-benzimidazole;
5-Nitro-1-(5-deoxy-beta-D-ribofuranosyl)-N-(1-methylethyl)-1H-benzimidazol-2-amine;
6-Nitro-1-(5-deoxy-beta-D-ribofuranosyl)-N-(1-methylethyl)-1H-benzimidazol-2-amine;
5-Chloro-6-trifluoromethyl-1-(5-deoxy-beta-D-ribofuranosyl)-N-(1-methylethyl)-1H-benzimidazol-2-amine;
6-Chloro-5-trifluoromethyl-1-(5-deoxy-beta-D-ribofuranosyl)-N-(1-methylethyl)-1H-benzimidazol-2-amine;
2-Bromo-6-chloro-1-(5-deoxy-beta-D-ribofuranosyl)-1H-benzimidazole;
2-Bromo-5-chloro-1-(5-deoxy-beta-D-ribofuranosyl)-1H-benzimidazole;
6-Chloro-4,5-difluoro-1-(5-deoxy-beta-D-ribofuranosyl)-N-(1-methylethyl)-1H-benzimidazol-2-amine;
4,5,6-Trifluoro-1-(5-deoxy-beta-D-ribofuranosyl)-N-(1-methylethyl)1H-benzimidazol-2-amine;
5-Chloro-6-methylthio-1-(5-deoxy-beta-D-ribofuranosyl)-N-(1-methylethyl)-1H-benzimidazol-2-amine;
5,6,-Dichloro-4-fluoro-1-(5-deoxy-beta-D-ribofuranosyl)-N-(1-methylethyl)-1H-benzimidazol-2-amine;
5,6-Dichloro-7-fluoro-1-(5-deoxy-beta-D-ribofuranosyl)-N-(1-methylethyl)-1H-benzimidazol-2-amine; and
2,5,6-Trichloro-1-(5deoxy-α-D-lyxofuranosyl) benzimidazole.

The term "hydroxy", alone or in combination with any other term, refers to monohydroxylated or polyhydroxylated substituents.

The term "alkyl", alone or in combination with any other term, refers to a straight-chain or branch-chain saturated aliphatic hydrocarbon radical containing the specified number of carbon atoms, or where no number is specified, preferably from 1–10 and more preferably from 1–6 carbon atoms, optionally substituted with one or more substituents selected from C1-6 alkoxy, (for example methoxy), nitro, halogen, (for example chloro), amino, carboxylate and hydroxy. Examples of alkyl radicals include, but are not limited to, methyl, ethyl, n-propyl, isopropyl, n-butyl, isobutyl, sec-butyl, tert-butyl, pentyl, isoamyl, n-hexyl and the like.

The term "alkenyl, " alone or in combination with any other term, refers to a straight-chain or branched-chain mono- or poly-unsaturated aliphatic hydrocarbon radical containing the specified number of carbon atoms, or where no number is specified, preferably from 2–10 carbon atoms and more preferably, from 2–6 carbon atoms. References to alkenyl groups include groups which may be in the E- or Z-form or a mixture thereof and which when they contain at least three carbon atoms, may be branched. Examples of alkenyl radicals include, but are not limited to, ethenyl, E- and Z-propenyl, isopropenyl, E- and Z-butenyl, E- and Z-isobutyenyl, E- and Z-pentenyl, E- and Z-hexenyl, E,E-, E,Z-, Z, E- and Z,Z-hexadienyl and the like.

The term "alkynyl" refers to hydrocarbon groups of either a straight or branched configuration with one or more carbon-carbon triple bonds which may occur in any stable point along the chain, such as ethynyl, propynyl, butynyl, pentynyl, and the like.

The term "alkoxy" refers to an alkyl ether radical, wherein the term "alkyl" is defined above. Examples of suitable alkyl ether radicals include, but are not limited to, methoxy, ethoxy, n-propoxy, isopropoxy, n-butoxy, isobutoxy, sec-butoxy, tert-butoxy and the like.

Alkenyl and alkynyl substituents may optionally contain one or more heteroatoms such as nitrogen, sulfur, or oxygen.

The term "aryl, " alone or in combination with any other term, refers to a carbocyclic aromatic radical (such as phenyl or naphthyl) containing the specified number of carbon atoms, preferably from 6–14 carbon atoms, and more preferably from 6–10 carbon atoms, optionally substituted with one or more substituents selected from C1-6 alkoxy, (for example methoxy), nitro, halogen, (for example chloro), amino, carboxylate and hydroxy. Examples of aryl radicals include, but are not limited to phenyl, naphthyl, indenyl, indanyl, azulenyl, fluorenyl, anthracenyl and the like.

The term "heterocycle" and "heterocyclyl" radical, unless otherwise defined herein, refers to a stable 3–7 membered monocyclic heterocyclcic ring or 8–11 membered bicyclic heterocycicic ring which is either saturated or unsaturated, and which may be optionally benzofused if monocyclic. Each heterocycle consists of one or more carbon atoms and from one to four heteroatoms selected from the group consisting of nitrogen, oxygen and sulfur. As used herein, the terms "nitrogen and sulfur heteroatoms" include any oxidized form of nitrogen and sulfur, and the quaternized form of any basic nitrogen. A heterocyclyl radical may be attached at any endocyclic carbon or heteroatom which results in the creation of a stable structure. Preferred heterocycles include 5–7 membered monocyclic heterocycles and 8–10 membered bicyclic heterocycles. Examples of such groups include imidazolyl, imidazolinoyl, imidazolidinyl, quinolyl, isoqinolyl, indolyl, indazolyl, indazolinolyl, perhydropyridazyl, pyridazyl, pyridyl, pyrrolyl, pyrrolinyl, pyrrolidinyl, pyrazolyl, pyrazinyl, quinoxolyl, piperidinyl, pyranyl, pyrazolinyl, piperazinyl, pyrimidinyl, pyridazinyl, morpholinyl, thiamorpholinyl, furyl, thienyl, triazolyl, thiazolyl, carbolinyl, tetrazolyl, thiazolidinyl, benzofuranoyl, thiamorpholinyl sulfone, oxazolyl, benzoxazolyl, oxopiperidinyl, oxopyrrolidinyl, oxoazepinyl, azepinyl, isoxozolyl, isothiazolyl, furazanyl, tetrahydropyranyl, tetrahydrofuranyl, thiazolyl, thiadiazoyl, dioxolyl, dioxinyl, oxathiolyl, benzodioxolyl, dithiolyl, thiophenyl, tetrahydrothiophenyl, sulfolanyl, dioxanyl, dioxolanyl, tetrahydrofurodihydrofuranyl, tetrahydropyuranodihydrofuranyl, dihydropyranyl, tetradyrofurofuranyl and tetrahydropyranofuranyl.

Preferred heterocycles include imidazolyl, pyrrolyl, pyrrolinyl, piperidinyl, piperazinyl, and morpholinyl.

The term "halo atom" or "halogen" refers to a radical of fluorine, chlorine, bromine or iodine.

The term "haloC$_{1-6}$alkyl" means an alkyl group in which one or more hydrogens is replaced by halo and preferably containing one, two or three halo groups. Examples of such groups include trifluoromethyl and fluoroisopropyl.

The term "pharmaceutically effective amount" refers to an amount effective in treating a viral infection in a patient either as monotherapy or in combination with other agents. The term "treating" as used herein refers to the alleviation of symptoms of a particular disorder in a patient or the improvement of an ascertainable measurement associated with a particular disorder. The term "prophylactically effective amount" refers to an amount effective in preventing viral infection in a patient. As used herein, the term "patient" refers to a mammal, including a human.

The term "pharmaceutically acceptable carrier or adjuvant" refers to a carrier or adjuvant that may be administered to a patient, together with a compound of this invention, and which does not destroy the pharmacological activity thereof and is nontoxic when administered indoses sufficient to deliver a therapeutic amount of the antiviral agent.

As used herein, the compounds according to the invention are defined to include pharmaceutically acceptable derivatives or prodrugs thereof. A "pharmaceutically acceptable derivative" or "pharmaceutically acceptable prodrug" means any pharmaceutically acceptable salt, ester, salt of an ester, solvate, such as ethanolate, or other derivative of a compound of this invention which, upon administration to a recipient, is capable of providing (directly or indirectly) a compound of this invention or an inhibitorily active metabolite or residue thereof. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species.

The compounds according to the invention may be used in the form of salts derived from inorganic or organic acids. Included among such acid salts, for example, are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectianate, persulfate, phenylproprionate, picrate, pivalate, propionate, succinate, tartrate, thiocyanate, tosylate and undecanoate.

Pharmaceutically acceptable salts of the compounds according to the invention include those derived from pharmaceutically acceptable inorganic and organic acids and bases. Examples of suitable acids include hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, ethanesulfonic, formic, benzoic, malonic, naphthalene-2-sulfonic and benzenesulfonic acids. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g. sodium), alkaline earth metal (e.g., magnesium), ammonium and N–W+4 (wherein W is $C_{1-4}$ alkyl). Physiologically acceptable salts of a hydrogen atom or an amino group include salts or organic carboxylic acids such as acetic, lactic, tartaric, malic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids. Physiologically acceptable salts of a compound with a hydroxy group include the anion of said compound in combination with a suitable cation such as $Na^+$, $NH_{4+}$, and $NW_4+$(wherein W is a $C_{1-4}$alkyl group).

Pharmaceutically acceptable salts include salts of organic carboxylic acids such as ascorbic, acetic, citric, lactic, tartaric, malic, maleic, isothionic, lactobionic, p-aminobenzoic and succinic acids; organic sulphonic acids such as methanesulphonic, ethanesulphonic, benzenesulphonic and p-toluenesulphonic acids and inorganic acids such as hydrochloric, sulphuric, phosphoric, sulphamic and pyrophosphoric acids.

For therapeutic use, salts of the compounds of formula (I) will be pharmaceutically acceptable. However, salts of acids and bases which are non-pharmaceutically acceptable may also find use, for example, in the preparation or purification of a pharmaceutically acceptable compound.

Preferred salts include salts formed from hydrochloric, sulfuric, acetic, succinic, citric and ascorbic acids.

Preferred esters of the compounds according to the invention are independently selected from the following groups: (1) carboxylic acid esters obtained by esterification of the 2'-, 3'- and/or 5'-dehydroxy groups, in which the nonarbonyl moiety of the carboxylic acid portion of the ester grouping is selected from straight or branched chain alkyl (for example, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted by, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

In such esters, unless otherwise specified, any alkyl moiety present advantageously contains from 1 to 18 carbon atoms, particularly from 1 to 6 carbon atoms, more particularly from 1 to 4 carbon atoms, Any cycloalkyl moiety present in such esters advantageously contains from 3 to 6 carbon atoms. Any aryl moiety present in such esters advantageously comprises a phenyl group.

Any reference to any of the above compounds also includes a reference to pharmaceutically acceptable salts thereof.

Ethers of the compounds according to the invention include methyl, ethyl, propyl, butyl, isobutyl, and sec-butyl ethers.

In a further aspect of the invention there are provided the compounds according to the invention for use in medical therapy particularly for the treatment or preophylaxis of viral infections such as herpes viral infections. Compounds of the invention have been shown to be active against CMV infections, although early results suggest that these compounds could also be active against other herpes virus infections such as HSV-1 and-2, HHV 6 and 7, VZV, EBV and HBV infections.

Other viral conditions which may be treated in accordance with the invention have been discussed in the introduction hereinbefore. The compounds of the present invention are particularly suited to the treatment or prophylaxis of CMV infections and associated conditions. Examples of CMV conditions which may be treated in accordance with the invention have been discussed in the introduction hereinbefore.

According to another aspect, the present invention provides a method for the treatment or prevention of the symptoms or effects of a viral infection in an infected animal, for example, a mammal including a human, which comprises treating said animal with a therapeutically effective amount of a compound according to the invention. According to a particular embodiment of this aspect of the invention, the viral infection is a herpes virus infection, such as CMV, HSV-1, HSV-2, VZV, EBV, HHV6 or HHV7. A further aspect of the invention includes a method for the treatment or prevention of the symptoms or effects of an HBV infection.

The present invention further provides a method for the treatment of a clinical condition in an animal, for example, a mammal including a human which clinical condition includes those which have been discussed in the introduction hereinbefore, which comprises treating said animal with a therapeutically effective amount of a compound according to the invention. The present invention also includes a method for the treatment or prophylaxis of any of the aforementioned infections or conditions.

In yet a further aspect, the present invention provides the use of a compound according to the invention in the manufacture of a medicament for the treatment or prophylaxis of any of the above mentioned viral infections or conditions.

The above compounds according to the invention and their pharmaceutically acceptable derivatives may be employed in combination with other therapeutic agents for the treatment of the above infections or conditions. Combination therapies according to the present invention comprise the administration of at least one compound of the formula (I) or a pharmaceutically acceptable derivative thereof and at least one other pharmaceutically active ingredient. The active ingredient(s) and pharmaceutically active agents may be administered simultaneously in either the same or different pharmaceutical formulations or sequentially in any order. The amounts of the active ingredient(s) and pharmaceutically active agent(s) and the relative timings of administration will be selected in order to achieve the desired combined therapeutic effect. Preferably the combination therapy involves the administration of one compound according to the invention and one of the agents mentioned herein below.

Examples of such further therapeutic agents include agents that are effective for the treatment of viral infections or associated conditions are (1 alpha, 2 beta, 3 alpha)-9-[2,3-bis(hydroxymethyl)cyclobutyl]guanine [(−)BHCG, SQ-34514], oxetanocin-G(3,4-bis(hydroxymethyl)-2-oxetanosyl]guanine), acyclic nucleosides (e.g. acyclovir, valaciclovir, famciclovir, ganciclovir, penciclovir), acyclic nucleoside phosphonates (e.g. (S)-1-(3-hydroxy-2-phosphonyl-methoxypropyl)cytosine (HPMPC), ribonucleotide reductase inhibitors such as 2-acetylpyridine 5-[(2-chloroanilino)thiocarbonyl)thiocarbonohydra-zone, 3'azido-3'-deoxythymidine, other 2',3'-dideoxynucleosides such as 2',3'-dideoxycytidine, 2',3'-dideoxyadenosine, 2',3'-dideoxyinosine, 2',3'-didehydrothymidine, protease inhibitors such as ritonovir, indinavir, 141W94, nelfinavir, sanquinavir, and 3S-[3R*(1S*,2R*)]-[3-[[(4-aminophenyl)sulphonyl](2-methylpropyl)-amino]-2-hydroxy-1-phenylmethyl)propyl]carbamic acid, tetrahydro-3-furanyl ester (141W94), oxathiolane nucleoside analogues such as (−)-cis-1-(2-hydroxymethyl)-1,3-oxathiolane 5-yl)-cytosine (lamivudine) or cis-1-(2-(hydroxymethyly1,3-oxathiolan-5-yl)-5-fluorocytosine (FTC), 3'-deoxy-3'-fluorothymidine, 5-chloro-2',3'-dideoxy-3'-fluorouridine, (−)-cis-4-[2-amino-6-(cyclopropylamino)-9H-purin-9-yl]-2-cyclopentene-1-methanol, ribavirin, 9-[4-hydroxy-2-(hydroxymethyl)but-1-yl]-guanine (H2G), tat inhibitors such as 7-chloro-5-(2-pyrryl)-3H-1,4-benzodiazepin-2-(H)one (Ro5-3335), 7-chloro-1,3-dihydro-5-(1H-pyrrol-2yl)-3H-1,4-benzodiazepin-2-amine (Ro24-7429), interferons such as α-interferon, renal excretion inhibitors such as probenecid, nucleoside transport inhibitors such as dipyridamole; pentoxifylline, N-acetylcysteine (NAC), Procysteine, α-trichosanthin, phosphonoformic acid, as well as immuno-modulators such as interleukin II or thymosin, granulocyte macrophage colony stimulating factors, erythropoetin, soluble $CD_4$ and genetically engineered derivatives thereof, or non-nucleoside reverse transcriptase inhibitors such as nevirapine (BI-RG-587), loviride (α-APA) and delavuridine (BHAP), and phosphonoformic acid.

More preferably the combination therapy involves the administration of one of the above mentioned agents and a compound within one of the preferred or particularly preferred sub-groups within formula (I) as described above. Most preferably the combination therapy involves the joint use of one of the above named agents together with one of the compounds of formula (I) specifically named herein.

The present invention further includes the use of a compound according to the invention in the manufacture of a medicament for simultaneous or sequential administration with at least one other therapeutic agent, such as those defined hereinbefore.

In a further aspect of the present invention there is provided a method of treatment or prophylaxis of restenosis by administration of a compound according to the invention.

Restensosis is the narrowing of the blood vessels which can occur after injury to the vessel wall, for example injury caused by balloon angioplasty or other surgical techniques, and is characterized by excessive proliferation of smooth muscle cells in the walls of the blood vessel treated. Restenosis following angioplasty (RFA) occurs in patients who have been treated for coronary artery disease by balloon angioplasty. It is thought that in many patients suffering from RFA, viral infection, particularly by CMV and/or HHV-6, of the patient plays a pivotal role in the proliferation of the smooth muscle cells in the coronary vessel treated.

Restenosis can occur following a number of surgical techniques, for example, transplant surgery, vein grafting, coronary by-pass grafting and, most commonly, following angioplasty.

Angioplasty is a surgical technique wherein atherosclerotic stenoses in the peripheral, renal and coronary vasculature are opened up by compressing and/or tearing the plaque on the vessel walls, typically by means of a pressurized balloon catheter. Unfortunately, in 25 to 50% of cases, particularly those involving the coronary vasculature, the treated vessel restenoses within a few months so that the operation must be repeated. Alternatives to the balloon catheter, such as pulsed lasers and rotary cutters, have been developed with a view to reducing or preventing restenosis following angioplasty, but have met with limited success. A number of drugs including anti-coagulants and vasodilators have also been tried with disappointing or equivocal results.

There is now a strong body of evidence, from work done both in vitro and in vivo, indicating that restenosis is a multifactorial process. Several cytokines and growth factors, acting in concert, stimulate the migration and proliferation of vascular smooth muscle cells (SMC) and production of extracellular matrix material, which accumulate to occlude the blood vessel. In addition growth suppressors act to inhibit the proliferation of SMC's and production of extracellular matrix material.

The present invention further includes a process for the preparation of compounds of formula (I) and pharmaceutically acceptable derivatives thereof which comprises:

A. Reacting a compound of formula (I) wherein $R^3$ is hydrogen and $R^4$, $R^5$, $R^6$ and $R^7$ are as hereinbefore defined, and $R^1$ and $R^2$ are a hydroxy group, protected hydroxy or a fluorine atom, with a suitable halogenation agent such as N-bromosuccinimide (NBS); or when $R^3$ is a suitable leaving atom or group, for example, a halo atom such as bromine or an organo (for example alkyl) sulphone, or organo (for example alkyl or aralkyl) sulphonate such as methylsulphone ($MeS(O)_2$—), methylsulphonate ($MeS(O)_2O$—) or tosylate (4-$MePhS(O)_2O$—) with an amine of the formula $HNR^8R^9$ (wherein $R^8$ and $R^9$ are as hereinbefore defined), an alcohol of formula $HOR^{10}$ (where $R^{10}$ is as hereinbefore defined), a thiol of the formula HSR$^{11}$ (wherein R$^{11}$ is as hereinbefore defined), or a suitable displacing agent such as tetrabutyl ammonium azide or sodium azide or potassium azide.

B. Reacting a compound of formula (II).

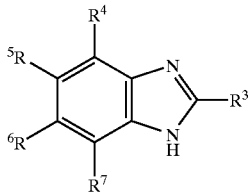
(II)

wherein R$^3$ is hydrogen, a halo atom, —NR$^8$R$^9$ (wherein R$^8$ and R$^9$ are as hereinbefore defined), and R$^4$, R$^5$, R$^6$ and R$^7$ are as hereinbefore described with a compound of formula (III)

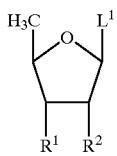
(III)

wherein R$^1$ and R$^2$ are as is hereinbefore defined and L$^1$ is a suitable leaving group in the alpha or beta position, for example, a halo (for example, fluoro, chloro or bromo), an alkyl or arylthio (for example, phenylthio) or an aryl or aliphatic ester group such as benzoate or acetate; and thereafter or simultaneously therewith effecting one or more of the following further steps may be additionally performed in any desired or necessary order:

(i) removing any remaining protecting group(s);
(ii) converting a compound of formula (I) or a protected form thereof into a further compound of formula (I) or protected form thereof;
(iii) converting the compound of formula (I) or a protected form thereof into a pharmaceutically acceptable derivative of the compound of formula (I) or a protected form thereof;
(iv) converting a pharmaceutically acceptable derivative of the compound of formula (I) or a protected form thereof into the compound of formula (I) of a protected form thereof;
(v) converting a pharmaceutically acceptable derivative of the compound of formula (I) or a protected form thereof into another pharmaceutically acceptable derivative of the compound of formula (I) or a protected form thereof;
(vi) where necessary, separating the alpha and beta anomers of the compound of formula (I) or of a protected derivative thereof or of a pharmaceutically acceptable derivative of a compound of formula (I).

Process A may conveniently be used for the preparation of a compound of formula (I) wherein R$^3$ is a halogen. Such compounds may conveniently be prepared by reacting a compound of formula (I) wherein R$^3$ is hydrogen and R$^1$, R$^2$, R$^4$, R$^5$, R$^6$ and R$^7$ are as hereinbefore defined with a halogenating agent. Halogenation may be effected in a conventional manner, for example, bromination using a brominating agent such as N-bromosuccinimide (NBS) in an aprotic solvent such as tetrahydrofuran (THF) or preferably 1,4-dioxane heated to 60–150° C., preferably, 100° C.

Compounds of formula (I) wherein R$^3$ is —NR$^8$R$^9$ (wherein R$^8$ and R$^9$ are as hereinbefore defined) may conveniently be prepared from compounds of formula (I) wherein R$^3$ is a halo atom, such as bromo or chloro atom, by reaction with an appropriate amine HNR$^8$R$^9$, wherein R$^8$ and R$^9$ are as hereinbefore defined. Typically, the reaction is effected at an elevated temperature, 70–80° C., in an organic solvent such as ethanol or dimethylsulfoxide. Amines of formula HNR$^8$R$^9$ are commercially available or are readily prepared by a person skilled in the art.

Compounds of formula (I) wherein R$^3$ is —OR$^{10}$ (wherein R$^{10}$ is as hereinbefore defined) may conveniently be prepared from compounds of formula (I) wherein R$^3$ is a halo atom, such as bromo or chloro atom, by reaction with an appropriate alcohol of formula HOR$^8$ (wherein R$^8$ is as hereinbefore defined). Typically, the reaction is effected at −20 to 100° C., preferably at 25° C., in HOR$^8$ or dimethylsulfoxide as solvent and in the presence of a strong base such as sodium hydride. Alcohols of formula HOR$^8$ are available commercially or may be readily prepared by a person skilled in the art.

Compounds of formula (I) wherein R$^3$ is —SR$^{11}$ (wherein R$^{11}$ is as hereinbefore defined) may conveniently be prepared from compounds of formula (I) wherein R$^3$ is a halo atom, such as bromo or chloro atom, by reaction with an appropriate thiol of formula HSR$^{11}$ (wherein R$^{11}$ is as hereinbefore defined). Typically, the reaction is effected at −20 to 100° C., preferably at 25° C., in N,N-dimethylformamide or dimethylsulfoxide as solvent and in the presence of a strong base such as sodium or potassium hydride. Thiols of formula HSR$^{11}$ are available commercially or may be readily prepared by a person skilled in the art.

Compounds of formula (I) wherein R$^3$ is azido may conveniently be prepared from compounds of formula (I) wherein R$^3$ is a halo atom, such as bromo or chloro atom, by reaction with an appropriate displacing agent such as tetrabutyl ammonium azide or potassium or sodium azide. Typically, the reaction is effected at an elevated temperature from 75–150° C., preferably at 100° C., and in the presence of a polar, aprotic solvent such as dimethylsulfoxide, preferably N,N-dimethylformamide.

Compounds of formula (I) in which R$^3$, R$^4$, R$^5$, R$^6$ or R$^7$ is an alkenyl group and R$^1$ and R$^2$ are as hereinbefore defined can be prepared from compounds of formula (I) wherein R$^3$, R$^4$, R$^5$, R$^6$ or R$^7$ are a halo atom, preferably a bromo atom, by reaction with an alkenyl trialkyltin (IV) reagent, such as vinyl tributyltin. These reactions are typically effected in the presence of a palladium catalyst such as tetrakis(triphenylphosphine)palladium (0), palladium (II) acetate, or palladium (II) chloride bis(acetonitrile) also in the presence of a solvent such as N,N-dimethylformamide and at an elevated temperature, preferably 90° C. The desired alkenyl trialkyltin (IV) reagent is available commercially or may be readily prepared by a person skilled in the art.

Compounds of formula (I) in which R$^3$, R$^4$, R$^5$, R$^6$ or R$^7$ is an alkynyl group and R$^1$ and R$^2$ are as hereinbefore defined may be conveniently prepared from compounds of formula (I) wherein R$^3$, R$^4$, R$^5$, R$^6$ or R$^7$ is a halo atom, preferably a bromo atom, by reaction with a terminal acetylene, such as trimethylsilylacetylene. Typically, the reaction is effected in the presence of a palladium catalyst such as tetrakis(triphenylphosphine)palladium (0), palladium (II) acetate, or palladium (II) chloride bis(acetonitrile) and in the presence of copper (I) iodide. The reaction is also performed in the presence of a solvent, preferably N,N-dimethylformamide and a base, preferably triethylamine and at an elevated temperature from 40–100° C., preferably 80° C. The desired terminal acetylene may be obtained commercially or may be readily prepared by a person skilled in the art.

Compounds of formula (I) in which $R^4$, $R^5$, $R^6$ or $R^7$ is an aryl or heterocyclic group, and $R^1$ and $R^2$ are as hereinbefore defined, may be prepared from compounds of formula (I) in which $R^4$, $R^5$, $R^6$ or $R^7$ is a halo atom, such as a bromo atom, by reaction with an aryl or heterocyclic trialkyltin (IV) reagent. These reactions are typically effected in the presence of a palladium catalyst such as tetrakis(triphenylphosphine)palladium (0), palladium (II) acetate, or palladium (II) chloride bis(acetonitrile) also in the presence of a solvent such as N,N-dimethylformamide and at an elevated temperature, preferably 90° C. The desired aryl or heterocyclic trialkyltin (IV) reagent may be obtained commercially or may be readily prepared by a person skilled in the art.

Alternatively, compounds of formula (I) in which $R^4$, $R^5$, $R^6$ or $R^7$ is a heterocyclic group, and $R^1$ and $R_2$ are as hereinbefore defined, may be prepared from compounds of formula (I) in which $R^4$, $R^5$, $R^6$ or $R^7$ is a nitrile radical by reaction with an agent capable of cyclizing the nitrile into a heterocycle. An example of such an agent is sodium azide, which upon reaction with a nitrile radical produces a tetrazolyl group. This reaction is typically effected in the presence of tributyltin (IV) chloride and in an aromatic solvent, toluene for example, and in the temperature range from 75–200° C., preferably 110° C.

Compounds of formula (I) in which $R^4$, $R^5$, $R^6$ or $R^7$ is —C(O)NR$^{14}$R$^{15}$, wherein $R^{14}$ and $R^{15}$ are as hereinbefore defined, may be prepared from compounds of formula (I) in which $R^4$, $R^5$, $R^6$ or $R^7$ is a nitrile radical by reaction with acid and water. This reaction is typically effected in a polar solvent, such as water, and in the presence of hydrogen peroxide at 25–100° C., preferably 35° C. Additionally, the reaction can be effected in the presence of an alkyl halide when $R^{14}$ an alkyl group and $R^{15}$ is either hydrogen or an alkyl group.

The protecting groups may be removed by conventional chemical techniques well known to a skilled person.

Compounds of formula (I) wherein $R^1$ is a hydroxy group, $R^2$ is either a hydroxy group or a fluorine atom and $R^3$, $R^4$, $R^5$, $R^6$ and $R^7$ are as hereinbefore defined may be prepared from a corresponding compound of formula (I) wherein $R^1$ is a protected hydroxy group and $R^2$ is a protected hydroxy group or a fluorine atom. Conventional protecting groups may be used for $R^1$ and $R^2$. Advantageously, ester groups such as those described above in relation to the esters of compounds of formula (I) may be used. These protecting groups may be removed either by conventional chemical techniques such as sodium carbonate in water and methanol or enzymatically, for example, using pig liver esterase. Alternatively, $R^1$ and $R^2$ may include silyl ethers such as tert-butyldiphenyl-, tert-butyldimethyl-, and triisopropylsilyl ethers which may be deprotected to give a hydroxyl group using an appropriate fluoride source, for example HF/pyridine, Bu$_4$NF or Et$_4$NF or a cyclic acetal or ketal such as benzylidene or isopropylidene which can be removed under acidic conditions, for example, using tosic acid and methanol.

Alternatively, the compounds of formula (I) where $R^1$ is a protected hydroxy group and $R^2$ is either a protected hydroxy group or a fluorine atom and $R^4$, $R^5$, $R^6$ and $R^7$ are as hereinbefore defined may be reacted with an agent or under conditions whereby the leaving group $R^3$ is converted to the desired $R^3$ group simultaneously with removal of the protecting groups. Examples of such agents include cyclopropylamine and other primary and secondary amines providing that these agents are sufficiently nucleophilic and are not sterically hindered.

B. Compounds of formula (I) wherein $R^3$ is as hereinbefore defined may be prepared by reaction of a compound of formula (II) wherein $R^3$ is hydrogen, a halo atom or —NR$^8$R$^9$ (wherein $R^8$ and $R^9$ are as hereinbefore defined) and $R^4$, $R^5$, $R^6$ and $R^7$ are as hereinbefore defined, with a compound of formula (III), wherein $R^1$ and $R^2$ are each a hydroxy or protected hydroxy group and $L^1$ is as hereinbefore described. The reaction of compounds of formula (II) with those of formula (III) may be effected using a Lewis acid such as trimethylsilyl trifluoromethanesulfonate, stannic chloride, or boron trifluoride, the former being preferred. The reaction is generally effected in an aprotic solvent and at an elevated temperature, for example, in acetonitrile at 15–30° C. or 1,2-dichloroethane at 70–90° C.

The compound of formula (II) is advantageously trimethylsilylated at the $N_1$-position in the above procedures to improve solubility; for example, by treatment with trimethylsilylchloride, hexamethyl disilazane or, most preferably, N,O-bis(trimethylsilyl)acetamide (BSA). The silylation can be effected in a solvent, preferably 1,2-dichloroethane or acetonitrile, preferably at 70–80° C. After completion of the silylation reaction, a Lewis acid may be added, followed by the addition of the compound of formula (III).

Compounds of formula (I), of the beta-D-ribofuranosyl configuration, wherein $R^1$, $R^4$, $R^5$, $R^6$, and $R^7$ are as hereinbefore defined, $R^2$ is fluoro and $R^3$ is hydrogen may be prepared enzymatically by reacting a compound of formula (II) where $R^3$ is hydrogen and $R^4$, $R^5$, $R^6$ and $R^7$ are as hereinbefore defined with a suitable carbohydrate donor such as a compound of formula (IV):

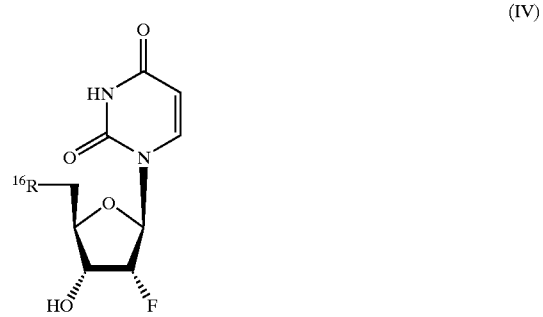

(IV)

where $R^{16}$ is hydrogen. Enzymatic synthesis can be accomplished by N-deoxyribosyl transferase. The latter enzyme can be isolated by the procedure outlined by Cook, et. al., J. Biol. Chem. 1990, 265, 2682.

Compounds of formula (IV) where $R^{16}$ hydrogen may be prepared from compounds of formula (IV) where $R^{16}$ is a halo atom such as iodo with a suitable reducing agent such as tributyltin hydride or palladium on carbon in the presence of a base such as ammonium hydroxide. This reaction is typically effected at ambient temperature in the presence of a solvent such as ethanol.

Compounds of formula (IV) where $R^{16}$ is a halo atom such as iodo may be prepared from compounds of formula (IV) where $R^{16}$ is hydroxy by reaction with a suitable halogenating agent such as methyltriphenoxyphosphonium iodide. This reaction is typically effected in the presence of a solvent such as N,N-dimethylformamide at ambient temperatures.

Compounds of formula (IV) where $R^{16}$ is a hydroxy group may be prepared according to the method of Codington, et. al. J. Org. Chem. 1964, 29, 558.

Compounds of formula (III) wherein $L^1$, $R^1$ and $R^2$ are protected hydroxy groups, such as esters, most preferably $OC(O)CH_3$, may be prepared by literature methods well known to a person skilled in the art. For instance, the compound of formula (III) which is in the beta-D-ribofuranosyl configuration may be prepared according to the method of Kiss, J. et al, Helv. Chim. Acta. 1982, 65, 1522.

Compounds of formula (II), wherein $R^3$ is hydrogen or a halo atom, most preferably chloro or bromo, and $R^4$, $R^5$, $R^6$ and $R^7$ are as hereinbefore defined, may be prepared in accordance with the methods described in PCT specifications WO 92/07867 incorporated herein by reference. Alternatively, compounds of formula (II), wherein $R^3$ is hydrogen or a halo atom, most preferably chloro or bromo, and $R^4$, $R^5$, $R^6$ and $R^7$ are as hereinbefore defined, may be prepared in accordance with the methods described by Leroy Townsend, et al. J. Med. Chem., Vol. 38, 1995, pg. 4098.

Alternatively, compounds of formula (II) wherein $R^3$ is $-NR^8R^9$, wherein $R^8$ and $R^9$ are as hereinbefore defined, may be prepared by reacting a compound of formula (V)

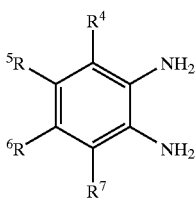

(V)

wherein $R^4$, $R^5$, $R^6$ and $R^7$ are as hereinbefore defined, with an agent capable of cyclizing the diamine into a benzimidazole. Typically, compounds of formula (V) may be reacted with an isothiocyanate of formula (VI)

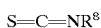

S=C=NR$^8$ (VI)

wherein $R^8$ is as hereinbefore defined. The reaction may be carried out in the presence of an agent to promote cyclization such as methyl iodide or a carbodiimide such as dicyclohexyl carbodiimide or 1-cyclohexyl-3-(2-morpholinoethyl) carbodiimide metho-p-toluenesulfonate in the presence of an aprotic aromatic solvent such as toluene and most preferably pyridine and at an elevated temperature, preferably 75–150° C.

Compounds of formula (VI) may be prepared by methods well known to a skilled person or readily available in the chemical literature or obtained commercially.

Compounds of formula (II) wherein $R^3$ is hydrogen may be obtained commercially or alternatively may be prepared by reacting a compound of formula (V) wherein $R^4$, $R^5$, $R^6$ and $R^7$ are as hereinbefore defined with formamidine or most preferably formic acid at ambient temperature to 100° C., most preferably 80° C.

Compounds of formula (V) may be prepared by methods well known to a skilled person or readily available in the chemical literature or obtained commercially.

Alternatively, compounds of formula (V) may be conveniently prepared from compounds of formula (VII)

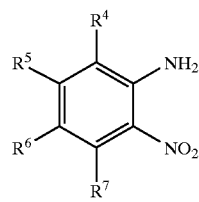

(VII)

wherein $R^4$, $R^5$, $R^6$ and $R^7$ are as hereinbefore defined, in the presence of a reducing agent, reduced iron for example, and in the presence of an acid, most preferably hydrochloric acid, and in the presence of a solvent such as ethyl alcohol and in the temperature range of 50–78° C. (B. Fox and T. L. Threlfall, Org. Syn. Coll. Vol. 5, 1973, p. 346). Alternatively, such ortho phenylenediamines may be prepared in the presence of a reducing agent such as Raney nickel also in the presence of hydrogen. This reaction is also run in the presence of a solvent, ethyl alcohol for example, at ambient temperature (K. Dimroth, et al, Org. Syn. Coll. Vol. 5, 1973, p.1130). Alternatively, such ortho phenylenediamines may be prepared in the presence of a reducing agent such as sodium hydrosulfite. Typically this reaction is effected in the presence of a polar, protic solvent, preferably a mixture of water and ethanol, and at an elevated temperature, preferably reflux.

Compounds of formula (VII) may be prepared by methods well known to a skilled person or are readily available commercially. Alternatively, compounds of formula (VII), where $R^4$ is a halogen atom such as fluorine, chlorine or bromine atom, and $R^5$, $R^6$ and $R^7$ are as hereinbefore defined, may be prepared from compounds of formula (VII) wherein $R^4$ is hydrogen by reaction with an appropriate halogenating agent such as 1-fluoro-1,4-diazoniabicyclo[2.2.2]octane bis(tetrafluoroborate), N-chlorosuccinimide or N-bromosuccinimide, in the presence of an aprotic solvent such as acetonitrile or N,N-dimethylformamide and at an elevated temperature from 50–100° C.

Alternatively, compounds of formula (VII) wherein $R^5$ is $-SR^{12}$ (wherein $R^{12}$ is as hereinbefore defined) may be prepared from compounds of formula (VII) wherein $R^5$ is a halo atom and $R^4$, $R^6$, $R^7$ and $R^8$ are as hereinbefore defined by reaction with $HSR^{12}$. This reaction is typically effected in the presence of a strong base such as sodium or potassium hydride and in the presence of a solvent such as dimethylsulfoxide, most preferably N,N-dimethylformamide at ambient temperatures.

Alternatively, compounds of formula (VII) may advantageously be prepared from compounds of formula (VIII),

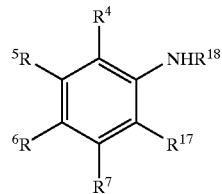

(VIII)

wherein $R^{17}$ is hydrogen, $R^{18}$ is a protecting group such as an amide, trifluoroacetamide for example, and $R^4$, $R^5$, $R^6$ and $R^7$ are as hereinbefore defined, by reaction with a nitrating agent such as nitric acid. This reaction is effected in a solvent such as sulfuric acid at temperatures of −20 to 25° C., most preferably at 0° C. The protecting group, $R^{18}$, may be conveniently removed at the end of the reaction sequence with either acid, 2 normal sulfuric acid for example, or base, sodium carbonate in methanol and water for example, at temperatures of 25–100° C.

Compounds of formula (VIII) wherein $R^{17}$ is hydrogen and $R^{18}$ is a protecting group such as an amide, trifluoroacetamide for example, and $R^4$, $R^5$, $R^6$ and $R^7$ are as hereinbefore defined, may be prepared from compounds of formula (VIII) wherein $R^{17}$ and $R^{18}$ are hydrogen and $R^4$, $R^5$, $R^6$ and $R^7$ are as hereinbefore defined by reaction with an appropriate acylating agent such as trifluoroacetic anhydride. These reactions are effected in the presence of an aprotic solvent such as acetontrile, most preferably 1,4-dioxane, from −10 to 40° C., most preferably at 0° C.

Alternatively, compounds of formula (VII) in which $R^4$, $R^5$, $R^6$ and $R^7$ are as hereinbefore defined can be prepared from compounds of formula (IX)

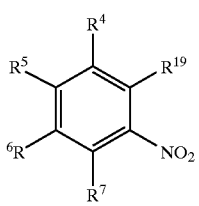

(IX)

wherein $R^{19}$ is a halo atom, fluoro or chloro atom for example, by reaction with ammonia. These reactions are typically effected in the presence of a solvent such as ethyl alcohol or 1,4-dioxane and at elevated temperatures, preferably 100° C.

Compounds of formula (VIII) in which $R^{17}$ and $R^{18}$ are hydrogen and $R^4$, $R^5$, $R^6$ and $R^7$ are as hereinbefore defined may be prepared by methods well known to a skilled person or readily available in the chemical literature or obtained commercially.

Compounds of formula (IX) may be obtained commercially or may be readily prepared by a person skilled in the art.

Compounds of formula (I) in which $R^1$ is a fluorine atom, $R^2$ is a hydroxy or protected hydroxy group and $R^3$, $R^4$, $R^5$, $R^6$ and $R^7$ are as hereinbefore defined may be prepared by reacting compounds of formula (II), wherein $R^3$, $R^4$, $R^5$, $R^6$ and $R^7$ are as hereinbefore defined, with a compound of formula (X),

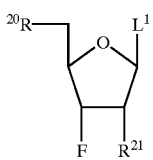

(X)

in which $R^{20}$ is hydrogen, $R^{21}$ is a hydroxy or protected hydroxy group and $L^1$ is as hereinbefore defined. The reaction of compounds of formula (II) with those of formula (X) may be effected using a Lewis acid such as trimethylsilyl trifluoromethanesulfonate, stannic chloride, or boron trifluoride, the former being preferred. The reaction is generally effected in an aprotic solvent and at an elevated temperature, for example, in acetonitrile at 15–30° C. or 1,2-dichloroethane at 70–90° C.

Compounds of formula (X) in which $R^{20}$ is hydrogen and $R^{21}$ and $L^1$ are as hereinbefore defined may be prepared by reaction of compound of formula (X), in which $R^{20}$ is hydroxy, $R^{21}$ is a benzyloxy group and $L^1$ is methoxy with a chlorothionoformate, such as phenyl chlorothionoformate followed by reaction of the intermediate thiocarbonate with a reductant, such as tributyltin hydride. This reaction is typically effected in the presence of a radical initiator, AIBN for instance, and in the presence of an aromatic solvent, toluene for instance. The benzyloxy group can then be removed under reductive conditions using a catalyst, such as palladium on carbon, and a reductant, such as hydrogen. This reaction is also effected in the presence of a polar solvent, such as ethanol, and at 25–100° C., preferably ambient temperature.

This intermediate can then converted to a compound of formula (X) in which $R^{20}$ is hydrogen and $R^{21}$ and $L^1$ are esters, acetyl esters for instance, by reaction with an acid, acetic acid for instance, and an acylating agent, acetic anhydride for instance. This reaction is typically effected in the acylating agent as solvent at 0–100° C., preferably 25° C.

Compounds of formula (X) in which $R^{20}$ is hydroxy, $R^{21}$ is benzyloxy and $L^1$ is methoxy may be prepared from compounds of formula (X) in which $R^{20}$ is a protected hydroxy group, such as tert-butyldimethylsilyl ether, and $R^{21}$ is a hydroxy group, by reaction with a benzylating agent, such as benzyl bromide. This reaction is typically effected in a polar solvent, dimethyl formamide for instance, and at 25–110° C., preferably 50° C.

Compounds of formula (X) in which $R^{20}$ is a protected hydroxy group, such as a tert-butyldimethylsilyl ether, $R^{21}$ is a hydroxy group and $L^1$ is methoxy, may be prepared from compounds of formula (X) in which $R^{20}$ and $R^{21}$ are hydroxyl and $L^1$ is methoxy, by reaction with a silylating agent, such as tert-butyldimethylsilyl chloride. This reaction is typically effected in a polar, aprotic solvent such as N,N-dimethylformamide in the presence of a base, imidazole for instance, at 25–100° C., preferably ambient temperature.

Compounds of formula (X) in which $R^{20}$ and $R^{21}$ are hydroxy and $L^1$ is methoxy, may be prepared from compounds of formula (X) wherein $R^{20}$ and $R^{21}$ are protected hydroxy groups, such as tert-butyldimethylsilyl ethers, and $L^1$ is methoxy, by reaction with a fluoride source, tetrabutylammonium fluoride for example. This reaction is typically effected in a polar solvent such as acetonitrile at a temperature of 25–100° C., preferably ambient temperature.

Compounds of formula (X) in which $R^{20}$ and $R^{21}$ are protected hydroxy groups, such as tert-butyldimethylsilyl ethers and $L^1$ is methoxy, may be prepared from compounds of formula (XI)

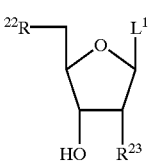

(XI)

in which $R^{22}$ and $R^{23}$ are protected hydroxy groups, such as tert-butyldimethylsilyl ethers, by reaction with a fluorinating agent, diethylaminosulfur trifluoride for example. This reaction is typically effected in an aprotic solvent, such as chloroform or toluene, and at an elevated temperature, preferably 75° C.

Compounds of formula (XI) in which $R^{22}$ and $R^{23}$ are protected hydroxy groups, such as tert-butyldimethylsilyl ethers and $L^1$ is methoxy, may be prepared from compounds of formula (XI) in which $R^{22}$ and $R^{23}$ are hydroxy groups and $L^1$ is methoxy by reaction with a silylating agent such as tert-butyldimethylsilyl chloride. This reaction is typically effected in a polar, aprotic solvent, such as N,N-dimethylformamide, and in the presence of a base such as, imidazole at 25–100° C., preferably 25° C.

Compounds of formula (XI) in which $R^{22}$ and $R^{23}$ are hydroxyl and $L^1$ is methoxy may be readily prepared according to literature conditions well-known to a person skilled in the art.

The compounds according to the invention, also referred to herein as the active ingredient, may be administered for therapy by any suitable route including oral, rectal, nasal, topical (including transdermal, buccal and sublingual), vaginal and parenteral (including subcutaneous, intramuscular, intravenous, intradermal, and intravitreal). It will be appreciated that the preferred route will vary with the condition and age of the recipient, the nature of the infection and the chosen active ingredient.

In general a suitable dose for each of the above-mentioned conditions will be in the range of 0.01 to 250 mg per kilogram body weight of the recipient (e.g. a human) per day, preferably in the range of 0.1 to 100 mg per kilogram body weight per day and most preferably in the range 0.5 to 30 mg per kilogram body weight per day and particularly in the range 1.0 to 20 mg per kilogram body weight per day. Unless otherwise indicated, all weights of active ingredient are calculated as the parent compound of formula (I); for salts or esters thereof, the weights would be increased proportionally. The desired dose may be presented as one, two, three, four, five, six or more sub-doses administered at appropriate intervals throughout the day. In some cases the desired dose may be given on alternative days. These sub-doses may be administered in unit dosage forms, for example, containing 10 to 1000 mg or 50 to 500 mg, preferably 20 to 500 mg, and most preferably 100 to 400 mg of active ingredient per unit dosage form.

While it is possible for the active ingredient to be administered alone it is preferable to present it as a pharmaceutical formulation. The formulations of the present invention comprise at least one active ingredient, as defined above, together with one or more acceptable carriers thereof and optionally other therapeutic agents. Each carrier must be "acceptable" in the sense of being compatible with the other ingredients of the formulation and not injurious to the patient.

Formulations include those suitable for oral, rectal, nasal, topical (including transdermal, buccal and sublingual), vaginal or parenteral (including subcutaneous, intramuscular, intravenous, intradermal, and intravitreal) administration. The formulations may conveniently be presented in unit dosage form and may be prepared by any methods well known in the art of pharmacy. Such methods represent a further feature of the present invention and include the step of bringing into association the active ingredients with the carrier which constitutes one or more accessory ingredients. In general, the formulations are prepared by uniformly and intimately bringing into association the active ingredients with liquid carriers or finely divided solid carriers or both, and then if necessary shaping the product.

The present invention further includes a pharmaceutical formulation as hereinbefore defined wherein a compound of formula (I) or a pharmaceutically acceptable derivative thereof and at least one further therapeutic agent are presented separately from one another as a kit of parts.

Compositions suitable for transdermal administration may be presented as discrete patches adapted to remain in intimate contact with the epidermis of the recipient for a prolonged period of time. Such patches suitably contain the active compound 1) in an optionally buffered, aqueous solution or 2) dissolved and/or dispersed in an adhesive or 3) dispersed in a polymer. A suitable concentration of the active compound is about 1% to 25%, preferably about 3% to 15%. As one particular possibility, the active compound may be delivered from the patch by electrotransport or iontophoresis as generally described in *Pharmaceutical Research* 3 (6), 318 (1986).

Formulations of the present invention suitable for oral administration may be presented as discrete units such as capsules, caplets, cachets or tablets each containing a predetermined amount of the active ingredients; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredients in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface-active or dispersing agent. Molded tablets may be made by molding a mixture of the powdered compound moistened with an inert liquid diluent in a suitable machine. The tablets may optionally be coated or scored and may be formulated so as to provide slow or controlled release of the active ingredients therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredients in a flavored base, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations suitable for vaginal administration may be presented as pessaries, tampons, creams, gels, pastes, foams or spray formulations containing in addition to the active ingredient such carriers as are known in the art to be appropriate.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of the active combination with the softened or melted carrier(s) followed by chilling and shaping in molds.

Formulations for rectal administration may be presented as a suppository with a suitable base comprising, for example, cocoa butter or a salicylate.

Formulations suitable for parenteral administration include aqueous and nonaqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents; and liposomes or other microparticulate systems which are designed to target the compound to blood components or one or more organs. The formulations may be presented in unit-dose or multi-dose sealed containers, for example, ampoules and vials, and may be stored in a freeze-dried (lyophilized) condition requiring only the addition of the sterile liquid carrier, for example water for injection, immediately prior to use. Extemporaneous injection solutions and suspensions may be prepared from sterile powders, granules and tablets of the kind previously described.

Preferred unit dosage formulations are those containing a daily dose or daily subdose of the active ingredients, as hereinbefore recited, or an appropriate fraction thereof.

It should be understood that in addition to the ingredients particularly mentioned above the formulations of this invention may include other agents conventional in the art having regard to the type of formulation in question, for example, those suitable for oral administration may include such further agents as sweeteners, thickeners and flavoring agents.

The following examples are intended for illustration only and are not intended to limit the scope of the invention in any way. "Active ingredient" denotes a compound of formula (I) or multiples thereof or a physiologically functional derivative of any of the aforementioned compounds.

General Procedures

General Procedure I

Synthesis of 2-(alkylamino)-1H-benzimidazoles Using 1-cyclohexyl-3-(2-morpholinoethyl) carbodiimide metho-p-toluenesulfonate as desulfurizing Agent.

The appropriate 1,2-phenylenediamine is combined with the appropriate isothiocyanate (1.0–1.25 mmol/mmol of diamine) and anhydrous pyridine (3–5 mL/mmol of diamine). The resulting mixture is heated to 80° C. for 30 min, then 1-cyclohexyl-3-(2-morpholinoethyl)carbodiimide metho-p-toluenesulfonate (1.1–1.35 mmol/mmol of diamine) is added as a solid in one portion. The resulting mixture is allowed to stir at 80–90° C. for 3–20 h, after which time it is allowed to cool to room temperature. The mixture is then filtered and the solvents removed in vauco. The remaining residue is dissolved in ethyl acetate and is washed with water, saturated, aqueous soudium chloride, dried over magnesium sulfate, filtered and the solvents are removed under reduced pressure. The products can be recrystallized from either 1,4-dioxane or acetonitrile.

General Procedure II

Coupling of 2-(alkylamino)-1H-benzimidazoles with 1,2,3-tri-O-acetyl-5-deoxy-D-ribofuranose The appropriate 2-(alkylamino)1H-benzimidazole was combined with 1,2-dichloroethane (2–3 mL/mmol of benzimidazole) and N,O-bis(trimethylsilyl)acetamide (1–1.25 mmol/mmol of benzimidazole) and the resulting mixture was heated to 80° C. for 30 min. Trimethylsilyl trifluoromethanesulfonate (0.5–0.7 mmol/mmol of benzimidazole) was added and the mixture was allowed to stir at 80° C. for an additional 15 min, after which time 1,2,3-tri-O-acetyl-5-deoxy-D-ribofuranose (1–1.25 mmol/mmol of benzimidazole) was added as a solid in one portion. The resulting mixture was allowed to stir at 80° C. for 2–20 h, after which time it was allowed to cool to room temperature. It was then diluted with 5% aqueous sodium bicarbonate (10 mL/mmol of benzimidazole) and dichloromethane (3–5 mL/mmol of benzimidazole) and the two-phase mixture was stirred at room temperature for 30 min. The organic layer was collected and the aqueous layer was back-extracted with an additional portion of dichloromethane (3–5 mL/mmol of benzimidazole) and the combined organic layers were dried over magnesium sulfate, filtered and the solvents were removed under reduced pressure using a rotary evaporator. The products were further purified by silica gel chromatography.

General Procedure III

Deprotection of 2-(alkylamino)1-(2,3-di-O-acetyl-5-deoxy-beta-D-ribofuranosyl)-1H-benzimidazoles with sodium carbonate in aqueous methanol/ethanol.

The appropriate 2-(alkylamino)-1-(2,3-di-O-acetyl-5-deoxy-beta-D-ribofuranosyl)-1H-benzimidazole was dissolved in ethanol (4–5 mL/ mmol of triacetate). Into a separate flask were placed sodium carbonate (1.0–1.3 mmol/mmol of triacetate), water (1–2 mL/mmol of triacetate), and methanol (3 mL/mmol of triacetate). The sodium carbonate suspension was added to the ethanolic solution of the triacetate at room temperature and in one portion. The resulting mixture was allowed to stir at room temperature for 18 h. The mixture was then diluted with ethyl acetate (25 mL/mmol of triacetate). The organic layer was collected and was washed with saturated aqueous brine (100 mL/mmol of triacetate), dried over magnesium sulfate, filtered, and the solvents were removed by rotary evaporation. The products were further purified by silica gel chromatography.

General Procedure IV

Deprotection of 2-(alkylamino)-1-(2,3-di-O-acetyl-5-deoxy-beta-D-ribofuranosyl)-1H-benzimidazoles with lithium hydroxide in dioxane/water The appropriate 2,3-di-O-acetyl protected nucleoside was dissolved in dioxane (5 mL) and cooled to 0° C. in an ice bath. A 4N solution of LiOH was added dropwise and the resulting mixture was stirred for 30 min at 0° C. To this mixture was then added pH 7 buffer (until neutral) and brine. This mixture was then extracted with ethyl acetate (5×50 mL). The organic layer was dried (MgSO$_4$), filtered, concentrated in vacuo to yield the corresponding deprotected nucleoside.

General Procedure V

Synthesis of 2-alkylamino-1-(5-deoxy-beta-D-ribofuranosyl)-1H-benzimidazoles from 2-bromo-1-(5-deoxy-beta-D-ribofuranosyl)-1H-benzimidazoles.

Amine and 2-bromo-5,6-dichloro-1-(5-deoxy-1-beta-D-ribofuranosyl)-1H-benzimidazole were combined with absolute ethanol (5 mL) in a pressure tube and stirred at 80° C. until the benzimidazole was consumed. The reaction mixture was concentrated, dissolved in ethyl acetate (25 mL) and washed with saturated NaHCO$_3$ (10 mL), followed by water (10 mL). The ethyl acetate layer was dried with magnesium sulfate (anhyd), filtered, and evaporated. The crude residue was purified on a silica gel column.

EXAMPLES

Example 1

5,6-Dichloro-N-(1-methylethyl)-1H-benzimidazol-2-amine 5,6-Dichloro-1,2-phenylenediamine (0.61 g, 3.4 mmol), isopropyl isothiocyanate (0.39 g, 3.8 mmol), dicyclohexyl carbodiimide (1.06 g, 5.14 mmol) and pyridine (10 L) were used according to general procedure I. The product was recrystallized from acetonitrile to afford a tan solid (0.46 g, 60%); m.p. 218–220° C.

Anal. Calcd for $C_{10}H_{11}Cl_2N_3$: C, 49.20; H, 4.54; N, 17.21. Found C, 49.31; H, 4.59; N, 17.33.

Example 2

2-(Cyclopropylamino)5,6-dichloro-1H-benzimidazole 4,5-Dichloro-1,2-phenylenediamine (6.04 g, 34.1 mmol), cyclopropyl isothiocyanate (3.69 g, 37.2 mmol), 1-cyclohexyl-3-(2-morpholinoethyl)carbodiimide metho-p-toluenesulfonate (20.1 g, 47.4 mmol) and pyridine (135 mL) were used according to general procedure I. The product was recrystallized from acetonitrile to afford 5.82 g (70%) of a yellow solid; m.p. 223–225° C. $^1$H NMR (DMSO-$d_6$) δ: 11.2 (s, 1H, NH), 7.43 (s, 1H, NH), 7.27 (s, 2H, ArH), 2.49 (m, 1H, CH), 0.70 (m, 2H, CH), 0.49 (m, 2H, CH).

Anal. Calcd for $C_{10}H_9Cl_2N_3$: C, 49.61; H, 3.75; N, 17.36. Found: C, 49.53; H, 3.78; N, 17.12.

Example 3

2-Bromo-5,6-dichloro-1-(2,3-di-O-acetyl-5-deoxy-beta-D-ribofuranosyl)-1H-benzimidazole 2-Bromo-5,6-dichloro-1H-benzimidazole (5.11 g, 19.21 mmol), and N,O-bis(trimethylsiyl) acetamide (Aldrich, 4.81 mL, 19.21 mmol) were combined with acetonitrile (Aldrich Sure Seal, 100 mL) and refluxed under nitrogen for 3 h. The solution was cooled to rt and trimethylsilyl triflate (Aldrich, 7.70 mL, 38.42 mmol) was added. After 15 min, 5-deoxy-1,2,3-tri-O-acetyl-D-ribofuranose (5.0 g, 19.21 mmol) in acetonitrile (4 mL) was added. The solution was stirred under nitrogen at rt for 3.5 h, then poured into 10% aqueous sodium bicarbonate (300 mL) and extracted with ethyl acetate (3×100 mL). The organic layers were washed with water (1×100 mL), dried with magnesium sulfate (anhyd), filtered, and evaporated. The crude residue was purified on a silica gel column with 1:30 acetone:$CH_2Cl_2$ to give the title compound (6.96 g, 14.93 mmol, 78%); MS (El): m/z (rel. intensity) 489 (0.22, M$^+$+Na); $^1$H NMR (DMSO-$d_6$) δ8.13 (s, 1H, Ar—H), 8.02 (s, 1H, Ar—H), 6.17 (d, 1H, CH, J=6.6 Hz), 5.67 (t, 1H, CH, J=13.9 Hz), 5.29 (t, 1H, CH, J=7.2 Hz), 4.28 (m, 1H, CH), 2.16 (s, 3H, OAc), 2.04 (s, 3H, OAc), 1.53 (d, 3H, $CH_3$, J=6.5 Hz).

Example 4

2-Bromo-5,6-dichloro-1-(5-deoxy-beta-D-ribofuranosyl)-1H-benzimidazole

2-Bromo-5,6-dichloro-1-(2,3-di-O-acetyl-5deoxy-beta-D-ribofuranosyl)-1H-benzimidazole (7.70 g, 16.52 mmol) was dissolved in ethanol (100 mL) and methanol (100 mL). A solution of sodium carbonate (1.75 g, 16.52 mmol) in water (30 mL) was added to the diacetate solution. The resulting mixture was stirred at rt for 17 h. The reaction mixture was concentrated, dissolved in ethyl acetate (125 mL) and extracted with water (3×50 mL). The ethyl acetate layer was dried with magnesium sulfate (anhyd), filtered, and evaporated. The crude residue was purified on a silica gel column with 1:30 methanol:CH—$_2$Cl$_2$. The resulting product was further purified on a silica gel column with 1:2 ethyl acetate: hexanes, followed by 1:1 ethyl acetate:hexanes to give the compound (3.00 g, 7.85 mmol, 48%);

MS (El): m/z (rel. intensity) 405 (0.05, M$^+$+Na); $^1$H NMR (DMSO-$d_6$) δ8.00 (s, 1H, Ar—H), 7.87 (s, 1H, Ar—H), 5.87 (d, 1H, OH, J=6.7 Hz), 5.53 (d, 1H, OH, J=6.2 Hz), 5.29 (d, 1H, CH, J=5.1 Hz), 4.52 (m, 1H, CH), 4.01 (m, 1H, CH), 3.91 (m, 1H, CH), 1.42 (d, 3H, $CH_3$, J=6.5 Hz).

Anal. Calcd. for $C_{12}H_{11}N_2O_3Cl_2Br$: C, 37.73; H, 2.90; N, 7.33. Found: C, 37.62; H, 2.92; N, 7.25.

Example 5

5,6-Difluoro-1-(2,3-di-O-acetyl-5-deoxy-beta-D-ribofuranosyl)-N-(1-methylethyl)-1H-benzimidazol-2-amine A. 4,5-Difluoro-1,2-phenylenediamine Into a Parr bottle were placed 4,5-difluoro-2-nitroaniline (5.00 g, 28.72 mmol), platinum (IV) oxide (0.31 g, 1.13 mmol) and methanol (60 mL). The bottle was flushed three times with hydrogen and was finally pressurized to 45 psig with hydrogen. The bottle was shaken for 5 h, after which time it was depressurized and the contents were poured into a separatory funnel containing ethyl acetate (300 mL) and water (300 mL). The organic layer was collected and washed with saturated aqueous brine solution (100 mL), dried over magnesium sulfate and the solvents were removed under reduced pressure using a rotary evaporator to leave 3.37 g (81%) of a brown solid. MS (Cl): m/z 145 (M+1).

B. 5,6-Difluoro-N-(1-methylethyl)-1H-benzimidazol-2-amine 4,5-Difluoro-1,2-phenylenediamine (2.87 g, 19.91 mmol), isopropyl isothiocyanate (2.19 g, 21.65 mmol), 1-cyclohexyl-3-(2-morpholinoethyl)carbodiimide metho-p-toluenesulfonate (11.38 g, 26.87 mmol) and pyridine (75 mL) were used according to general method I. The product was recrystallized from 1,4-dioxane to afford 2.23 g (53%) of a white solid; m.p. 188–189° C.

Anal. Calcd for $C_{10}H_{11}F_2N_3$: C, 56.87; H, 5.25; N, 19.89. Found: C, 56.95; H, 5.25; N, 19.98.

C. 5,6-Difluoro-1-(2,3-di-O-acetyl-5-deoxy-beta-D-ribofuranosyl)-N-(1-methylethyl)1H-benzimidazol-2-amine 5,6-Difluoro-N-(1-methylethyl)1H-benzimidazol-2-amine (0.24 g, 1.1 mmol), N,O-bis(trimethylsilyl) acetamide (Aldrich, 0.30 mL, 1.2 mmol), and acetonitrile (Aldrich Sure Seal, 40 mL) were combined and refluxed under nitrogen for 15 min. The solution was cooled to room temperature and trimethylsilyl triflate (Aldrich, 0.13 mL, 0.7 mmol) was added. After 10 min, 1,2,3-tri-O-acetyl-5-deoxy-D-ribofuranose (0.38 g, 1.5 mmol) dissolved in acetonitrile (Aldrich Sure Seal, 15 mL) was added. The solution was stirred under nitrogen at rt for 4.5 h and then heated in an 80° C. oil bath for 2 h. The solution was then poured into 5% aqueous sodium bicarbonate (50 mL) and extracted with ethyl acetate (3×100 mL). The organic layers were dried with magnesium sulfate (anhyd), filtered, and evaporated. The crude residue was purified on a silica gel column (2.5×20 cm, 230–400 mesh) with 95:5 dichloromethane-methanol to give the title compound (0.32 g, 0.8 mmol, 71%); $^1$H NMR (DMSO-$d_6$) δ7.40–7.46 (m 1H, Ar—H), 7.21–7.28 (m, 1H, Ar—H), 6.74 (d, 1H, NH, J=7.5 Hz), 6.05 (d, 1H, H-1', J=6.6 Hz), 5.55–5.59 (m, 1H, CH), 5.21–5.25 (m, 1H, CH), 4.00–4.24 (m, 2H, CH), 2.14 (s, 3H, OAc), 2.01 (s, 3H, OAc), 1.49 (d, 3H, 5'-$CH_3$, J=6.3 Hz), 1.20–1.24 (m, 6H, $CH_3$).

Example 6

5,6-Difluoro-1-(5-deoxy-1-beta-D-ribofuranosyl)-N-(1-methylethyl)-1H-benzimidazol-2-amine 5,6-Difluoro-1-(2,3-di-O-acetyl-5-deoxy-beta-D-ribofuranosyl)-N-(1-methylethyl)-1H-benzimidazol-2- amine (0.32 g, 0.8 mmol), methanol (15 mL), ethanol (15 mL), and sodium carbonate (0.26 g, 2.4 mmol) were used according to general procedure III. The crude residue was purified on a silica gel column (5×20 cm, 230–400 mesh) with 2:1 hexane-acetone. Product containing fractions were combined, evaporated and chromatographed on a second silica gel column (2.5×20 cm, 230–400 mesh) with 95:5 $CH_2Cl_2$:methanol to give 5,6-difluoro-2-isopropylamino-1-(5-deoxy-1-beta-D-ribofuranosyl)-1H-benzimidazole (0.16 g, 61%); MS (AP+): m/z 328 (M+1); $^1$H NMR (DMSO-$d_6$) δ: 7.15–7.28 (m, 2H, Ar—H), 6.48 (d, 1H, NH, J=6.9 Hz), 5.68 (d, 1H, H-1', J=6.6 Hz), 5.23–5.26 (b, 2H, OH), 4.35–4.37 (m, 1H, CH), 3.99–4.06 (m, 1H, CH), 3.84–3.91 (m, 2H, CH), 1.39 (d, 3H, 5'-$CH_3$, J=6.3 Hz), 1.23 (d, 6H, $CH_3$, J=6.3 Hz).

Anal. Calcd for $C_{15}H_{19}F_2N_3O_3$·0.25 $C_4H_8O_2$: C, 55.01; H, 6.06; N, 12.03. Found: C, 54.62; H, 5.93; N, 12.17.

Example 7

4,6-Dichloro-N-(1-methylethyl)-1H-benzimidazol-2-amine 3,5-Dichloro-1,2-phenylenediamine (1.30 g, 7.32 mmol), isopropyl isothiocyanate (0.81 g, 8.00 mmol), 1-cyclohexyl-3-(2-morpholinoethyl)carbodiimide metho-p-toluenesulfonate (4.19 g, 9.89 mmol) and pyridine (25 mL) were used according to general procedure I. The product was recrystallized from 1,4-dioxane to afford 1.07 g (60%) of a white solid; $^1$H NMR (DMSO-$d_6$) δ: 10.9 (s, 1H, NH), 7.07 (d, J=1.5 Hz, 1H, ArH), 6.98 (d, J=1.6 Hz, 1H, ArH), 6.92 (d, J=7.9 Hz, 1H, NH), 3.89 (m, 1H, CH), 1.17 (d, J=6.6 Hz, 6H, overlapping $CH_3$).

Anal. calcd for $C_{10}H_{11}Cl_2N_3$-(0.25 $C_4H_8O_2$): C, 49.64; H, 4.92; N, 15.79. Found: C, 49.54; H, 4.94; N, 15.79.

Example 8

4,6-Dichloro-1-(2,3-di-O-acetyl-5-deoxy-beta-D-ribofuranosyl)-N-(1-methylethyl)-1H-benzimidazol-2-amine Starting with 4,6-Dichloro-N-(1-methylethyl)-1H-benzimidazol-2-amine, this reaction was carried out according to general procedure II. Following flash column chromatography on silica gel with MeOH/$CH_2Cl_2$ (1:50), a 19% yield of the title compound was obtained as a single isomer, confirmed by NOE experiments. $^1$H NMR (DMSO-$d_6$) δ1.2 (t, 6H, 2×$CH_3$), 1.4 (d, 3H, $CH_3$), 1.95 (s, 3H, $COCH_3$), 2.08 (s, 3H, $COCH_3$), 4–4.1 (m, 2H, 2×CH), 5.2 (t, 1H, CH), 5.5 (t, 1H, CH), 6 (d, 1H, CH), 6.88 (d, 1H, NH), 7.13 (s, 1H, aromatic), 7.31 (s, 1H, aromatic).

Example 9

4,6-Dichloro-1-(5-deoxy-beta-D-ribofuranosyl)-N-(1-methylethyl)-1H-benzimidazol-2-amine Starting with 4,6-Dichloro-1-(2,3-di-O-acetyl-5-deoxy-beta-D-ribofuranosyl)-N-(1-methylethyl)-1H-benzimidazol-2-amine, this reaction was carried out according to general procedure III. This gave a 73% yield of the title compound as a white solid. $^1$H NMR (DMSO-$d_6$) δ1.2 (d, 6H, 2×$CH_3$), 1.35 (d, 3H, $CH_3$), 3.78–3.8 (m, 1H, CH), 3.82–3.9 (m, 1H, CH), 4.0–4.1 (m, 1H, CH), 4.3 (q, 1H, CH), 5.2–5.25 (m, 2H, 2×OH), 5.65 (d, 1H, CH), 6.6 (d, 1H,NH), 7.1 (s, 1H, aromatic), 7.12 (s, H, aromatic).

Anal. Calc for $C_{15}H_{19}N_3O_3Cl_2$: C, 50.01; H, 5.32; N, 11.66; Cl, 19.68. Found: C, 49.92; H, 5.27; N, 11.56; Cl, 19.74.

Example 10

4,5-Dichloro-N-(1-methylethyl)-1H-benzimidazol-2-amine

A. 3,4-Dichloro-1,2-phenylenediamine 2,3-Dichloro-6-nitroaniline (20.11 g, 97.14 mmol), Raney nickel (Aldrich, Milwaukee, slurry in water, 4.78 g wet), and ethanol (250 mL) were combined in an autoclave which was presssurized to 150 psig with hydrogen. The resulting reaction mixture was allowed to stir at rt overnight. The mixture was then filtered through a pad of Celite, which was subsequently washed with several portions of methanol, and the solvents were removed by rotary evaporation to leave a dark brown solid. The solid was slurried in hexanes and was collected on a Büchner funnel to afford 16.31 g (95%) of a brown solid. MS (EI): m/z 177.0 (M+H); $^1$H NMR (DMSO-$d_6$) δ: 6.60 (d, J=8.3 Hz, 1H, ArH), 6.49 (d, J=8.4 Hz, 1H, ArH), 4.98 (br s, 4H, overlapping $NH_2$).

B. 4,5-Dichloro-N-(1-methylethyl)-1H-benzimidazol-2-amine 3,4-Dichloro-1,2-phenylenediamine (8.00 g, 45.19 mmol), isopropyl isothiocyanate (5.26 g, 51.99 mmol), 1-cyclohexyl-3-(2-morpholinoethyl)carbodiimide metho-p-toluenesulfonate (25.0, 59.02 mmol), and pyridine (250 mL) were used according to general procedure I. The product was recrystallized from 1,4-dioxane to afford 6.12 g (55%) of a white solid. MS (EI): m/z 244 (M+H); $^1$H NMR (DMSO-$d_6$) δ: 11.08 (s, 1H, NH), 7.07 (d, J=8.3Hz, 1H, ArH), 7.00 (brs, 1H, NH), 6.99 (d, J=8.3Hz, 1H, ArH), 3.91 (m, 1H, CH), 1.21 (d, J=6.5 Hz, 6H, overlapping $CH_3$).

Anal. calcd for $C_{10}H_{11}Cl_2N_3$-(0.35 $C_4H_8O_2$): C, 49.80; H, 5.06; N, 15.28 Found: C, 49.95; H, 5.05; N, 15.08.

Example 11

4,5-Dichloro-1-(2,3-di-O-acetyl-5-deoxy-beta-D-ribofuranosyl)-N-(1-methylethyl)1H-benzimidazol-2-amine 4,5-Dichloro-N-(1-methylethyl)-1H-benzimidazol-2-amine (0.50 g, 2.0 mmol), N,O-bis(trimethylsilyl) acetamide (Aldrich, 0.55 mL, 2.2 mmol), and acetonitrile (Aldrich Sure Seal, 70 mL) were combined and refluxed under nitrogen for 15 min. The solution was cooled to rt and trimethylsilyl trifluoromethanesulfonate (Aldrich, 0.24 mL, 1.2 mmol) was added. After 10 min, 1,2,3-tri-O-acetyl-5-deoxy-D-ribofuranose (0.69 g, 2.6 mmol) dissolved in acetonitrile (Aldrich Sure Seal, 10 mL) was added. The solution was stirred under nitrogen at rt for 12 h and then heated in an 80° C. oil bath for 2.5 h. The solution was then poured into 5% aqueous sodium bicarbonate (50 mL) and extracted with ethyl acetate (3×100 mL). The organic layers were dried with magnesium sulfate, filtered, and evaporated. The crude residue was purified on a silica gel column (2.5×20 cm, 230–400 mesh) with 97:3 dichloromethane-methanol to give the title compound (0.82 g, 1.8 mmol, 90%); $^1$H NMR (DMSO-$d_6$) δ: 7.29 (s, 1H, Ar—H, J=8.4 Hz), 7.10 (s, 1H, Ar—H, J=8.4 Hz), 6.98 (d, 1H, NH, J=7.5 Hz), 6.10 (d, 1H, H-1', J=6.3 Hz), 5.50–5.55 (m, 1H, CH), 5.15 (t, 1H, CH, J=6.0 Hz), 4.04–4.17 (m, 2H, CH), 2.14 (s, 3H, OAc), 2.01 (s, 3H, OAc), 1.48 (d, 3H, 5'-$CH_3$, J=6.3 Hz), 1.24 (t, 6H, $CH_3$, J=6.2 Hz).

Example 12

4,5-Dichloro-1-(5deoxy-beta-D-ribofuranosyl)-N-(1-methylethyl)-1H-benzimidazol-2-amine 4,5-Dichloro-1-(2,3-di-O-acetyl-5-deoxy-beta-D-ribofuranosyl)-N-(1-methylethyl)-1H-benzimidazol-2- amine (0.82 g, 1.8 mmol) was dissolved in 1,4dioxane (Aldrich, 20 mL). Aqueous lithium hydroxide (5.5 mL, 1.0 M, 5.5 mmol) was added and the mixture was stirred for 30 min. The solution was then diluted with brine (50 mL) and extracted with ethyl acetate (3×50 mL). The organic layers were dried over magnesium sulfate, filtered, and evaporated. The crude residue was purified on a silica gel column (5×20 cm, 230–400 mesh) with 96:4 dichloromethane-methanol to give the title compound (0.48 g, 1.3 mmol, 72%); MS (AP+): m/z 360 (M+1); $^1$H NMR (DMSO-d$_6$) δ: 7.11 (d, 1H, Ar—H, J=8.7 Hz), 7.04 (d, 1H, Ar—H, J=8.4 Hz), 6.75 (d, 1H, NH, J=7.5 Hz), 5.70 (d, 1H, H-1', J=6.3 Hz), 5.27 (d, 1H, OH, J=6.6 Hz), 5.22 (d, 1H, OH, J=4.8 Hz), 4.28–4.35 (m, 1H, CH), 4.05–4.16 (m, 1H, CH), 3.77–3.92 (m, 2H, CH), 1.35 (d, 3H, 5'-CH$_3$, J=6.6 Hz), 1.22 (d, 6H, CH$_3$, J=6.6 Hz).

Anal. Calcd for C$_{15}$H$_{19}$Cl$_2$N$_3$O$_3$: C, 50.01; H, 5.32; N, 11.66; Cl, 19.68. Found: C, 50.22; H, 5.39; N, 11.59; Cl, 19.60.

Example 13

5-Cyano-N-(1-methylethyl)-1H-benzimidazol-2-amine

4-Cyano-1,2-phenylenediamine (prepared according to the method of Fairley, T. A., et.al. J. Med. Chem. 1993, 36, 1746, 3.7 g, 27.8 mmol), isopropyl isothiocyanate (3.3 g, 32.7 mmol), 1-cyclohexyl-3-(2-morpholinoethyl)carbodiimide metho-p-toluenesulfonate (16.0 g, 37.8 mmol) and pyridine (200 mL) were used according to general procedure I. The title compound was recrystallized from 1,4-dioxane to provide a tan powder (2.2 g, 40%); m.p. 185–190° C.; $^1$H NMR (DMSO-d$_6$) δ: 11.0 (br s, 1H, NH), 7.44 (s, 1H, Ar—H), 7.2–7.1 (m, 2H, Ar—H), 6.95 (br s, 1H, NH), 3.88 (m, 1H, CH), 1.16 (d, J=6.5 Hz, 6H, overlapping CH$_3$).

Anal. Calcd for C$_{11}$H$_{12}$N$_4$-(0.44 C$_4$H$_8$O$_2$): C, 64.12; H, 6.55; N, 23.44. Found: C, 63.84; H, 6.55; N, 23.80.

Example 14

5-Cyano-1-(2,3-di-O-acetyl-5deoxy-β-D-ribofuranosyl)-N-(1-methylethyl)-1H-benzimidazol-2-amine and 6-cyano-1-(2,3-di-O-acetyl-5-deoxy-β-D-ribofuranosyl)-N-(1-methylethyl)-1H-benzimidazol-2-amine Starting with 5-Cyano-N-(1-methylethyl)-1H-benzimidazol-2-amine, this reaction was carried out according to general procedure II, except in this case acetonitrile was used as the reaction solvent. Flash column chromatography on silica with EtOAc/hexane (1:1) gave first a 7% yield of an oil identified as 5-Cyano-1-(2,3-di-O-acetyl-5-deoxy-β-D-ribofuranosyl)-N-(1-methylethyl)1H-benzimidazol-2-amine by NOE experiments. Further elution resulted in an 8% yield of 6-cyano-1-(2,3-di-O-acetyl-5-deoxy-β-D-ribofuranosyl)-N-(1-methylethyl)-1H-benzimidazol-2-amine as an oil, also confirmed by NOE experiments. $^1$H NMR for 5-Cyano-1-(2,3-di-O-acetyl-5-deoxy-β-D-ribofuranosyl)-N-(1-methylethyl)-1H-benzimidazol-2-amine (DMSO-d$_6$) δ1.18 (t, 6H, 2×CH$_3$), 1.4 (d, 3H, CH$_3$), 1,95 (s, 3H, COCH$_3$), 2.08 (s, 3H, COCH$_3$), 3.9–4.1 (m, 2H, 2×CH), 5.1 (t, 1H, CH), 5.5 (t, 1H, CH), 6.07 (d, 1H, CH), 6.9 (d, 1H, NH), 7.3 (d, 1H, aromatic), 7.4 (d, 1H, aromatic), 7.6 (s, 1H, aromatic).

$^1$H NMR for 6-cyano-1-(2,3-di-O-acetyl-5-deoxy-β-D-ribofuranosyl)-N-(1-methylethyl)-1H-benzimidazol-2-amine (DMSO-d$_6$) δ1.18 (t, 6H, 2×CH$_3$), 1.45 (d, 3H, CH$_3$), 1,95 (s, 3H, COCH$_3$), 2.08 (s, 3H, COCH$_3$), 4–4.1 (m, 2H, 2×CH), 5.24 (t, 1H, CH), 5.58 (t, 1H, CH), 6.05 (d, 1H, CH), 7.06 (d, 1H, NH), 7.26 (d, 1H, aromatic), 7.4 (d, 1H, aromatic), 7.8 (s, 1H, aromatic).

Example 15

5-Cyano-1-(5-deoxy-β-D-ribofuranosyl)-N-(1methylethyl)-1H-benzimidazol-2-amine

Starting with 5-Cyano-1-(2,3di-O-acetyl-5-deoxy-β-D-ribofuranosyl)-N-(1methylethyl)-1H-benzimidazol-2-amine, this reaction was carried out according to general procedure Ill. Following purification on silica gel preparative plate with EtOAc/hexane (7:3), a 42% yield of the title compound was obtained. $^1$H NMR (DMSO-d$_6$) δ1.19 (d, 6H, 2×CH$_3$), 1.33 (d, 3H, CH$_3$), 3.75–3.8 (m, 1H, CH), 3.8–3.9 (m, 1H, CH), 3.9–4.1 (m, 1H, CH), 4.3 (q, 1H, CH), 5.2 (d, 1H, CH), 5.25 (d, 1H, CH), 5.7 (d, 1H, CH), 6.7 (d, 1H, NH), 7.2–7.3 (m, 2H, aromatic), 7.6 (s, 1H, aromatic).

Anal. Calc for C$_{16}$H$_{20}$N$_4$O$_3$: C, 60.75; H, 6.37; N, 17.71. Found: C, 60.65; H, 6.47; N, 17.44.

Example 16

6-Cyano-1-(5-deoxy-β-D-ribofuranosyl)-N-(1methylethyl)-1H-benzimidazol-2-amine

Starting with 6-Cyano-1-(5-deoxy-β-D-ribofuranosyl)-N-(1 methylethyl)-1H-benzimidazol-2-amine, this reaction was carried out according to general procedure II. Following purification on silica gel preparative plate with EtOAc/hexane (7:3) as the eluent, a 25% yield of the title compound was obtained. $^1$H NMR (DMSO-d$_6$) δ1.19 (d, 6H, 2×CH$_3$), 1.33 (d, 3H, CH$_3$), 3.75–3.8 (m, 1H, CH), 3.8–3.9 (m, 1H, CH), 3.9–4.1 (m, 1H, CH), 4.39 (q, 1H, CH), 5.2 (d, 2H, 2×OH), 5.7 (d, 1H, CH), 6.8 (d, 1H, NH), 7.27(d, 1H, aromatic), 7.37 (d, 1H, aromatic), 7.5 (s, 1H, aromatic).

Anal. Calc for C$_{16}$H$_{20}$N$_4$O$_3$0.4EtOAc: C, 60.12; H, 6.65; N, 15.93. Found: C, 60.26; H, 6.82; N, 15.91.

Example 17

4,5,6-Trifluoro-N-(1-methylethyl)-1H-benzimidazol-2-amine

A. 3,4,5-Trifluoro-1,2-phenylenediamine 1,2,3-Trifluoro-6-nitroaniline (15.0 g, 78.1 mmol, Aldrich, Milwaukee), Raney nickel (Aldrich, Milwaukee, slurry in water, 1.0 g wet) and ethanol (100 mL) were placed in a Parr reactor which was pressurized with hydrogen (175 psig) and stirred. The resulting mixture was allowed to stir overnight at rt, after which time it was filtered through Celite and the solvents were removed in vacuo to provide a dark oil. The title compound was purified by silica gel chromatography using 3:2 hexane-ethyl acetate as eluent to provide a brown solid (9.6 g, 76%); $^1$H NMR (DMSO-d$_6$) δ: 6.30 (m, 1 H, Ar—H), 4,91 (br s, 2H, NH$_2$), 4.52 (br s, 2H, NH$_2$).

B. 4,5,6-Trifluoro-N-(1-methylethyl)-1H-benzimidazol-2-amine 3,4,5-Trifluoro-1,2-phenylenediamine (6.0 g, 31.2 mmol), isopropyl isothiocyanate (3.6 g, 35.6 mmol), 1-cyclohexyl-3-(2-morpholinoethyl)carbodiimide metho-p-toluenesulfonate (17.0 g, 40.1 mmol) and pyridine (225 mL) were used according to general procedure I. The title compound was recrystallized from 1,4-dioxane to provide a white solid (4.07 g, 57%); m.p. 182–184° C.; $^1$H NMR (DMSO-d$_6$) δ: 10.97 (br s, 1H, NH), 7.01 (m, 1H, Ar—H), 6.80 (br s, 1H, NH), 3.91 (m, 1H, CH), 1.20 (d, J=6.4 Hz, 6H, overlapping CH$_3$).

Anal. Calcd for C$_{10}$H$_{10}$F$_3$N$_3$: C, 52.4; H, 4.4; N, 18.33. Found C, 52.5; H, 4.43; N, 18.38.

Example 18

4,5,6-Trifluoro-1-(2,3-di-O-acetyl-5-deoxy-beta-D-ribofuranosyl N-(1-methylethyl)-1H-benzimidazol-2-amine and 5,6,7-Trifluoro-1-(2,3-di-O-acetyl-5-deoxy-beta-D-ribofuranosyl)-N-(1-methylethyl)-1H-benzimidazol-2-amine 4,5,6-Trifluoro-N-(1-methylethyl)-1H-benzimidazol-2-amine (0.60 g, 2.62 mmol), N,O-bis(trimethylsilyl) acetamide (0.72 mL, 0.59 g, 2.91 mmol), trimethylsilyl trifluromethanesulfonate (0.36 mL, 0.43 g, 0.69 mmol), 1,2,3-tri-O-acetyl-5-deoxy-D-ribofuranose (0.88 g, 3.38 mmol) and 1,2-dichloroethane (30 mL) were used according to general procedure II. The title compounds were purified by silica gel chromatography using 95:5 dichloromethane-acetonitrile as eluent to provide 4,5,6-Trifluoro-1-(2,3-di-O-acetyl-5-deoxy-beta-D-ribofuranosyl)-N-(1-methylethyly)-1H-benzimidazol-2-amine as a white foam (0.42 g, 39%); $^1$H NMR (DMSO-d$_6$) δ: 7.29 (m, 1H, Ar—H), 7.27 (d, J=7.5 Hz, NH), 6.01 (d, J=6.8 Hz, 1H, CH), 5.50 (t, J=&.2 Hz, 1H, CH), 5.18 (dd, J=7.2, 5.7 Hz, 1H, CH), 4.05 (m, 2H, overlapping CH), 2.08 (s, 3H, CH$_3$), 2.04 (s, 3H, CH$_3$), 1.43 (d, J=6.3 Hz, CH$_3$), 1.17 (apparent t, 6H, overlapping CH$_3$); mass spectrum(CI): 430 (M+1). Silica gel chromatography also provided 5,6,7-Trifluoro-1-(2,3-di-O-acetyl-5-deoxy-beta-D-ribofuranosyly)-N-(1-methylethyl)-1H-benzimidazol-2-amine as a white solid (0.41 g, 38%); $^1$H NMR (DMSO-d$_6$) δ: 7.11 (m, 1H, Ar—H), 6.9 (d, J=7.5 Hz, 1H, NH), 6.03 (d, J=5.1 Hz, 1H, CH), 5.27 (t, J=6.9 Hz, 1H, CH), 4.91 (t, J=7.2 Hz, 1H, CH), 4.0 (m, 2H, overlapping CH), 2.08 (s, 3H, CH$_3$), 2.04 (s, 3H, CH$_3$), 1.98 (s, 3H, CH$_3$), 1.36 (d, J=6.4 Hz, 3H, CH$_3$), 1.17 (apparent t, 6H, overlapping CH$_3$).

Example 19

4,5,6-Trifluoro-1-(5-deoxy-beta-D-ribofuranosyl)-N-(1-methylethyl)-1H-benzimidazol-2-amine 4,5,6-Trifluoro-1-(2,3-di-O-acetyl-5-deoxy-beta-D-ribofuranosyl)-N-(1-methylethyl)-1H-benzimidazol-2-amine (0.42 g, 1.02 mmol), ethanol (10 mL), sodium carbonate (0.19 g, 1.79 mmol), water (2 mL) and methanol (5 mL) were used according to general procedure III. The title compound was purified by silica gel chromatography using 10:1 dichloromethane-methanol as eluant to provide a white solid (0.26 g, 75%); m.p. 148–151° C.; $^1$H NMR (DMSO-d$_6$) δ: 7.10 (m, 1H, Ar—H), 6.68 (d, J=7.5 Hz, NH), 5.70 (d, J=6.7 Hz, 1H, CH), 5.27 (m, 2H, overlapping OH), 4.35 (dd, J=6.6 Hz, 1H, CH), 4.12 (m, 1H, CH), 3.91 (m, 1H, CH), 3.85 (m, 1H, CH), 1.40 (d, J=6.5 Hz, 3H, CH$_3$), 1.24 (d, J=6.4 Hz, 6H, overlapping CH$_3$).

Anal. Calcd for C$_{15}$H$_{18}$F$_3$N$_3$O$_3$:C, 52.17; H, 5.25; N, 12.17. Found C, 52.25; H, 5.23; N, 12.07.

Example 20

5,6,7-Trifluoro-1-(5-deoxy-beta-D-ribofuranosyl)-N-(1-methylethyl)1H-benzimidazol-2-amine 5,6,7-Trifluoro-1-(2,3-di-O-acetyl-5-deoxy-beta-D-ribofuranosyl)-N-(1-methylethyl)-1H-benzimidazol-2-amine (0.41 g, 0.99 mmol), ethanol (10 mL), sodium carbonate (0.19 g, 1.79 mmol), water (2 mL), and methanol (5 mL) were used according to general procedure III. The title compound was purified by silica gel chromatography using 10:1 dichlormethane-methanol as eluant to provide a white solid (0.16 g, 47%); m.p. 175–178° C.: $^1$H NMR (DMSO-d$_6$) δ: 7.17 (m, 1H, Ar—H), 6.78 (d, J=7.4, Hz, 1H, NH), 5.69 (dd, J=6.3, 1.8 Hz, 1H, CH), 5.26 (d, J=6.5 Hz, 1H, OH), 5.21 (d, J=5.2 Hz, 1H, OH), 4.15 (m, 1H, CH), 4.07 (m, 1H, CH), 3.86–3.74 (m, 2H, overlapping CH), 1.34 (d, J=6.3 Hz, 3H, CH$_3$), 1.23 (d, J=6.5 Hz, 6H, overlapping CH$_3$).

Anal. Calcd. for C$_{15}$H$_{18}$F$_3$N$_3$O$_3$; C, 52.17; H, 5.25; N, 12.17. Found: C, 52.15; H, 5.22; N, 12.07.

Example 21

6-Chloro-4,5-difluoro-N-(1-methylethyl)-1H-benzimidazol-2-amine

A. 2,3-Difluoro-6-nitroaniline 1,2,3-Trifluoronitrobenzene (20.2 g, 114.1 mmol, Aldrich, Milwaukee) and methanolic ammonia (150 mL of a 2.0 molar solution, Aldrich, Milwaukee) were placed in a sealed tube and were heated to 70° C. for 2 h, after which time the solvents were removed in vacuo. The remaining residue was dissolved in ethyl acetate and was extracted with water, saturated aqueous sodium chloride, dried over magnesium sulfate, filtered and the solvents were removed in vacuo to leave a yellow solid. The title compound was recrystallized from water-methanol to afford yellow needles (16.6 g, 84%); $^1$H NMR (DMSO-d$_6$) δ: 7.94 (m, 1H, Ar—H), 7.56 (br s, 2H, NH$_2$), 6.72 (m, 1H, Ar—H).

B. 4-Chloro-2,3-difluoro-6-nitroaniline 2,3-Difluoro-6-nitroaniline (15.4 g, 88.7 mmol), N-chlorosuccinimide (14.9 g, 111.4 mmol) and N,N-dimethylformamide (250 mL) were combined and were heated to 80–90° C. for several hours, after which time the mixture was poured into ice water. The product was extracted with ethyl acetate which was then washed with water, saturated aqueous sodium chloride, dried over magnesium sulfate, filtered and the solvents were removed in vacuo to leave a yellow, viscous oil. $^1$H NMR (DMSO-d$_6$) δ: 8.03 (dd, J=7.3, 2.2 Hz, 1H, Ar—H), 7.65 (br s, 2H, NH$_2$).

C. 5-Chloro-3,4-difluoro-1,2-phenylenediamine

4-Chloro-2,3-difluoro-6-nitroaniline (11.4 g, 54.4. mmol), Raney nickel (Aldrich, Milwaukee, slurry in water, 2.2 g wet) and ethanol (200 mL) were combined in a stirred Parr reactor which was pressurized with hydrogen (250 psig). The mixture was allowed to stir at rt overnight, after which time the reactor was depressurized and the mixture was filtered through Celite and the solvents were removed in vacuo. The remaining residue was dissolved in ethyl acetate, dried over magnesium sulfate and the solvents were removed in vacuo to afford a brownish solid (11.6 g, crude weight); $^1$H NMR (DMSO-d$_6$) δ: 6.43 (d, J=5.7 Hz, 1H, Ar—H), 5.25 (very br s, 4H, overlapping NH$_2$).

D. 6-Chloro-4,5-difluoro-N-(1-methylethyl)-1H-benzimidazol-2-amine

5-Chloro-3,4difluoro-1,2-phenylenediamine (11.6 g, crude material), isopropyl isothiocyanate (6.3 g, 62.1 mmol), 1-cyclohexyl-3-(2-morpholinoethyl)carbodiimide metho-p-toluenesulfonate (28.0 g, 66.2 mmol) and pyridine (250 mL) were used according to general procedure I. The title compound was recrystallized from 1,4-dioxane to provide a tan solid (3.2 g, 25%); m.p. 175–178° C.; $^1$H NMR (DMSO-d$_6$) δ: 11.0 (br s, 1H, NH), 7.07 (d, J=5.4 Hz, 1H, Ar—H), 6.96 (br s, 1H, NH), 3.93 (m, 1H, CH), 1.23 (d,

Example 22

6-Chloro-4,5-difluoro-1-(2,3-di-O-acetyl-5-deoxy-1-beta-D-ribofuranosyl)-N-(1-methylethyl)-1H-benzimidazol-2-amine 6-Chloro-4,5-difluoro-N-(1-methylethyl)-1H-benzimidazol-2-amine (1.0 g, 4.1 mmol), N,O-bis(trimethylsilyl)acetamide (1.1 mL, 0.9 g, 4.5 mmol), trimethylsilyl trifluoromethanesulfonate (0.5 mL, 0.6 g, 2.6 mmol), 1,2,3-tri-O-acetyl-5-deoxy-ribofuranose (1.5 g, 5.7 mmol) and 1,2-dichloroethane (25 mL) were used according to general procedure II. The title compound was purified by silica gel chromatography using 95:5 dichloromethane-acetonitrile as eluant to provide a white foam (0.72 g, 40%); $^1$H NMR (DMSO-$d_6$) δ: 7.37 (d, J=5.6 Hz, 1H, Ar—H), 7.04 (d, J=7.5 Hz, 1H, NH), 6.08 (d, J=6.8 Hz, 1H, CH), 5.57 (t, J=7.1 Hz, 1H, CH), 5.24 (t, J=7.4 Hz, 1H, CH), 4.10 (m, 2H, overlapping CH), 2.14 (s, 3H, CH$_3$), 2.01 (s, 3H, CH$_3$), 1.49 (d, J=6.3 Hz, 3H, CH$_3$), 1.23 (m, 6H, overlapping CH$_3$).

Example 23

6-Chloro-4,5-difluoro-1-(5-deoxy-1-beta-D-ribofuranosyl)-N-(1-methylethyl)-1H-benzimidazol-2-amine 6-Chloro-4,5-difluoro-1-(2,3-di-O-acetyl-5-deoxy-1-beta-D-ribofuranosyl)-N-(1-methylethyl)-1H-benzimidazol-2-amine (0.72 g, 1.67 mmol), ethanol (10 mL), sodium carbonate (0.27 g, 2.55 mmol), water (2 mL) and methanol (5 mL) were used according to general procedure III. The title compound was purified by silica gel chromatography using 10:1 dichloromethane-methanol to afford a white solid (0.26 g, 43%); m.p. 176–178° C.; $^1$H NMR (DMSO-$d_6$) δ: 7.14 (dd, J=5.6, 1.2 Hz, 1H, Ar—H), 6.80 (d, J=7.4 Hz, 1H, NH), 5.72 (d, J=6.9 Hz, 1H, CH), 5.30 (m, 2H, overlapping OH), 4.37 (q, J=6.7 Hz, 1H, CH), 4.06 (m, 1H, CH), 3.95 (m, 1H, CH), 3.85 (m, 1H, CH), 1.40 (d, J=6.4 Hz, 3H, CH$_3$), 1.24 (d, J=6.4 Hz, 6H, overlapping CH$_3$);

Anal. Calcd. for $C_{15}H_{18}ClF_2N_3O_3$: C, 49.80; H, 5.01; N, 11.61. Found C, 49.70; H, 4.99; N, 11.50.

Example 24

5,6-Dichloro-4-fluoro-N-(1-methylethyl)-1H-benzimidazol-2-amine

A. 3,4-Dichloro-2-fluoro-6-nitroaniline 4,5-Dichloro-2-nitroaniline (9.8 g, 47.4 mmol), 1-fluoro-4-hydroxy-1,4-diazoniabicyclo[2.2.2]octane bis(tetrafluoroborate) (18.5 g, 57.4 mmol, Allied Signal, Buffalo), and acetonitrile (300 mL) were combined and the mixture was heated to reflux for several hours. After thin-layer chromatography showed that no starting aniline remained, the mixture was allowed to cool to rt and was poured into ethyl acetate, causing a precipitate to form. The mixture was filtered through a pad of Celite, purified by silica gel and the solvents were removed in vacuo to provide a brown solid (3.9 g, 37%); $^1$H NMR (DMSO-$d_6$) δ: 8.11 (d, J=2.2 Hz, 1H, Ar—H), 7.67 (br s, 2H, NH$_2$).

B. 4-5-Dichloro-3-fluoro-1,2-phenylenediamine 3,4-Dichloro-2-fluoro-6-nitroaniline (6.25 g, 27.78 mmol), Raney nickel (Aldrich, Milwaukee, slurry in water, 1.02 g wet) and ethanol (225 mL) were placed in a stirred Parr reactor which was pressurized with hydrogen (200 psig) and stirred. The mixture was allowed to stir at rt overnight, after which time the reactor was depressurized and the mixture was filtered through Celite and the solvents were removed in vacuo to provide a dark, brown solid (5.23 g, 96%); $^1$H NMR (DMSO-$d_6$) δ: 6.57 (d, J=1.6 Hz, 1H, Ar—H), 5.05 (br s, 4H, overlapping NH$_2$).

C. 5,6-Dichloro-4-fluoro-N-(1-methylethyl)-1H-benzimidazol-2-amine 4,5-Dichloro-3-fluoro-1,2-phenylenediamine (3.37 g, 17.28 mmol), isopropyl isothiocyanate (2.10 g, 20.76 mmol), 1-cyclohexyl-3-(2-morpholinoethyl)carbodiimide metho-p-toluenesulfonate (9.52 g, 22.48 mmol) and pyridine (100 mL) were used according to general procedure I. The title compound was recrystallized from 1,4-dioxane to provide a tan solid (1.40 g, 31%); m.p. 212–215° C.; $^1$H NMR (DMSO-$d_6$) δ: 11.15 (br s, 1H, NH), 7.21 (s, 1H, Ar—H), 6.99 (d, J=7.8 Hz, 1H, NH), 3.92 (m, 1H, CH), 1.21 (d, J=6.4 Hz, 6H, overlapping CH$_3$).

Anal. Calcd. for $C_{10}H_{10}FCl_2N_3$-(0.35 $C_4H_8O_2$): C, 46.74; H, 4.40; N, 14.34. Found: C, 46.66; H, 4.38; N, 14.26.

Example 25

5,6-Dichloro-4-fluoro-1-(2,3-di-O-acetyl-5-deoxy-beta-D-ribofuranosyl)-N-(1-methylethyl)-1H-benzimidazol-2-amine and 5,6-Dichloro-7-fluoro-1-(2,3-di-O-acetyl-5-deoxy-beta-D-ribofuranosyl)-N-(1-methylethyl)-1H-benzimidazol-2-amine 5,6-Dichloro-4-fluoro-N-(1-methylethyl)-1H-benzimidazol-2-amine (0.85 g, 3.24 mmol), N,O-bis(trimethylsilyl)acetamide (0.89 mL, 0.73 g, 3.60 mmol), trimethylsilyl trifluromethanesulfonate (0.45 mL, 0.53 g, 2.25 mmol), 1,2,3-tri-O-acetyl-5-deoxy-ribofuranose (1.15 g, 4.42 mmol) and 1,2-dichloroethane were used according to general procedure II. The title compounds were purified by silica gel chromatography using 95:5 dichloromethane-acetonitrile to first provide 5,6-dichloro-4-fluoro-1-(2,3-di-O-acetyl-5-deoxy-beta-D-ribofuranosyl)-N-(1-methylethyl)-1H-benzimidazol-2-amine as a white foam (0.66 g, 44%); $^1$H NMR (DMSO-$d_6$) δ: 7.49 (s, 1H, Ar—H), 7.05 (d, J=7.4 Hz, 1H, NH), 6.09 (d, J=6.8 Hz, 1H, CH), 5.57 (t, J=7.2 Hz, 1H, CH), 5.24 (dd, J=7.4, 5.3 Hz, 1H, CH), 4.12 (m, 2H, overlapping CH), 2.14 (s, 3H, CH$_3$), 2.01 (s, 3H, CH$_3$), 1.49 (d, J=6.3 Hz, CH$_3$), 1.24 (m, 6H, overlapping CH$_3$). The second fraction provided 5,6-dichloro-7-fluoro-1-(2,3-di-O-acetyl-5-deoxy-beta-D-ribofuranosyl)-N-(1-methylethyl)-1H-benzimidazol-2-amine as a white foam (0.39 g, 26%); $^1$H NMR (DMSO-$d_6$) δ: 7.37 (s, 1H, Ar—H), 7.12 (d, J=7.4 Hz, 1H, NH), 6.08 (d, J=5.4 Hz, 1H, CH), 5.32 (t, J=6.8 Hz, 1H, CH), 4.98 (t, J=7.3 Hz, 1H, CH), 4.10 (m, 2H, overlapping CH), 2.10 (s, 3H, CH$_3$), 2.04 (s, 3H, CH$_3$), 1.41 (d, J=6.2 Hz, CH$_3$), 1.23 (m, 6H, overlapping CH$_3$).

Example 26

5,6-Dichloro-4-fluoro-1-(5-deoxy-1-beta-D-ribofuranosyl)-N-(1-methylethyl)-1H-benzimidazol-2-amine 5,6-Dichloro-4-fluoro-1-(2,3-di-O-acetyl-5-deoxy-beta-D-ribofuranosyl)-N-(1-methylethyl)-1H-benzimidazol-2-amine (0.66 g, 1.43 mmol), ethanol (15 mL), sodium carbonate (0.23 g, 2.17 mmol), water (4 mL) and methanol (5 mL) were used according to general procedure III. The title compound was purified by silica gel chromatography using 10:1 dichloromethane-methanol to provide a white solid (0.27 g, 50%); m.p. 170–177° C.; $^1$H NMR (DMSO-$d_6$) δ: 7.22 (s, 1H, Ar—H), 6.74 (d, J=7.5 Hz, 1H, NH), 5.67 (d, J=6.7 Hz, 1H, CH), 5.26 (m, 2H, overlapping OH), 4.30 (q, J=6.6 Hz, 1H, CH), 4.04 (m, 1H, CH), 3.90 (m, 1H, CH), 3.77 (m, 1H, CH), 1.34 (d, J=6.5 Hz, 3H, $CH_3$), 1.19 (d, J=6.5 Hz, 6H, overlapping $CH_3$).

Anal. Calcd. for $C_{15}H_{18}Cl_2FN_3O_3$: C, 47.63; H, 4.80; N, 11.11. Found: C, 47.44; H, 4.72; N, 10.97.

Example 27

5,6-Dichloro-7-fluoro-1-(5-deoxy-1-beta-D-ribofuranosyl)-N-(1-methylethyl)-1H-benzimidazol-2-amine 5,6-Dichloro-7-fluoro-1-(2,3-di-O-acetyl-5-deoxy-beta-D-ribofuranosyl )-N-(1-methylethyl)-1H-benzimidazol-2-amine (0.39 g, 0.84 mmol), ethanol (15 mL), sodium carbonate (0.14 g, 1.27 mmmol), water (3 mL) and methanol (5 mL) were used according to general procedure III. The title compound was purified by silica gel chromatography using 10:1 dichloromethane-methanol to afford a white solid (0.14 g, 44%); m.p. 170–176° C.; $^1$H NMR (DMSO-$d_6$) δ: 7.31 (s, 1H, Ar—H), 6.86 (d, J=7.6 Hz, 1H, NH), 5.66 (d, J=6.1 Hz, 1H, CH), 5.22 (d, J=6.5 Hz, 1H, OH), 5.15 (d, J=5.1 Hz, 1H, OH), 4.09 (m, 1H, CH), 4.01 (m, 1H, CH), 3.78 (m, 1H, CH), 3.71 (m, 1H, CH), 1.29 (d, J=6.3 Hz, 3H, $CH_3$), 1.18 (d, J=6.5 Hz, 6H, overlapping $CH_3$).

Anal. Calcd. for $C_{15}H_{18}Cl_2FN_3O_3$: C, 47.63; H, 4.80; N, 11.11. Found: C, 47.55; H, 4.77; N, 10.95.

Examples 28

6-Chloro-5-fluoro-1-(2,3-di-O-acetyl-5-deoxy-beta-D-ribofuranosyl)-N-(1-methylethyl)-1H-benzimidazol-2-amine and 5-chloro-6-fluoro-1-(2,3-di-O-acetyl-5-deoxy-beta-D-ribofuranosyl )-N-(1-methylethyl)-1H-benzimidazol-2-amine 6-Chloro-5-fluoro-N-(1-methylethyl)-1H-benzimidazol-2-amine was coupled to 1,2,3-tri-O-acetyl-5-deoxy-D-ribofuranose according to General Procedure II. The crude product was chromatographed (1:1 ethyl acetate:hexanes) to yield 3.0 g of the title compound (83%) as a mix (~1:1) of regioisomers which was found to be contaminated with alpha anomer; $^1$H NMR (DMSO-$d_6$) δ: 7.1–7.5 (m, 2H), 6.87 (d, 0.5H), 6.79 (d, 0.5H), 6.06 (m, 1H), 5.58 (t, 1H), 5.23 (t, 1H), 4.05 (m, 2H), 2.14 (s, 3H), 2.01 (s, 3H), 1.49 (d, 3H), 1.22 (m, 6H).

Example 29

6-Chloro-5-fluoro-1-(5-deoxy-beta-D-ribofuranosyl)-N-(1-methylethyl)-1H-benzimidazol-2-amine 6-Chloro-5-fluoro-1-(2,3-di-O-acetyl-5-deoxy-beta-D-ribofuranosyl)-N-(1-methylethyl)-1H-benzimidazol-2-amine (2 g) was deprotected according to general procedure III. The crude product was triturated with diisopropyl ether to yield a white powder (1.54 g, 90%); m.p. 97–99° C.; $^1$H NMR (DMSO-$d_6$) δ: 7.36–7.17 (m, 2H), 6.60 (d, 0.5H), 6.53 (d, 0.5H), 5.69 (m, 1H), 5.27 (m, 2H), 4.36 (q, 1H), 4.03 (m, 1H), 3.92 (m, 1H), 3.83 (bs, 1H), 1.41 (d, 3H), 1.23 (d, 6H).

Example 30

5-Nitro-1-(5-deoxy-beta-D-ribofuranosyl)-N-(1-methylethyl)-1H-benzimidazol-2-amine A. 5-Nitro-1-(2,3-di-O-acetyl-5-deoxy-beta-D-ribofuranosyl)-N-(1-methylethyl)-1H-benzimidazol-2-amine 5-nitro-N-(1-methylethyl)-1H-benzimidazol-2-amine (1.1 g) was coupled to 1,2,3-tri-O-acetyl-5-deoxy-D-ribofuranose according to General Procedure II. The crude product was purified by flash chromatography (1:1 ethyl acetate/hexanes) to yield the title compound (0.420 g) as a mixture of 5,6 regioisomers. MS (AP): m/z 443 (M+Na).

B. 5-Nitro-1-(5-deoxy-beta-D-ribofuranosyl)-N-(1-methylethyl)-1H-benzimidazol-2-amine 5-Nitro-1-(2,3-di-O-acetyl-5-deoxy-beta-D-ribofuranosyl)-N-(1-methylethyl)-1H-benzimidazol-2-amine (420 mg, 1 mmol) was deprotected according to general procedure IV. The resulting crude product was purified by flash chromatography (8:1:1 $CH_2Cl_2$:ethyl acetate:methanol) to yield the title compound (18 mg) as a ~2:1 mix of regioisomers ($^1$H NMR) along with impure product (220 mg). MS (AP): m/z 335 (M–H); $^1$H NMR (DMSO-$d_6$) δ: 8.00–7.93 (m, 1.5H), 7.83 (d, 0.5H), 5.77 (two d, 1H), 4.34 (m, 1H), 1.38 (m, 3H), 1.20 (d, 6H).

Example 31

5-Chloro-6-trifluoromethyl-1-(2,3-di-O-acetyl-5-deoxy-1-beta-D-ribofuranosyly)-N-(1-methylethyl)-1H-benzimidazol-2-amine 5-Chloro-6-trifluoromethyl-N-(1-methylethyl)-1H-benzimidazol-2-amine (1.38 g) was coupled to 1,2,3-tri-O-acetyl-5-deoxy-D-ribofuranose according to General Procedure II. The crude product was purified by flash chromatography (1:1 ethyl acetate:hexane) to yield the title compound (1.4 g, 59%) as a white foam. $^1$H NMR (DMSO-$d_6$) δ: 7.75–7.62 (m, 2H), 6.16 (two d, 1H), 2.15 (s, 3H), 2.01 (s, 3H).

Example 32

5-Chloro-6-trifluoromethyl-1-(5-deoxy-beta-D-ribofuranosyl N-(1-methylethyl)-1H-benzimidazol-2-amine 5-Chloro-6-trifluoromethyl-1-(2,3-di-O-acetyl-5-deoxy-1-beta-D-ribofuranosyl)-N-(1-methylethyl)-1H-benzimidazol-2-amine (0.95 g, 2 mmol) was hydrolyzed according to general procedure IV. The crude product was purified by flash chromatography (9:0.5:0.5 $CH_2Cl_2$:ethyl acetate:methanol) to yield the title compound (250 mg, 32%) as a white solid (1:1 mix of regioisomers by $^1$H NMR) after trituration with diisopropyl ether. MS (ES): m/z 392 (M–1); $^1$H NMR (DMSO-$d_6$) δ: 7.63–7.43 (four s, 2H), 6.92–6.74 (two d, 1H), 5.79 (two d, 1H), 5.33 (m, 2H), 4.38 (m, 1H), 4.14–3.97 (m, 2H), 3.84 (bs, 1H), 1.41 (m, 3H) 1.25 (d, 6H).

Anal. Calcd. for $C_{16}H_{19}N_3O_3ClF_3$: C, 48.80; H, 4.86; N, 10.67. Found C, 48.97; H, 4.92; N, 10.52.

Example 33

2-Chloro-5-methoxy-1-(2,3-di-O-acetyl-5-deoxy-beta-D-ribofuranosyl)-1H-benzimidazole 2-Chloro-5-methoxy-1H-benzimidazole (0.661 g, 3.6 mmol) was coupled to 1,2,3-tri-O-acetyl-5deoxy-D-ribofuranose according to General Procedure II. The crude product was purified by flash chromatography (9:1 methylene chloride/ether) to yield the title compound (0.900 g, 65%) as a ~1:1 mix of regioisomers ($^1$H NMR); MS (AP): m/z 405 (M+Na); $^1$H NMR (DMSO-$d_6$) δ: 7.65–7.54 (two d, 1H), 7.21 (s, 1H), 6.97 (m, 1H), 6.18–6.11 (two d, 1H), 5.70–5.59 (m, 1H), 5.21 (q, 1H), 4.27 (m, 1H), 3.83 (two s, 3H), 2.16 (s, 3H), 2.05 (s, 3H), 1.51 (t, 3H).

Example 34

2-Chloro-5-methoxy-1-(5-deoxy-beta-D-ribofuranosyl)-1H-benzimidazole

2-Chloro-5-methoxy-1-(2,3-di-O-acetyl-5-deoxy-beta-D-ribofuranosyl)-1H-benzimidazole (0.815 g, 2.1 mmol) was deprotected according to general procedure IV. The crude product was purified by flash chromatography (9:0.5:0.5 CH$_2$Cl$_2$:ethyl acetate:methanol) to yield the title compound (0.470 g, 75%) as a white solid after trituration with diethyl ether. $^1$H NMR (DMSOd$_6$) δ: 7.50–7.44 (m, 1H), 7.15 (d, J=2.4 Hz, 0.4H), 7.02 (d, J=2.4 Hz, 0.6H), 6.89 (m, 1H), 5.82 (d, J=6.6 Hz, 0.5H), 5.78 (d, J=6.5 Hz), 4.48 (t, J=6.3 Hz, 0.5H), 4.43 (t, J=6.3, 0.5H), 3.98 (m, 1H), 3.85 (m, 1H), 3.76 (two s, 3H), 1.37 (two d, J=6.4 Hz, 3H).

Example 35

5-Methoxy-1-(5-deoxy-beta-D-ribofuranosyl)-N-(1-methylethyl)-1H-benzimidazol-2-amine 2-Chloro-5-methoxy-1-(5-deoxy-beta-D-ribofuranosyl)-1H-benzimidazole (0.320 g, 1.1 mmol) was dissolved in ethanol (15 mL) and isopropylamine (5 mL). The resulting mixture was heated in a sealed tube for three days, after which time it was concentrated in vacuo. The resulting product was purified by flash chromatography (9:0.5:0.5 CH$_2$Cl$_2$:ethyl acetate:methanol) to yield the title compound (18 mg, 5%) as a 1.5:1 mix of regioisomers by $^1$H NMR; MS (ES): m/z 322 (M+1); $^1$H NMR (DMSO-d$_6$) δ: 7.13 (d, J=8.5 Hz, 0.4H), 7.03 (d, J=8.5, 0.6H), 6.85 (d, J=2.4 Hz, 0.6H), 6.76 (d, J=2.4 Hz, 0.4H), 6.62 (dd, 0.4H), 6.50 (dd, 0.6H), 5.67 (t, 1H), 5.28–5.19 (m, 1.5H), 4.37 (m, 1H), 3.73 (s, 3H), 1.40 (m, 3H), 1.23 (d, 6H).

Example 36

5-Chloro-6-methylthio-1-(2,3-di-O-acetyl-5-deoxy-beta-D-ribofuranosyl )-N-(1-methylethyl)-1H-benzimidazol-2-amine and 6-Chloro-5-methylthio-1-(2,3-di-O-acetyl-5-deoxy-beta-D-ribofuranosyl)-N-(1-methylethyl)-1H-benzimidazol-2-amine A. 4-Chloro-2-nitro-5-methylthioaniline Methyl mercaptan gas was passed into a stirred suspension of 1.16 g (30 mmol) of 60% oil-dispersed NaH in 45 mL of DMF until evolution of H$_2$ gas ceased. 5 g (24 mmol) of 4,5-dichloro-2-nitroaniline (Aldrich) was then added portionwise. After 30 min of stirring, the reaction mixture was poured into 200 mL of water. Yellow precipitate formed was collected by filtration and dried. This gave 3.8 g (72%) of the title compound as a yellow solid. $^1$H NMR (DMSO-d$_6$) δ2.5 (s, 3H, CH$_3$), 6.9 (s, 1H, aromatic), 7.6 (br s, 2H, NH$_2$), 8.0 (s, 1H, aromatic)

B. 3-Chloro-4-methylthio-1,2-phenylenediamine

A mixture of 3.7 g (17 mmol) of 4-Chloro-2-nitro-5-methylthioaniline and 12 g (68 mmol) of sodium hydrosulfite (Aldrich) was refluxed in 200 mL of ethanol and 80 ml of water for 2 h. The reaction mixture was concentrated and then redissolved in 200 mL of EtOAc. After washing with sat. brine and water, the EtOAc solution was dried over MgSO$_4$. Solvent removal and drying of the resultant product in vacuo resulted in 2.72 g (85%) of a red-brown solid. $^1$H NMR (DMSO-d$_6$) δ2.3 (s, 3H, CH$_3$), 4.89 (br s, 4H, 2×NH$_2$), 6.6 (s, 2H, aromatic)

C. 5-Chloro-6-methylthio-N-(1-methylethyl)-1H-benzimidazol-2-amine

A mixture of 2.7 g (14 mmol) of 3-chloro-4-methylthio-1,2-phenylenediamine and 1.52 g (15 mmol) of isopropyl isothiocyanate in 30 mL of pyridine was heated at 80° C. for 30 min. The reaction mixture was cooled to room temperature and this was followed by the addition of 7.72 g (18 mmol) of N-cyclohexyl-N-(2-morpholinoethyl)-carbodiimide methyl-toluenesulfonate (Fluka). The resultant mixture was heated to 90° C. and stirred for 18 h. The mixture was diluted with 200 mL of ether. Precipitate was filtered and discarded. The filtrate was concentrated and then redissolved in 200 mL of EtOAc. This was washed repeatedly with water, sat. brine and dried (MgSO$_4$). After solvent removal, the crude product was flash column chromatographed on silica gel with MeOH/CH$_2$Cl$_2$ (1:9) to give 2.57 g (72%) of a light brown foam. $^1$H NMR (DMSO-d$_6$) δ1.2 (d, 6H, 2×CH$_3$), 2.22 (s, 3H, CH$_3$), 3.84 (m, 1H, CH), 6.7 (d, 1H, NH), 7.1 (s, 1H, aromatic), 7.2 (s, 1H, aromatic).

D. 5Chloro-6-methylthio-1-(2,3-di-O-acetyl-5-deoxy-beta-D-ribofuranosyl)-N-(1-methylethyly1H-benzimidazol-2-amine and 6-Chloro-5-methylthio-1-(2,3-di-O-acetyl-5-deoxy-beta-D-ribofuranosyl)-N-(1-methylethyl)-1H-benzimidazol-2-amine Starting with 5-chloro-6-methylthio-N-(1-methylethyl)-1H-benzimidazol-2-amine, these isomers were prepared according to general procedure II. Flash column chromatography on silica gel with MeOH/CH$_2$Cl$_2$ (3:97) resulted first in 0.5 g of a light brown oil which was a mixture of 5-chloro-6-methylthio-1-(2,3-di-O-acetyl-5-deoxy-beta-D-ribofuranosyl)-N-(1-methylethyl)-1H-benzimidazol-2-amine and 6-Chloro-5-methylthio-1-(2,3-di-O-acetyl-5-deoxy-beta-D-ribofuranosyl)-N-(1-methylethyl)-1H-benzimidazol-2-amine by NMR analysis. This was followed by 1.46 g of a crude mixture of 5-chloro-6 methylthio-1-(2,3di-O-acetyl-5-deoxy-beta-D-ribofuranosyl)-N-(1-methylethyl)-1H-benzimidazol-2-amine and 6-chloro-5-methylthio-1-(2,3-di-O-acetyl-5-deoxy-beta-D-ribofuranosyl)-N-(1-methylethyly1H-benzimidazol-2-amine and 5-chloro-6-methylthio-N-(1-methylethyl)-1H-benzimidazol-2-amine. The 0.5 g of light brown oil was further purified using flash column chromatography on silica gel with acetone/CH$_2$Cl$_2$ (1:19). This gave 0.15 g of an oil identified as 5-Chloro-6-methylthio-1-(2,3-di-O-acetyl-5-deoxy-beta-D-ribofuranosyl)-N-(1-methylethyl)-1H-benzimidazol-2-amine by NOE experiment. Further elution gave 0.14 g of 54 as an oil, also confirmed by NOE experiment. $^1$H NMR for 53 (DMSO-d$_6$) δ1.2 (t, 6H, 2×CH$_3$), 1.42 (d, 3H, CH$_3$), 1.96 (s, 3H, COCH$_3$), 2.09 (s, 3H, COCH$_3$), 3.9–4.05 (m, 1H, CH), 4.06–4.1 (mt, 1H, CH), 5.1 (t, 1H, CH), 5.48 (t, 1H, CH), 6.05 (d, 1H, CH), 6.67 (d, 1H, NH), 7.07 (s,1H, aromatic), 7.26 (s,1H, aromatic)

$^1$H NMR for 54 (DMSO-d$_6$) δ1.2 (t, 6H, 2×CH$_3$), 1.42 (d, 3H, CH$_3$), 1.96 (s, 3H, COCH$_3$), 2.09 (s, 3H, COCH$_3$), 3.9–4.1 (m, 1H, CH), 4.05 (quintet, 1H, CH), 5.1 (t, 1H, CH), 5.5 (t, 1H, CH), 6 (d, 1H, CH), 6.67 (d, 1H, NH), 7.26 (s, 1H, aromatic), 7.35 (s, 1H, aromatic).

Example 37

5-Chloro-1-(2,3-di-O-acetyl-5-deoxy-beta-D-ribofuranosyl )-6-methylsulfonyl-1H-benzimidazole A mixture of 0.09 g (0.2 mmol) of 5-chloro-6-methylthio-N-(1-methylethyl)-1H-benzimidazol-2-amine and 0.12 g (0.4 mmol) of meta-chloroperoxybenzoic acid (Aldrich) in 10 mL of CH$_2$Cl$_2$ was stirred for 3 h. The reaction mixture was diluted with 50 ml of EtOAc. This EtOAc solution was washed with sat. sodium bisulfite solution (2×20 mL), sat. NaHCO$_2$ (2×20 mL) and sat. brine. After drying (MgSO$_4$) and solvent removal, 0.08 g (82%) of the title compound was obtained as an oil. MS (ES$^+$) m/e 510 (M$^+$+23, 100%).

Example 38

5-Chloro-6-methanesulfonyl-1-(5-deoxy-beta-D-ribofuranosyl)-N-(1-methylethyl)-1H-benzimidazol-2-amine Starting with 5-chloro-1-(2,3-di-O-acetyl-5-deoxy-beta-D-ribofuranosyl)-6-methylsulfonyl-1H-benzimidazole, this reaction was performed according to general procedure III to give a 79% yield of the title compound. $^1$H NMR (DMSO-d$_6$) δ1.2 (t, 6H, 2×CH$_3$), 1.4 (d, 3H, CH$_3$), 3.27 (s, 3H, CH$_3$), 3.75–3.8 (m, 1H, CH), 3.9–4 (m, 1H, CH), 4–4.1 (m, 1H, CH), 4.26 (t, 1H, CH), 5.4 (br s, 2H, 2×OH)), 5.8 (d, 1H, CH),7.05 (d, 1H, NH), 7.42 (s, 1H, aromatic), 7.82 (s, 1H, aromatic)

Example 39

6-Chloro-5-methanesulfonyl-1-(2,3-di-O-acetyl-5-deoxy-β-D-ribofuranosyl)-N-(1-methylethyl)-1H-benzimidazol-2-amine A mixture of 0.14 g (0.31 mmol) of 6-chloro-5-methylthio-1-(2,3-di-O-acetyl-5-deoxy-beta-D-ribofuranosyl)-N-(1-methylethyl)-1H-benzimidazol-2-amine and 0.11 g (0.61 mmol) of meta-chloroperoxybenzoic acid in 15 mL of CH$_2$Cl$_2$ was stirred for 3 h. The reaction mixture was diluted with 50 ml of EtOAc. This EtOAc solution was washed with sat. sodium bisulfite solution (2×20 mL), sat. NaHCO$_3$ (2×20 mL) and sat. brine. After drying (MgSO4) and solvent removal, 0.13 g (86%) of the title compound was obtained as an oil. MS (ES$^+$) m/e 510 (M$^+$+23, 100%).

Example 40

6-Chloro-5-methanesulfonyl-1-(5-deoxy-β-D-ribofuranosyl )-N-(1-methylethyl)-1H-benzimidazol-2-amine Starting with 6-chloro-5-methanesulfonyl-1-(2,3-di-O-acetyl-5-deoxy-β-D-ribofuranosyl)-N-(1-methylethyl)-1H-benzimidazol-2 -amine, this compound was prepared according to general procedure III to give a 18% yield of the title compound. $^1$H NMR (DMSO-d$_6$) δ1.2 (t, 6H, 2×CH$_3$), 1.37 (d, 3H, CH$_3$), 3.26 (s, 3H, CH$_3$), 3.7–3.82 (m, 1H, CH), 3.9–4 (m, 1H, CH), 4–4.1 (m, 1H, CH), 4.35 (q, 1H, CH), 5.2–5.3 (m, 2H, 2×OH)), 5.7 (d, 1H, CH), 6.72 (d, 1H, NH), 7.38 (s, 1H, aromatic), 7.73 (s, 1H, aromatic). MS (Cl) m/e 426 (M$^+$+23, 100%), 428 (40%). NMR indicated presence of 14% of 5-Chloro-6-methanesulfonyl-1-(5-deoxy-beta-D-ribofuranosyl)-N-(1-methylethyl)-1H-benzimidazol-2-amine.

Example 41

5-Chloro-6-methylthio-1-(5-deoxy-β-D-ribofuranosyl)-N-(1-methylethyl)-1H-benzimidazol-2-amine Starting with 5-chloro-6-methylthio-1-(2,3-di-O-acetyl-5-deoxy-beta-D-ribofuranosyl)-N-(1-methylethyl)-1H-benzimidazol-2-amine, this compound was prepared according to general procedure III to give a 72% yield of the title compound. $^1$H NMR (DMSO-d$_6$) δ1.17 (d, 6H, 2×CH$_3$), 1.35 (d, 3H, CH$_3$), 2.41 (s, 3H, CH$_3$), 3.7–3.8 (m,1H, CH), 3.89–3.91 (m,1H, CH), 3.95–4 (m, 1H, CH), 4.3 (q, 1H, CH), 5.2 (d, H, OH), 5.27 (d, 1H, OH), 5.67 (d, 1H, CH), 6.43 (d,1H, NH), 7 (s,1H, aromatic), 7.26 (s, 1H, aromatic).

Anal. Calc for C$_{16}$H$_{22}$N$_3$O$_3$ClS.0.2EtOAc: C, 51.8; H, 6.11; N, 10.79; Cl, 9.10. Found: C, 52.2; H, 6.17l; N, 10.44; Cl, 9.22

Example 42

6-Trifluoromethyl-1H-benzimidazole

A mixture of 10 g (60 mmol) of 4-(trifluoromethyl)-1,2-phenylenediamine (Lancaster) and 50 mL of formic acid was refluxed for 2 h. Excess formic acid was then removed in vacuo. To the resultant concentrate was added 200 mL of water during which time a precipitate was discerned. This was filtered and discarded. The filtrate was concentrated in vacuo and redissolved in EtOAc. After repeated washing with saturated NaHCO$_3$, the EtOAc solution was dried over MgSO$_4$ and concentrated. The concentrate was put on a vacuum pump overnight. This resulted in 9.27 g (83%) of a yellow solid. $^1$H NMR (DMSO-d$_6$) δ7.5 (d,1H, aromatic), 7.8 (d, 1H, aromatic), 8 (s, 1H, aromatic), 8.4 (s, 1H, CH), 12.8 (br s, 1H, NH).

Anal. Calc for C$_8$H$_5$N$_2$F$_3$: C, 51.62; H, 2.71; N, 15.05. Found, C, 51.75, H, 2.77; N, 15.10.

Example 43

5-Trifluoromethyl-1-(2,3-di-O-acetyl-5-deoxy-beta-D-ribofuranosyl)-1H-benzimidazole and 6-trifluoromethyl-1-(2,3-di-O-acetyl-5-deoxy-beta-D-ribofuranosyl)-1H-benzimidazole With 6-Trifluoromethyl-1H-benzimidazole as the starting benzimidazole, these compounds were synthesized according to general procedure II. Flash column chromatography on silica gel with EtOAc/Hexane (1:1) gave a 25% yield of 5-Trifluoromethyl-1-(2,3-di-O-Acetyl-5-deoxy-beta-D-ribofuranosyl)-1H-benzimidazole and a 30% yield of 6-trifluoromethyl-1-(2,3-di-O-acetyl-5-deoxy-beta-D-ribofuranosyl)-1H-benzimidazole as oil. The structures of these isomers were delineated by COESY experiments.

$^1$H NMR for 5-Trifluoromethyl-1-(2,3-di-O-Acetyl-5-deoxy-beta-D-ribofuranosyl)-1H-benzimidazole (DMSO-d$_6$) δ1.5 (d, 3H, CH$_3$), 2.06 (s, 3H, COCH$_3$), 2.16 (s, 3H, CO CH$_3$), 4.3 (quintet, 1H, CH), 5.2 (t, 1H, CH), 5.7 (t, 1H, CH), 6.36 (d, 1H, CH), 7.65 (d, 1H, aromatic), 8 (d, 1H, aromatic), 8.1 (s, 1H, aromatic), 8.8 (s, 1H, CH).

$^1$H NMR for 6-trifluoromethyl-1-(2,3-di-O-acetyl-5-deoxy-beta-D-ribofuranosyl)-1H-benzimidazole (DMSO-d$_6$) δ1.47 (d, 3H, CH$_3$), 2.06 (s, 3H, COCH$_3$), 2.16 (s, 3H, CO CH$_3$), 4.3 (quintet, 1H, CH), 5.2 (t, 1H, CH), 5.7 (t, 1H, CH), 6.42 (d, 1H, CH), 7.6 (d, 1H, aromatic), 7.9 (d, 1H, aromatic), 8.24 (s, 1H, aromatic), 8.8 (s, 1H, CH).

Example 44

5-Trifluoromethyl-1-(5-Deoxy-beta-D-ribofuranosyl)-N-(1-methylethyl)-1H-benzimidazol-2-amine A. 2-Bromo-5-trifluoromethyl-1-(2,3-di-O-acetyl-5-deoxy-beta-D-ribofuranosyl)-1H-benzimidazole To a refluxing solution of 0.2 g (0.52 mmol) of 5-Trifluoromethyl-1-(2,3-di-O-Acetyl-5-deoxy-beta-D-ribofuranosyl)-1H-benzimidazole in 10 mL of dry THF was added 0.2 g (1.1 mmol) of N-bromosuccinimide (NBS). The reaction mixture was further refluxed for 10 min. Additional 0.1 g of NBS was added. After 5 min, the mixture was poured into an ice-cooled solution of 20 mL CHCl$_3$ and 20 mL sat. NaHCO$_3$. The CHCl$_3$ solution was separated and was further washed with sat. NaHCO$_3$. After drying (MgSO$_4$) and solvent removal, 0.28 g of the title compound was obtained as a semi-solid which was used without further purification in the following reaction.

B. 5-Trifluoromethyl-1-(5-Deoxy-beta-D-ribofuranosyl)-N-(1-methylethyl)-1H-benzimidazol-2-amine Starting with 2-Bromo-5-trifluoromethyl-1-(2,3-di-O-acetyl-5-deoxy-beta-D-ribofuranosyl)-1H-benzimidazole, this compound was prepared according to general procedure V. Following purification by flash column chromatography on silica gel with MeOH/CH$_2$Cl$_2$ and then silica gel preparative plate using the same solvent system, a 19% yield of the title compound was obtained as a white solid. $^1$H NMR (DMSO-d$_6$) δ1.2 (d, 6H, 2×CH$_3$), 1.35 (d, 3H, CH$_3$), 3.78–3.82 (m, 1H, CH), 3.82–3.9 (m, 1H, CH), 3.9–4.1 (m, 1H, CH), 4.39 (q, 1H, CH), 5.2 (d, 1H, OH), 5.25 (d, $_1$H, OH), 5.7 (d, 1H, CH), 6.6 (d, 1H, aromatic), 7.19 (d, 1H, aromatic), 7.3 (d, 1H, NH), 7.45 (s, H, aromatic).

Anal. Calc for C$_{16}$H$_{20}$N$_3$O$_3$F$_3$: C, 53.48; H, 5.61; N, 11.69. Found: C, 53.21; H, 5.6; N, 11.51.

Example 45

2-Bromo-6-trifluoromethyl-1-(2,3-di-O-acetyl-5-deoxy-beta-D-ribofuranosyl)-1H-benzimidazole Starting with 6-trifluoromethyl-1-(2,3-di-O-acetyl-5-deoxy-beta-D-ribofuranosyl)-1H-benzimidazole, this compound was prepared in a manner analogous to that described for 2-bromo-5-trifluoromethyl-1-(2,3-di-O-acetyl-5-deoxy-beta-D-ribofuranosyl)-1H-benzimidazole. Following flash column chromatography on silica with EtOAc/hexane (2:3), a 52% yield of the title compound was obtained as an oil. $^1$H NMR (DMSO-d$_6$) δ1.48 (d, 3H, CH$_3$), 2 (s, 3H, COCH$_3$), 2.1 (s, 3H, COCH$_3$), 4.2–4.3 (m, 1H, CH), 5.2 (t, 1H, CH), 5.63 (t, 1H, CH), 6.22 (d, 1H, CH), 7.6 (d, 1H, aromatic), 7.8 (d, 1H, aromatic), 8.1 (s, 1H, aromatic).

Example 46

6-trifluoromethyl-1-(5-Deoxy-beta-D-ribofuranosyl)-N-(1-methylethyl)-1H-benzimidazol-2-amine Starting with 2-Bromo-6-trifluoromethyl-1-(2,3-di-O-acetyl-5-deoxy-beta-D-ribofuranosyl)-1H-benzimidazole, this compound was prepared according to general procedure V. Following flash column chromatography on silica with MeOH/CH$_2$Cl$_2$ (1:20) and further purification on a silica gel preparative plate using EtOAc/hexane (7:3), a 32% yield of the title compound was obtained as a foam. $^1$H NMR (DMSO-d$_6$) δ1.22 (d, 6H, 2×CH$_3$), 1.4 (d, 3H, CH$_3$), 3.8–3.9 (m, 1H, CH), 3.9–4.06 (m, 1H, CH), 4.06–4.15 (m, 1H, CH), 4.4 (q, 1H, CH), 5.21–5.4 (m, 2H, 2×OH), 5.8 (d, 1H, CH), 6.67 (d, 1H, aromatic), 7.3–7.4 (m, 2H, aromatic and NH), 7.45 (s, H, aromatic).

Anal. Calc for C$_{16}$H$_{20}$N$_3$O$_3$F$_3$0.1H$_2$O: C, 53.21; H, 5.64; N, 11.64. Found: C, 52.86; H, 5.51; N, 11.4.

Example 47

Synthesis of 2-bromo-6-trifluoromethyl-1-(5-deoxy-beta-D-ribofuranosyl)-1H-benzimidazole Starting with 2-bromo-6-trifluoromethyl-1-(2,3-di-O-acetyl-5-deoxy-beta-D-ribofuranosyl)-1H-benzimidazole, this compound was prepared according to general procedure III. Following two flash column chromatographic purifications on silica gel with EtOAc/hexane (3:2), a 14% yield of the title compound was obtained as a foam. $^1$H NMR (DMSO-d$_6$) δ1.4 (d, 3H, Me), 3.8–3.9 (m, 1H, CH), 3.9–4.1 (m, 2H, 2×CH), 4.45 (q, 1H, CH), 5.3 (d, 1H, OH), 5.5 (d, 1H, OH), 5.91 (d,1H, CH), 7.6 (d, 1H, aromatic), 7.82 (d, 1H, aromatic), 7.9 (s, H, aromatic).

Anal. Calc for C$_{13}$H$_{12}$N$_2$O$_3$BrF$_3$: C, 40.97; H, 3.17; N, 7.35; Br, 20.96. Found: C, 40.84; H, 3.22; N, 7.29; Br, 20.89.

Example 48

5-Chloro-1-(2,3-di-O-acetyl-5deoxy-beta-D-ribofuranosyl)-1H-benzimidazole and 6-chloro-1-(2,3-di-O-acetyl-5deoxy-beta-D-ribofuranosyl)-1H-benzimidazole A mixture of 1.17 g (7.7 mmol) of 5-chloro-1H-benzimidazole and 1.88 mL (7.7 mmol) of N,O-bistrimethylsilylacetamide (Aldrich) in 40 mL of 1,2-dichloroethane was heated at reflux for 1 h. The mixture was cooled to room temperature, followed by the addition of 2.95 mL (15.4 mmol) of trimethylsilyl triflate. After stirring for 10 min, 2 g (7.7 mmol) of 1,2,3-tri-O-acetyl-5-deoxy-D-ribofuranoside was added. The reaction mixture was brought to reflux for 1 h and then stirred at room temperature for 18 h. The reaction mixture was diluted with EtOAc (100 mL), and the resultant EtOAc solution was washed with sat. NaHCO$_3$ and sat. brine. After drying (MgSO$_4$) and solvent removal, the crude product was flash column chromatographed on silica gel with EtOAc/hexane (7:3) to give first 0.75 g (28%) of an oil identified as 5-chloro-1-(2,3-di-O-acetyl-5-deoxy-beta-D-ribofuranosyl)-1H-benzimidazole on the basis of NOESY analysis. Further elution resulted in 0.92 g (34%) of 6-chloro-1-(2,3-di-O-acetyl-5-deoxy-beta-D-ribofuranosyl)-1H-benzimidazole, also confirmed by NOESY analysis. $^1$H NMR for 5-chloro-1-(2,3-di-O-acetyl-5-deoxy-beta-D-ribofuranosyl)-1H-benzimidazole (DMSO-d$_6$) δ1.4 (d, 3H, CH$_3$), 2 (s, 3H, COCH$_3$), 2.09 (s, 3H, COCH$_3$), 4.2 (quintet, 1H, CH), 5.12 (t, 1H, CH), 5.6 (t, 1H, CH), 6.2 (d, 1H, CH), 7.3 (d, 1H, aromatic), 7.7 (d, 1H, aromatic), 7.74 (s, 1H, aromatic), 8.6 (s, 1H, CH).

$^1$H NMR for 6-chloro-1-(2,3-di-O-acetyl-5-deoxy-beta-D-ribofuranosyl)-1H-benzimidazole (DMSO-d$_6$) δ1.4 (d, 3H, CH$_3$), 2 (s, 3H, CO CH$_3$), 2.1 (s, 3H, CO CH$_3$), 4.2 (quintet, 1H, CH), 5.12 (t, 1H, CH), 5.6 (t, 1H, CH), 6.2 (d, 1H, CH), 7.28 (d, 1H, aromatic), 7.67 (d,1H, aromatic), 7.85 (s, 1H, aromatic), 8.55 (s,1H, CH).

Example 49

2-Bromo-6-chloro-1-(2,3-di-O-acetyl-5-deoxy-β-D-ribofuranosyl)-1H-benzimidazole

To a refluxing solution of 0.76 g (2.2 mmol) of 6-chloro-1-(2,3-di-O-acetyl-5-deoxy-beta-D-ribofuranosyl)-1H-benzimidazole in 30 mL of THF was added 0.77 g (4.3 mmol) of N-bromosuccinimide. The resultant mixture was further refluxed for 15 min. The reaction mixture was then poured into an ice-cooled mixture of 20 mL sat. NaHCO$_3$ solution and 20 mL CHCl$_3$. The CHCl$_3$ layer was separated and was further washed with sat. NaHCO$_3$. After drying (MgSO$_4$) and solvent removal, a crude product was obtained which was purified by flash column chromatography on silica with EtOAc/hexane (2:3) as the eluent. This gave 0.73 g (79%) of the title compound as an oil. $^1$H NMR (DMSO-d$_6$) δ1.42 (d, 3H, CH$_3$), 2 (s, 3H, COCH$_3$), 2.1 (s, 3H, COCH$_3$), 4.2 (quintet, 1H, CH), 5.2 (t, 1H, CH), 5.6 (t, 1H, CH), 6.1 (d, 1H, CH), 7.3 (d, 1H, aromatic), 7.6 (d, 1H, aromatic), 7.82 (s, 1H, aromatic).

Example 50

6-Chloro-1-(5-deoxy-β-D-ribofuranosyl)-N-(1-methylethyl)-1H-benzimidazol-2-amine A mixture of 2-bromo-6-chloro-1-(2,3-di-O-acetyl-5-deoxy-β-D-ribofuranosyl)-1H-benzimidazole and 10 mL of isopropylamine in 5 mL of absolute ethanol was refluxed for 18 h. To this resultant mixture was added 1 mL of 1N NaOH and the resultant solution was dry-packed in silica gel. Flash column chromatography on silica gel with EtOAc/hexane (1:1) gave 0.15 g of a still impure product. Further purification on a silica gel preparative plate using EtOAc/hexane (1:1) gave 0.06 g (28%) of the title compound as a foam. $^1$H NMR (DMSO-d$_6$) δ1.18 (d, 6H, 2×CH$_3$), 1.35 (d, 3H, CH$_3$), 3.7–3.8 (m, 1H, CH), 3.8–3.9 (m, 1H, CH), 4 (sextet, 1H, CH), 4.3 (q, 1H, CH), 5.2–5.21 (m, 2H, 2×OH), 5.61 (d, 1H, CH), 6.38 (d, 1H, aromatic), 6.95 (d, 1H, aromatic), 7.1–7.2 (m, 2H, aromatic & NH).

Anal. Calc for $C_{15}H_{20}N_3O_3Cl.0.1HCl.0.1EtOAc$: C, 54.68; H, 6.23; N, 12.42; Cl, 11.53. Found: C, 54.61; H, 6.01; N, 12.04; Cl, 11.55

Example 51

5-Chloro-1-(5-deoxy-beta-D-ribofuranosyl)-N-(1-methylethyl )-1H-benzimidazol-2-amine A. 2-Bromo-5-chloro-1-(2,3-di-O-acetyl-5-deoxy-beta-D-ribofuranosyl)-1H-benzimidazole Following an analogous procedure described for Example 49, this compound was obtained in a quantitative yield, which was deemed pure enough by NMR for the following reaction.

B. 5-Chloro-1-(5-deoxy-beta-D-ribofuranosyl)-N-(1-methylethyl)-1H-benzimidazol-2-amine This compound was synthesized using 2-bromo-5-chloro-1-(2,3-di-O-acetyl-5-deoxy-beta-D-ribofuranosyl)-1H-benzimidazole according to general procedure V resulting in a 20% yield of the title compound as a foam. $^1$H NMR (DMSO-$d_6$) δ1.18 (d, 6H, 2×CH$_3$), 1.3 (d, 3H, CH$_3$), 3.7–3.8 (m, 1H, CH), 3.8–3.91 (m, 1H, CH), 4 (sextet, 1H, CH), 4.3 (q, 1H, CH), 5.19 (d, 1H, OH), 5.21 (d, 1H, OH), 5.61 (d, 1H, CH), 6.5 (d, 1H, aromatic), 6.8 (d, 1H, aromatic), 7.1 (d, 1H, NH), 7.2 (s, H, aromatic).

Anal. Calc for $Cl_{15}H_{20}N_3O_3Cl.0.1HCl.0.1EtOAc$: C, 54.68; H, 6.23; N, 12.42; Cl, 11.53. Found: C, 54.29; H, 6.07; N, 12.25; Cl, 11.46.

Example 52

Synthesis of 2-bromo-6-chloro-1-(5-deoxy-β-D-ribofuranosyl)-1H-benzimidazole

A mixture of 0.44 g (1 mmol) of 2-bromo-6-chloro-1-(2,3-di-O-acetyl-5-deoxy-β-D-ribofuranosyl)-1H-benzimidazole and 0.17 g (1.6 mmol) of sodium carbonate in 8 mL of MeOH, 8 mL of EtOH and 2 mL of water was stirred at room temperature for 6 h. The reaction mixture was concentrated and redissolved in 50 mL of EtOAc. After 2 washings with saturated brine, the EtOAc solution was dried over MgSO$_4$. Solvent removal resulted in a crude product which was flash column chromatographed on silica gel with EtOAc/hexane (1:1) to give 0.24 g (69%) of the title compound as a white solid. $^1$H NMR (DMSO-$d_6$) δ1.4 (d, 3H, CH$_3$), 3.8–3.9 (m, 1H, CH), 3.9–4 (m, 1H, CH), 4.45 (q, 1H, CH), 5.21 (d 1H, OH), 5.45 (d, 1H, OH), 5.8 (d, 1H, CH), 7.3 (d, 1H, aromatic), 7.6 (s,1H, aromatic), 7.62 (d, 1H, aromatic).

Anal. Calc for $C_{12}H_{12}N_2BrClO_3$: C, 41.46; H, 3.48; N, 8.06; Br, 22.99; Cl, 10.2. Found: C, 41.71; H, 3.55; N, 7.95; Br, 22.87; Cl, 10.15.

Example 53

5,6-Dichloro-2-ethenyl-1-(2,3-di-O-acetyl-5-deoxy-beta-D-ribofuranosyl) 1H-benzimidazole 2-Bromo-5,6-dichloro-1-(2,3-di-O-acetyl-5-deoxy-beta-D-ribofuranosyl)-1H-benzimidazole (0.22 g, 0.47 mmol), vinyltributyltin (Aldrich, 0.5 ml, 2.4 mmol), tetrakis (triphenylphosphine)palladium(0) (Aldrich, 0.054 g, 0.047 mmol) and DMF (Aldrich Sure Seal, 5 mL) were combined and flushed with argon for 30 min. The solution was warmed to 90° C. After 1 h the DMF was distilled off under reduced pressure. The residue was taken up in ethyl acetate (50 mL) and extracted with 20 mL of saturated NH$_4$Cl. The organic layer was dried with magnesium sulfate (anhyd), filtered, and evaporated. The crude residue was purified on a silica gel column (2.5×14 cm, 230–400 mesh) with 1:40 methanol:dichloromethane to give the title compound (0.1 g, 0.24 mmol, 51%); MS (ES+): m/z (rel. intensity) 436 (100, M$^+$+Na); $^1$H NMR (DMSO-$d_6$) δ8.06 (s,1H, ArH), 7.97 (s, 1H,ArH), 7.10 (dd, 1H, CH, J=11 Hz, J=16.8 Hz), 6.50 (dd, 1H, CH, J=1.8 Hz, J=16.8 Hz), 6.32 (d, 1H, CH, J=6.9 Hz), 5.85 (dd, 1H, CH, J=1.8 Hz, J=11 Hz), 5.51 (apparent triplet, 1H, CH, J=7.0 Hz), 5.27 (apparent triplet, 1H, CH, J=6.5 Hz), 4.27–4.18 (m, CH, 1H), 2.15 (s, 3H, OAc), 1.99 (s, 3H, OAc), 1.53 (d, 3H, CH$_3$, J=6.3 Hz).

Anal. Calcd. for $C_{18}H_{18}N_2O_5Cl_2$ 0.25H$_2$O C, 51.75; H, 4.46; N, 6.71. Found: C, 51.33; H, 4.42; N, 6.53.

Example 54

5,6-Dichloro-2-ethenyl-1-(5deoxy-beta-D-ribofuranosyl)-1H-benzimidazole 5,6-Dichloro-2-ethynyl-1-(2,3-di-O-acetyl-5-deoxy-beta-D-ribofuranosyl) 1H-benzimidazole (0.85 g, 0.20 mmol) was deprotected using general procedure III. Crude product was purified by silica gel chromatography using 1:10 methanol:dichloromethane to give the title compound as an off white solid (0.04 g, 0.12 mmol, 59%); MS (ES+): m/z (rel. intensity) 351 (15, M$^+$+Na);

$^1$H NMR (DMSO-$d_6$) δ7.91 (s, ArH, 1H), 7.81 (s, ArH, 1H), 7.00 (dd,1H, CH, J=11 Hz, J=17 Hz), 6.43 (dd,1H, CH, J=17 Hz), 5.87 (d, 1H, CH, J=6.8 Hz), 5.76 (d, 1H, CH, J=12.3 Hz), 5.41 (d, 1H, OH, J=6.9 Hz), 5.25 (d, 1H, OH, J=5.1 Hz), 4.25 (apparent quartet, 1H, CH, J=6.6 Hz, J=13.3 Hz), 3.97 (apparent triplet, 1H, CH, J=5.2 Hz), 3.84–3.80 (m, 1H, CH), 1.40 (d, 3H, CH, J=6.3 Hz).

Anal. Calcd. for $C_{14}H_{14}N_2O_3Cl_2$ 0.30 H$_2$O C, 50.26; H, 4.40; N, 8.37. Found: C, 50.28; H, 4.36; N, 8.06.

Example 55

5,6-Dichloro-2-ethynyl-1-(2,3-di-O-acetyl-5-deoxy-beta-D-ribofuranosyl)-1H-benzimidazole 2-Bromo-5,6-dichloro-1-(2,3-di-O-acetyl-5-deoxy-beta-D-ribofuranosyl)-1H-benzimidazole (0.43 g, 0.92 mmol), trimethylacetylene (Aldrich, 0.43 ml, 3.0 mmol), bis (triphenylphosphine)palladium(II) chloride (Aldrich, 0.015 g, 0.02 mmol), cuprous iodide (0.01 g, 0.05 mmol) and triethylamine (distilled from CaH, 30 mL) were combined and flushed with argon for 30 min. The solution was stirred at 25° C. for 1 h then warmed to 80° C. After 3 h the reaction mixture was concentrated and taken up in dichloromethane (100 mL) and extracted with 50 mL of 2% EDTA (Aldrich) twice then with 50 mL of H$_2$O. The organic layer was dried with magnesium sulfate (anhyd), filtered, and evaporated. The crude residue was purified on a silica gel column (2.5×16 cm, 230–400 mesh) with 1:2 ethyl acetate: hexane with 0.1 % triethylamine to give the title compound (0.12 g, 0.28 mmol, 31%); MS (ES+): m/z (rel. intensity) 433 (100, M$^+$+Na); $^1$H NMR (DMSO-$d_6$) δ8.12 (s, 1H, ArH), 8.00 (s, 1H,ArH), 6.21 (d, 1H, CH, J=6.1 Hz), 5.65 (apparent triplet, 1H, CH, J=6.8 Hz), 5.20 (apparent triplet, 1H, CH, J=6.5 Hz), 4.23–4.19 (m, CH, 1H), 2.10 (s, 3H, OAc), 1.98 (s, 3H, OAc), 1.53 (d, 3H, CH$_3$, J=6.3 Hz).

Anal. Calcd. for $C_{18}H_{16}N_2O_5Cl_2$ C, 52.57; H, 3.92; N, 6.81. Found: C, 52.53; H, 4.04; N, 6.67.

Example 56

2-Bromo-5,6-dichloro-1-(3-acetyl-2,5-dideoxy-2-fluoro-beta-D-ribofuranosyl)-1H-benzimidazole A. 2',5'-Dideoxy-5'-iodo-2'-fluorouridine 2'-Deoxy-2'-fluorouridine (3.50 g, 14.2 mmoles) prepared by the method of Codington, J. F.; Doerr, I. L.; and Fox, J.

J. (JOC, 1964, 29, 558) was placed in an oven dried flask. Toluene (Aldrich, Sure Seal, 30 mL) was added and the mixture boiled to remove water. Excess toluene was removed in vacuo. DMF (Aldrich, Sure Seal, 20 mL) was added. Triphenoxy-methylphosphonium iodide (Aldrich, 7.40 g, 16.4 mmoles, 1.15 eq.) was dissolved in DMF (Aldrich, Sure Seal, 20 mL) and added by cannula to the DMF solution of 2'-fluorouridine. The reaction was stirred at room temperature for 3.5 h. Methanol (5 mL) added and the solvents removed under high vacuum. The dark residue was purified by chromatography on a 5×16 cm column of silica gel eluted with 2% methanol in chloroform followed by 5% methanol in chloroform. The product containing fractions were combined and the solvents removed in vacuo. The product (2.9 g) was obtained in 58% yield. MS (APCl(−)): m/z (rel. intensity) 483 (20%, (M+I)$^-$); $^1$H NMR (DMSO-d$_6$) δ7.63 (d, 1H, H6, J=9 Hz), 5.86 (d, 1H, H-1', J=22 Hz), 5.80 (d, 1H, H5, J=9 Hz), 5.63 (d, 1H, OH, J=8 Hz), 5.21 (d, 1H, H-2', J=53 Hz), 4.0 (m, 1H), 3.75 (m, 1H), 3.55 (m, 1H), 3.4 (m, 1H).

B. 2',5'-Dideoxy-2'-fluorouridine

2',5'-Dideoxy-5'-iodo-2'-fluorouridine (2.9, 8.1 mmoles) was dissolved in 95% ethanol (25 mL). Ammonium hydroxide (1.1 mL, 16.2 mmoles, 2 eq.) was added followed by 10% Pd/C (Aldrich, 0.1 g). Reaction under 50 psi hydrogen was carried out for 5 hours. The mixture was filtered and the pH adjusted to 7 with 1N HCl. The solvents were removed in vacuo and the residue dissolved in water. The product was extracted with ethyl acetate (3×). The ethyl acetate solution was dried with MgSO$_4$, filtered, and the solvent removed in vacuo. The residue was purified by chromatography on 100 g of silica gel eluted with ethyl acetate. The product containing fractions were combined and the solvents removed in vacuo. The yield was 1.1 g, 58%. MS (APCl(−)): m/z (rel. intensity) 229 (100%, M$^-$); $^1$H NMR (DMSO-d$_6$) δ7.54 (d, 1H, H6, J=8 Hz), 5.76 (d, 1H, H-1', J=22 Hz), 5.59 (d,1H, H5, J=8 Hz), 5.55 (d, 1H, OH, J=6 Hz), 5.05 (d, 1H, H-2', J=53 Hz), 3.8 (m, 2H), 1.27 (d, 3H, H-5', J=6 Hz).

C. 5,6-Dichloro-1-(2,5-dideoxy-2-fluoro-beta-D-ribofuranosyl)-benzimidazole

2',5'-Dideoxy-2'-fluorouridine (1.1 g, 4.8 mmoles) was dissolved in 950 mL of 50 mmoler pH 6.0 citrate buffer. 5,6-Dichlorobenzimidazole (Townsend and Revankar, Chem. Rev. 1970, 70:389) (0.53 g, 2.9 mmoles) was added followed by 71,250 units of N-deoxyribofuranosyl transferase (Freeman, et.al, Bioorg. & Med. Chem. 1995, 3(4):447–58). The reaction was placed in a 50° C. water bath and gently shaken for 27 days. The enzyme was precipitated by heating to 80° C. then cooling to room temperature. Celite (50–60 g) was added and the reaction filtered. The product was extracted with ethyl acetate (3×). The ethyl acetate was removed in vacuo and the residue purified by chromatography on 75 g of silica gel eluted with ethyl acetate. The product containing fractions were combined and the solvents removed in vacuo. The yield was 0.5 g, 56%. MS (APCl(+)): m/z, 305; $^1$H NMR (DMSO-d$_6$) δ8.51 (s, 1H, H-2), 8.03 (s,1H, Ar—H), 7.98 (s,1H, Ar—H), 6.32 (d,1H, H-1', J=18 Hz), 5.72 (d, 1H, OH-3', J=6 Hz), 5.34 (d, 1H, H-2', J=53 Hz), 4.0 (m, 2H,), 1.32 (d, 3H, H-5', J=4 Hz).

D. 5,6-Dichloro-1-(3-acetyl-2,5-dideoxy-2-fluoro-beta-D-ribofuranosyl)-1H-benzimidazole 5,6-Dichloro-1-(2,5-dideoxy-2-fluoro-beta-D-ribofuranosyl)-1H-benzimidazole (0.45 g, 1.5 mmoles) was dissolved in pyridine (Aldrich, Sure Seal, 20 mL) and boiled to remove water. The solution was chilled to 0° C. in an ice bath. Acetic anhydride (Aldrich, 260 μL, 2.9 mmoles, 2 eq.) was added and the reaction was allowed to warm to room temperature while stirring overnight. Methanol (3 mL) was added and the solvents removed in vacuo. Residual pyridine was removed by coevaporation with toluene (3×). The residue was partitioned between water and ethyl acetate. The ethyl acetate solution was dried with MgSO$_4$, filtered, and the solvent removed in vacuo. The product was used without further purification. The yield was 0.45 g, 88%. MS (FAB+): m/z, 347; $^1$H NMR (DMSO-d$_6$) δ8.61 (s,1H, H-2), 8.08 (s,1H, Ar—H), 8.00 (s,1H, Ar—H), 6.38 (d, 1H, H-1', J=18 Hz), 5.70 (d, 1H, H-2', J=53 Hz), 5.1 (m, 1H), 4.2 (m, 1H), 2.1 (s, 3H, acetyl), 1.38 (d, 3H, H-5', J=6 Hz).

E. 2-Bromo-5,6-dichloro-1-(3-acetyl-2,5-dideoxy-2-fluoro-beta-D -ribofuranosyl)-1H-benzimidazole 5,6-Dichloro-1-(3-acetyl-2,5-dideoxy-2-fluoro-beta-D-ribofuranosyl)-1H-benzimidazole (0.45 g, 1.3 mmoles) was boiled in toluene to remove water. Excess toluene was removed in vacuo. THF (Aldrich, Sure Seal, 20 mL) was added and the solution heated to reflux in an 85° C. oil bath. NBS (Aldrich, 0.46 g, 2.6 mmoles, 2 eq.) was added and the reaction refluxed 7 mins. A second portion (0.23 g, 1.3 mmoles, 1 eq.) was added and reflux continued 10 mins. The reaction was removed from the heat, diluted with chloroform (40 mL) and cooled to room temperature. The solution was washed with sat. sodium bicarbonate (2×), dried with MgSO$_4$ and filtered. The solvents were removed in vacuo and the residue purified by chromatography on 75 g of silica gel eluted with ethyl acetate/hexane (1:4, v/v). The product containing fractions were combined and the solvents removed in vacuo. The yield was 0.42 g, 75%. MS (FAB+): m/z, 425; $^1$H NMR (DMSO-d$_6$) δ7.99 (s,1H, Ar—H), 7.97 (s, 1H, Ar—H), 6.27 (d, 1H, H-1', J=19 Hz), 5.69 (d, 1H, H-2', J=53 Hz), 5.1 (m, 1H), 4.25 (m, 1H), 2.13 (s, 3H, acetyl), 1.45 (d, 3H, H-5', J=6 Hz).

Example 57

2-Bromo-5,6-dichloro-1-(2,5-dideoxy-2-fluoro-beta-D-ribofuranosyl)-1H-benzimidazole 2-Bromo-5,6-dichloro-1-(3-acetyl-2,5-dideoxy-2-fluoro-beta-D-ribofuranosyl)-1H-benzimidazole (0.42 g, 1.0 mmoles) was dissolved in methanol and ethanol (17 mL each). Sodium carbonate (0.22 g, 2.1 mmoles, 2 eq.) was dissolved in 4.2 mL water and added to the starting material solution. The reaction was stirred at room temperature overnight. The solution was diluted with water (40 mL). The product was extracted with ethyl acetate (2×). The ethyl acetate solution was dried with MgSO$_4$, filtered, and the solvent removed in vacuo. The residue purified by chromatography on 75 g of silica gel eluted with ethyl acetate/hexane (1:4, v/v) followed by (1:2, v/v). The product containing fractions were combined and the solvents removed in vacuo. The yield was 0.3 g, 75%. MS (FAB(+): m/z, 383; $^1$H NMR (DMSO-d$_6$) δ7.97 (s, 1H, Ar—H), 7.88 (s, 1H, Ar—H), 6.20 (d, 1H, H-1', J=19 Hz), 5.77 (d, 1H, OH-3', J=5 Hz), 5.40 (d, 1H, H-2', J=53 Hz), 4.0 (m, 2H,), 1.40 (d, 3H, H-5', J=6 Hz).

Example 58

5,6-Dichloro-1-(2,5-dideoxy-2-fluoro-beta-D-ribofuranosyl)-N-(1-methylethyl)-1H-benzimidazol-2-amine 2-Bromo-5,6-dichloro-1-(2,5-dideoxy-2-fluoro-beta-D-ribofuranosyl)-1H-benzimidazole (0.075 g, 0.2 mmoles) was heated in a solution of isopropylamine (Fluka, 2 mL) and absolute ethanol (6 mL) in a 90° C. oil bath for 18 hrs. The solvents were removed in vacuo. The residue was partitioned between water and ethyl acetate. The ethyl acetate solution was dried with $MgSO_4$, filtered and solvent removed in vacuo to give the product (0.06 g) in 85% yield. MS (APCl+): m+1/z, 362; $^1$H NMR (DMSO-$_6$) δ7.39 (s, 1H, Ar—H), 7.18 (s, 1H, Ar—H), 6.94 (d, 1H, NH, J=7 Hz), 6.09 (d, 1H, H-1', J=19 Hz), 5.72 (d, 1H, OH-3', J=6 Hz), 5.26 (d, 1H, H-2', J=53 Hz), 3.9 (m, 3H,), 1.35 (d, 3H, H-5', J=6 Hz), 1.18 (m, 6H, $CH_3$).

Example 59

5,6-Dichloro-1-(5-deoxy-beta-D-ribofuranosyl)-N-(cyclopropyl)-1H-benzimidazol-2-amine Following General Procedure V, cyclopropyl amine (Aldrich, 5 mL, 71.28 mmol), and 2-bromo-5,6-dichloro-1-(5-deoxy-beta-D-ribofuranosyl)-1H-benzimidazole (250 mg, 0.65 mmol) reacted for 92 h. Purification on a silica gel column with 1:15 methanol:$CH_2Cl_2$ gave the title compound (120 mg, 0.33 mmol, 52%); MS (EI): m/z (rel. intensity) 358 (0.08, M$^+$); $^1$H NMR (DMSO-d$_6$) δ7.48 (s, 1H, Ar—H), 7.35 (s, 1H, Ar—H), 7.13 (d, 1H, NH, J=2.0 Hz), 5.61 (d,1H, CH, J=6.6 Hz), 5.25 (m, 2H, 2 overlapping OH), 4.36 (m,1H, CH), 3.88 (m, 1H, CH), 3.79 (m, 1H, CH), 2.76 (m, 1H, CH), 1.36 (d, 3H, $CH_3$, J=6.3 Hz), 0.70 (m, 2H, $CH_2$), 0.53 (m, 2H, $CH_2$).

Anal. Calcd. for $C_{15}H_{17}N_3O_3Cl_2$.0.12 $C_3H_7N$: C, 50.92; H, 4.89; N, 11.88. Found: C, 51.23; H, 4.99; N, 11.51.

Example 60

5,6-Dichloro-1-(5-deoxy-beta-D-ribofuranosyl)-N-(cyclopentyl)-1H-benzimidazol-2-amine Following General Procedure V, cyclopentyl amine (Aldrich, 5 mL, 50.68 mmol), and 2-bromo-5,6-dichloro-1-(5-deoxy-beta-D-ribofuranosyl)-1H-benzimidazole (250 mg, 0.65 mmol) reacted for 92 h. Purification on a silica gel column with 1:15 methanol:$CH_2Cl_2$ gave the title compound (238 mg, 0.62 mmol, 95%); MS (EI): m/z (rel. intensity) 386 (0.20, M$^+$); $^1$H NMR (DMSO-d$_6$) δ7.42 (s, 1H, Ar—H), 7.33 (s, 1H, Ar—H), 6.68 (d, 1H, NH, J=6.7 Hz), 5.71 (d, 1H, CH, J=6.8 Hz), 5.29 (m, 2H, overlapping OH), 4.32 (m, 1H. CH), 4.16 (m, 1H, CH), 3.92 (m, 1H, CH), 3.81 (m, 1H, CH), 1.95 (m, 2H, $CH_2$), 1.70 (m, 2H, $CH_2$), 1.56 (m, 4H, $CH_2$), 1.38 (d, 3H, $CH_3$, J=6.4 Hz).

Anal. Calcd. for $C_{17}H_{21}N_3O_3Cl_2$.0.1 $C_5H_{11}N$: C, 53.24; H, 5.64; N, 11.00. Found: C, 53.63; H, 5.64; N, 10.70.

Example 61

5,6-Dichloro-1-(5-deoxy-beta-D-ribofuranosyl)-N-(2-propenyl)-1H-benzimidazol-2-amine Following General Procedure V, allylamine (Aldrich, 5 mL, 66.64 mmol), and 2-bromo-5,6-dichloro-1-(5-deoxy-beta-D-ribofuranosyl)-1H-benzimidazole (250 mg, 0.65 mmol) reacted for 92 h. Purification on a silica gel column with 1:25 methanol:$CH_2Cl_2$ gave the title compound (195 mg, 0.54 mmol, 84%); MS (EI): m/z (rel. intensity) 358 (0.05, M$^+$); $^1$H NMR (DMSO-d$_6$) δ7.41 (s, 1H, Ar—H), 7.36 (s, 1H, Ar—H), 7.10 (t, 1H, NH, J=11.2 Hz), 5.94 (m, 1H, CH), 5.70 (d, 1H, CH, J=6.5 Hz), 5.25 (m, 3H, overlapping OH and $CH_2$), 5.09 (d, 1H, OH, J=8.8 Hz), 4.35 (m, 1H, CH), 3.98 (m, 2H, $CH_2$), 3.92 (m, 1H, CH), 3.81 (m, 1H, CH), 1.38 (d, 3H, $CH_3$, J=6.5 Hz).

Anal. Calcd. for $C_{15}H_{17}N_3O_3Cl_2$.0.2 $C_3H_7N$: C, 50.69; H, 5.02; N, 12.13. Found: C, 51.08; H, 4.83; N, 11.78.

Example 62

5,6-Dichloro-1-(5-deoxy-1-beta-D-ribofuranosyl)-N-(benzyl 1H-benzimidazol-2-amine Following General Procedure V, benzylamine (Aldrich, 5 mL, 45.77 mmol), and 2-bromo-5,6-dichloro-1-(5-deoxy-beta-D-ribofuranosyl)-1H-benzimidazole (250 mg, 0.65 mmol) reacted for 77 h. Additional benzyl amine (5 mL, 45.77 mmol) was added, and the reaction continued to stir at 80° C. for 9 days. Purification on a silica gel column with 1:1 ethyl acetate:hexanes gave the title compound (165 mg, 0.40 mmol, 62%); MS (EI): m/z (rel. intensity) 408 (0.05, M$^+$); $^1$H NMR (DMSO-d$_6$) δ7.48 (t, 1H, NH, J=11.7 Hz), 7.45–7.25 (m, 7H, Ar—H), 5.75 (d, 1H, CH, J=6.7 Hz), 5.31 (d,1H, OH, J=6.9 Hz), 5.26 (d, 1H, OH, J=4.7 Hz), 4.57 (d, 2H, $CH_2$, J=5.6 Hz), 4.38 (m, 1H, CH), 3.92 (m, 1H, CH), 3.82 (m, 1H, CH), 1.37 (d, 3H, $CH_3$, J=6.5 Hz).

Anal. Calcd. for $C_{19}H_{19}N_2O_3Cl_2$: C, 55.89; H, 4.69; N, 10.29. Found: C, 55.73; H, 4.79; N, 10.07.

Example 63

5,6-Dichloro-1-(5-deoxy-1-beta-D-ribofuranosyl)-N-(n-hexyl)-1H-benzimidazol-2-amine Following General Procedure V, n-hexyl amine (Aldrich, 5 mL, 37.85 mmol), and 2-bromo-5,6-dichloro-1-(5-deoxy-beta-D-ribofuranosyl)-1H-benzimidazole (250 mg, 0.65 mmol) were reacted for 5 h. Purification on a silica gel column with 1:1 ethyl acetate:hexanes gave the title compound (190 mg, 0.47 mmol, 69%); MS (EI): m/z (rel. intensity) 402 (0.30, M$^+$); $^1$H NMR (DMSO-$_6$) δ7.40 (s, 1H, Ar—H), 7.33 (s, 1H, Ar—H), 6.82 (t, 1H, NH, J=5.5 Hz), 5.66 (d, 1H, CH, J=6.6 Hz), 5.26 (d, 2H, OH, J=5.4 Hz), 4.33 (m,1H, CH), 3.92 (m,1H, CH), 3.80 (m, 1H, CH), 1.57 (m, 2H, $CH_2$), 1.38 (d, 3H, $CH_3$, J=6.3 Hz), 1.29 (m, 8H, $CH_2$), 0.87 (t, 3H, $CH_3$, J=13.2 Hz).

Anal. Calcd. for $C_{18}H_{25}N_2O_3Cl_2$: C, 53.74; H, 6.26; N, 10.44. Found: C, 53.49; H, 6.19; N, 10.35.

Example 64

5,6-Dichloro-1-(5-deoxy-beta-D-ribofuranosyl)-N-((R)-sec-butyl )-1H-benzimidazol-2-amine Following General Procedure V, (R)-sec-butylamine (Aldrich, 1.39 mL, 13.70 mmol), and 2-bromo-5,6-dichloro-1-(5-deoxy-beta-D-ribofuranosyl)-1H-benzimidazole (250 mg, 0.65 mmol) were reacted for 65 h. Additional (R)-sec-butylamine (1.39 mL, 13.70 mmol) was added, and the reaction continued to stir at 80° C. for 24 h. Purification on a silica gel column with 1:1 ethyl acetate:hexanes gave the title compound (130 mg, 0.35 mmol, 53%); MS (EI): m/z (rel. intensity) 374 (0.13, M$^+$); $^1$H NMR (DMSO-d$_6$) δ7.39 (s, 1H, Ar—H), 7.32 (s, 1H, Ar—H), 6.59 (d, 1H, NH, J=7.8 Hz), 5.72 (d, 1H, CH, J=6.6 Hz), 5.26 (m, 2H, overlapping OH), 4.27 (m, 1H, CH), 4.04–3.78 (m, 3H, overlapping CH), 1.61–1.51 (m, 2H, $CH_2$), 1.38 (d, 3H, $CH_3$, J=6.5 Hz), 1.17 (d, 3H, $CH_3$, J=6.5 Hz), 0.89 (t, 3H, $CH_3$, J=14.9 Hz).

Anal. Calcd. for $C_{16}H_{21}N_3O_3Cl_2$: C, 51.35; H, 5.66; N, 11.23. Found: C, 51.23; H, 5.74; N, 10.98.

Example 65

5,6-Dichloro-1-(5-deoxy-1-beta-D-ribofuranosyl)-N-((S)-sec-butyl)-1H-benzimidazol-2-amine Following General Procedure V, (S)-sec-butylamine (Aldrich, 1.37 mL, 13.67 mmol), and 2-bromo-5,6-dichloro-1-(5-deoxy-beta-D-ribofuranosyl)-1H-benzimidazole (230 mg, 0.60 mmol) were reacted for 46 h. Additional (S)-sec-butylamine (1.37 mL, 13.67 mmol) was added, and the reaction continued to stir at 80° C. for 45 h. Purification on a silica gel column with 1:15 methanol:$CH_2Cl_2$ gave the title compound (80 mg, 0.21 mmol, 36%); MS (EI): m/z (rel.

intensity) 374 (0.90, M+); $^1$H NMR (DMSO-d$_6$) δ7.45 (s, 1H, Ar—H), 7.35 (s, 1H, Ar—H), 6.51 (d, 1H, NH, J=7.2 Hz), 5.72 (d, 1H, CH, J=6.8 Hz), 5.28 (m, 2H, overlapping OH), 4.32 (m, 1H, CH), 4.04–3.80 (m, 3H, overlapping CH)1.64–1.48 (m, 2H, CH$_2$), 1.38 (d, 3H,CH$_3$, J=6.5 Hz), 1.17 (d, 3H, CH$_3$, J=6.5 Hz), 0.88 (t, 3H, CH$_3$, J=14.8 Hz).

Anal. Calcd. for C$_{16}$H$_{21}$N$_3$O$_3$Cl$_2$.0.5 CH$_4$O: C, 50.72; H, 5.97; N, 10.72. Found: C, 50.93; H, 5.71; N, 10.36.

Example 66

5,6-Dichloro-1-(5deoxy-beta-D-ribofuranosyl)-N-(1-methylethyl )-1H-benzimidazol-2-amine Following General Procedure V, isopropylamine (Aldrich, 3 mL, 34.92 mmol), and 2-bromo-5,6-dichloro-1-(5-deoxy-beta-D-ribofuranosyl)-1H-benzimidazole (200 mg, 0.52 mmol) were reacted for 16 h. Purification on a silica gel column with 1:15 methanol:CH$_2$Cl$_2$ gave 5,6-dichloro-1-(5-deoxy-beta-D-ribofuranosyl)-N-(1-methylethyl)-1H-benzimidazol-2-amine (168 mg, 0.47 mmol, 90%); MS (EI): m/z (rel. intensity) 360 (0.17, M+); 1H NMR (DMSO-d$_6$) δ7.41 (s, 1H, Ar—H), 7.32 (s,1H, Ar—H), 6.63 (d; 1H, NH, J=7.3 Hz), 5.73 (d, 1H, CH, J=6.6 Hz), 5.26 (m, 2H, 2 overlapping OH), 4.33 (m, 1H, CH), 4.01 (m, 1H, CH), 3.91 (m, 1H, CH), 3.81 (m, 1H, CH), 1.37 (d, 3H, CH$_3$, J=6.1 Hz), 1.21 (d, 6H, CH$_3$, J=6.3 Hz).

Anal. Calcd. for C$_{15}$H$_{19}$N$_3$O$_3$Cl$_2$.0.10H$_2$O: C, 47.85; H, 5.09; N, 11.16. Found: C, 48.14; H, 5.12; N, 10.92.

Example 67

5,6-Dichloro-2-(isopropoxy)-1-(5-deoxy-beta-D-ribofuranosyl)-1H-benzimidazole

Isopropyl alcohol (10 mL) was added to a tube containing NaH (dry) (Aldrich, 56 mg, 2.33 mmol) at 0° C. The solution was brought to rt and 2-bromo-5,6-dichloro-1-(5-deoxy-1-beta-D-ribofuranosyl)-1H-benzimidazole (250 mg, 0.65 mmol) was added. The tube was sealed and the solution stirred at rt for 4.5 h. The reaction was quenched with acetic acid (0.133 mL, 3.12 mmol). The reaction mixture was concentrated, dissolved in ethyl acetate (25 mL) and washed with saturated NaHCO3 (10 mL), followed by water (2×10 mL). The ethyl acetate layer was dried with magnesium sulfate (anhyd), filtered, and evaporated. The crude residue was purified on a silica gel column with 1:1 ethyl acetate-:hexanes. The resulting product was further purified on a silica gel column with 1:2 ethyl acetate:hexanes to give 5,6-dichloro-2-(isopropoxy)-1-(5-deoxy-1-beta-D-ribofuranosyl)-1H-benzimidazole (18 mg, 0.05 mmol, 10%); MS (EI): m/z (rel. intensity) 243 (1.00, M+−117); $^1$H NMR (DMSO-d$_6$) δ7.68 (d, 2H, Ar—H, J=5.1 Hz), 5.69 (d, 1H, CH, J=5.6 Hz), 5.38 (d, 1H, OH, J=5.8 Hz), 5.28 (m, 1H, CH), 5.16 (d, 1H, OH, J=5.3 Hz), 4.48 (m, 1H, CH), 4.04–3.84 (m, 2H, CH), 1.41 (m, 6H, CH$_3$), 1.31 (d, 3H, CH$_3$, J=6.2 Hz)

Example 68

2,4,5,6-Tetrachloro-1-(2,3-di-O-acetyl-5-deoxy-beta-D-ribofuranosyl)-1H-benzimidazole A mixture of 2,4,5,6-tetrachloro-1H-benzimidazole (1.02 g, 4.0 mmol), acetonitrile (20 mL), and N,O-bis (trimethylsilyl)acetamide (1.5 mL, 6 mmol) was stirred at 70° C. for 15 min. Then 1,2,3-tri-O-acetyl-5-deoxy-D-ribofuranose (1.35 g, 5.2 mmol) in acetonitrile (5 mL) was added, followed by trimethylsilyltrifluoromethane sulfonate (1.16 mL, 6.0 mmol). The resulting mixture was allowed to stir at 70° C. for 20 min. Another portion of 1,2,3-tri-O-acetyl-5-deoxy-D-ribofuranose (0.21 g, 0.8 mmol) in acetonitrile (2 mL) was added and stirring was continued at 70° C. for 10 min. The mixture was allowed to cool to RT and was diluted with ethyl acetate. The ethyl acetate layer was washed with a saturated NaHCO$_3$/NaCl solution, dried over Na$_2$SO$_4$ and the solvents were removed by rotary evaporation. The product was purified by flash chromatography using chloroform as eluant. Recrystallization from methanol afforded 1.11 g (61 %) of the title compound as white crystals; m.p. 126–127° C.; $^1$H NMR (DMSO-d$_6$) δ: 8.16 (s, 1H), 6.20 (d, 1H), 5.61 (t, 1H), 5.25 (dd, 1H), 4.24 (m, 1H), 2.13 (s, 3H), 2.02 (s, 3H), 1.50 (d, 3H).

Anal. (C$_{16}$H$_{14}$Cl$_4$N$_2$O$_5$): C, H, N.

Example 69

2-Bromo4,5,6-trichloro-1-(2,3-di-O-acetyl-5-deoxy-beta-D-ribofuranosyl )-1H-benzimidazole 2-Bromo4,5,6-trichloro-1H-benzimidazole (0.3 g, 1 mmol), acetonitrile (10 mL), and N,O-bis(trimethylsilyl) acetamide were stirred at 70° C. for 15 min., giving a homogeneous solution. To the solution was then added 1,2,3-tri-O-acetyl-5-deoxyribofuranose (0.31 g, 1.2 mmol) in acetonitrile (5 mL) and trimethylsilyltrifluoromethane sulfonate (0.25 mL, 1.3 mmol). The resulting mixture was allowed to stir at 70° C. for 20 min. The mixture was then allowed to cool to RT and was diluted with ethyl acetate and was washed with a saturated aqueous NaHCO$_3$ solution, dried over NaSO$_4$ and the solvents were removed by rotary evaporation. The product was purified by flash chromatography using chloroform as eluent and then recrystallization from methanol afforded 0.29 g (58%) of the title compound as white crystals; m.p. 160–162° C.; $^1$H NMR (DMSO-d$_6$) δ: 8.14 (s, 1H), 6.16 (d, 1H), 5.63 (t, 1H), 5.27 (dd, 1H), 4.26 (m, 1H), 2.13 (s, 3H), 2.02 (s, 3H), 1.51 (d, 3H).

Anal. (C$_{16}$H$_{14}$BrCl$_3$N$_2$O$_5$): C, H, N.

Example 70

4-Bromo-2,5,6-trichloro-1-(2,3-di-O-acetyl-5-deoxy-beta-D-ribofuranosyl)-1H-benzimidazole To a suspension of 4-bromo-2,5,6-trichloro-1H-benzimidazole (0.30 g, 1 mmol), in acetonitrile (5 mL) was added N,O-bis(trimethylsilyl)acetamide (0.25 mL, 1 mmol). The resulting mixture was allowed to stir at 65° C. for 15 min., followed by the addition of 1,2,3-tri-O-acetyl-5-deoxyribofuranose (0.31 g, 1.2 mmol) in acetonitrile (5 mL) and trimethylsilyltrifluoromethane sulfonate (0.25 mL, 1.3 mmol). The mixture was allowed to stir at 65° C. for 20 min and was then allowed to cool to RT. The mixture was diluted with ethyl acetate and was washed with a saturated NaHCO$_3$/NaCl solution, dried over MgSO$_4$ and the solvents were removed by rotary evaporation. The product was purified by flash chromatography using chloroform as eluent followed by recrystallization from methanol to provide 0.28 g (55%) of the title compound as white crystals; m.p. 138–141° C.; $^1$H NMR (DMSO-d$_6$) δ: 8.18 (s, 1H), 6.19 (d, 1H), 5.61 (dd, 1H), 5.25 (dd, 1H), 4.24 (m, 1H), 2.14 (s, 3H), 2.02 (s, 3H), 1.50 (d, 3H).

Anal. (C$_{16}$H$_{14}$BrCl$_3$N$_2$O$_5$): C, H, N.

Example 71

2,4-Dibromo-5,6-dichloro-1-(2,3-di-O-acetyl-5-deoxy-beta-D-ribofuranosyl)-1H-benzimidazole To a suspension of 2,4-dibromo-5,6-dichloro-1H-benzimidazole (0.35 g, 1 mmol), in acetonitrile (5 mL) was added N,O-bis(trimethylsilyl)acetamide (0.25 mL, 1 mmol). The resulting mixture was allowed to stir at 70° C. for 15 min, followed by the addition of 1,2,3-tri-O-acetyl-5-deoxyribofuranose (0.31 g, 1.2 mmol) in acetonitrile (5 mL) and trimethylsilyltrifluoromethane sulfonate (0.25 mL, 1.3 mmol). The mixture was allowed to stir at 70° C. for 30 min and was then allowed to cool to RT. The mixture was diluted with ethyl acetate, washed with a saturated aqueous NaHCO$_3$ solution, dried over NaSO$_4$ and the solvents were removed by rotary evaporation. The product was purified by flash chromatography using methylene chloride then 1:1 methylene chloride/chloroform followed by recrystallization from methanol to provide 0.35 g (63%) of the title compound as white crystals: m.p. 152–154° C.; $^1$H NMR (DMSO-d$_6$) δ: 8.16 (s, 1H), 6.15 (d, 1H), 5.63 (t, 1H), 5.27 (dd, 1H), 4.26 (m, 1H), 2.13 (s, 3H), 2.02 (s, 3H), 1.51 (d, 3H).

Anal. (C$_{16}$H$_{14}$Br$_2$Cl$_2$N$_2$O$_5$): C, H, N.

Example 72

2,5,6-Trichloro-1-(5-deoxy-α-D-lyxofuranosyl)1H-benzimidazole (4)

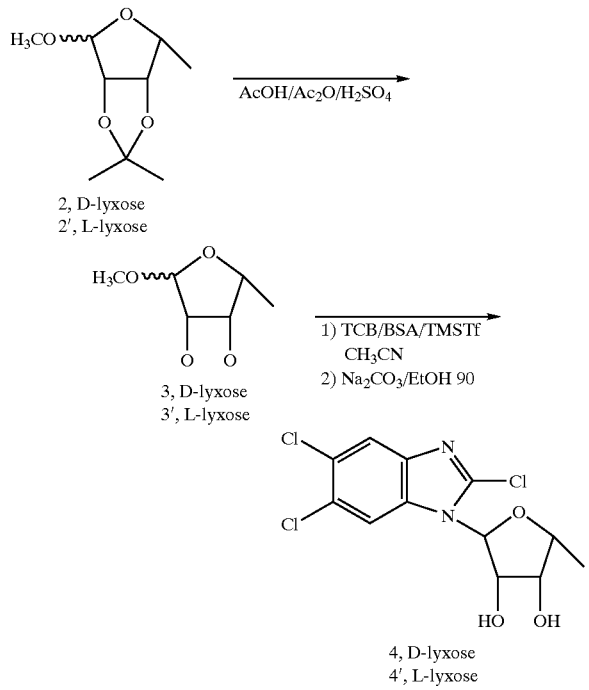

2, D-lyxose
2', L-lyxose

3, D-lyxose
3', L-lyxose

4, D-lyxose
4', L-lyxose

A. 1-O-methyl-2,3-di-O-Isopropylidene-5-deoxy-D-lyxofuranose(2)

Compound 2 was prepared according to Lerner, L. M., *Carbohydrate Research* 53,177–185 (1977).

$^1$H NMR (DMSO-d$_6$): δ(ppm); 4.86 (s, 1H, H-1), 4.6 (m, 2H, H-2 and H-3), 4.1 (m, 1H, H-4), 3.34 (s, 3H, OCH$_3$), 1.48 and 1.34 (2s, 6H (CH$_3$)$_2$), 1.34 (d, 3H, J-5.8 Hz, H-5, 5', 5'').

1-O-methyl-2,3-di-O-isopropylidene-5-deoxy-L-lyxofuranose (2')

Compound 2' was prepared according to Hulyalkar, R. K. and Perry, M. B., *Canadian Journal of Chemistry* 43, 3244–3246 (1965).

NMR as for Compound 2, Yield: 78%.

B. 1,2,3-Tri-O-acetyl-5-deoxy-D-lyxofuranose (3)

A solution of 2 (480 mg, 2.55 mmol) in a mixture of acetic acid (12 ml) and acetic anhydride (1.2 ml) was stirred at 0° C. Sulfuric acid (660 μl) was added over 30 min. The icy mixture was allowed to reach room temperature and after 20 h of stirring, poured into icy water (50 ml) and diluted with ethyl acetate (100 ml). The aqueous layer was washed 3 times with dichloromethane, and the organic layers were combined and washed with a saturated aqueous solution of sodium bicarbonate, then with water. The organic layer was dried over sodium sulfate, filtered and evaporated under reduced pressure to afford 3 (63%) as an oil, slightly contaminated by a linear side product (≦6%).

1,2,3-Tri-O-acetyl-5-deoxy-L-lyxofuranose (3')

Same experimental procedure as above; same NMR, Yield: 68%.

C. 2,5,6-Trichloro-1-(5-deoxy-α-D-lyxofuranosyl)-1H-benzimidazole (4)

2,5,6-Trichlorobenzimidazole (221 mg, 1.0 mmol) was suspended in acetonitrile (15 ml) and the mixture was stirred at 40° C. BSA (365 μl, 1.5 mmol) was added, and the reaction mixture stirred for 15 min. A solution of 3 (260 mg, 1.0 mmol) in acetonitrile (5 ml) and TMSOTf (290 μl, 1.5 mmol) was added to the clear solution, and the mixture was allowed to stand at room temperature for 18 hours. The mixture was concentrated under reduced pressure, and the residue was dissolved with dichloromethane (50 ml). The solution was washed with a saturated aqueous solution of sodium bicarbonate (10 ml) and with water (3×10 ml), dried over anhydrous sodium sulfate, filtered and concentrated under reduced pressure. The residue was taken up with the minimum amount of dichloromethane and chromatographed on a silica gel column (eluent: gradient of methanol (0–1.6%) in dichloromethane). Fractions having a UV-absorbing spot that also charred under H$_2$SO$_4$ and heating were pooled and concentrated to a foam which was dissolved in ethanol 90 (11 ml). To the stirred solution was added sodium carbonate (216 mg, 2.0 mmol) and the reaction mixture was stirred overnight. The mixture was then evaporated under reduced pressure, dissolved in a 2:1 mixture of ethyl acetate and dichloromethane, and washed with water. The organic layer was dried over sodium sulfate, filtered and evaporated under reduced pressure. Compound 4 crystallized from a 2% methanolic solution of dichloromethane (120 mg, 56%).

mp: 118–120° C.; $^1$H NMR (DMSO-d$_6$): δ8.39 and 7.96 (2s, 2H, H-4 and H-7), 5.95 (d, 1H, J=4.9 Hz, OH-2'), 5.7 (m, 2H, H-1' and OH-3'), 4.3–4.2 (m, 2H, H-2' and H-4'), 3.9 (m, 1H, H-3'), 1.30 (d, 3H, J=6.3 Hz, H-5', 5", 5'''); Analysis calcd for C$_{12}$H$_{11}$Cl$_3$N$_2$O$_3$; C, 42.69; H, 3.28, N, 8.30. Found: C, 42.94; H, 3.35; N, 8.43.

2,5,6-Trichloro-1-(5-deoxy-α-L-lyxofuranosyl)-1H-benzimidazole (4')

Same experimental procedure, same NMR. Yield: 48% (based on consumed heterocycle); mp: 120–122° C.; Analysis calcd for C$_{12}$H$_{11}$Cl$_3$N$_2$O$_3$: C, 42.69; H, 3.28, N, 8.30, Found: C, 42.85; H, 3.36; N, 8.23.

Example 73

2-Bromo-5,6-dichloro-1-(5-deoxy-β-D-ribofuranosyl)benzimidazole (4a)

A. 2-Bromo-5,6-dichloro-1-(5-deoxy-2,3-di-O-acetyl-β-D-ribofuranosyl)benzimidazole (2b) and 2-Bromo-5,6-dichloro-1-(5-deoxy-2,3-di-O-acetyl-α-D-ribofuranosyl)-1H-benzimidazole (3b)

To a stirred suspension of 2-bromo-5,6-dichlorobenzimidazole (which may be made according to U.S. Pat. No. 5,248,672) (1b, 1.33 g, 5 mmol) in dry MeCN (25 ml) was added 1.8 mL (7.5 mmol) of BSA. The reaction mixture was stirred at room temperature for 15 min to give a clear solution. This solution was treated with a solution of 5-deoxy-1,2,3-tri-O-acetyl-D-ribofuranose (1.4 g, 5.5 mmol) in dry acetonitrile (5 mL) and 1.3 mL (6.5 mmol) of TMSOTf at room temperature for 30 min. A fresh solution of 5-deoxy-1,2,3-tri-O-acetyl-D-fibofuranose (0.26 g, 1 mmol) in dry MeCn (2 mL) was added and stirring was continued at room temperature for 30 minutes. The reaction mixture was diluted with EtOAc (100 mL). The EtOAc solution was washed with a sat. NaHCO$_3$ solution (100 mL×2), dried (Na$_2$SO$_4$), and evaporated. The residue was recrystallized from MeOH to give 1.2 g (53%) of 2b as white crystals. The mother liquor was evaporated and the residue was chromatographed on a silica column (2.2×35 cm, eluted with CHCl$_3$). Evaporation of fractions 16–42 (20 mL per fraction) and recrystallization from MeOH gave an additional 0.6 g (27%) of 2b as white crystals. The total yield of 2b was 1.86 g (80%). MP: 145–148° C. HRMS: (EI, with DCI probe) m/z 463.9582 (6%, M$^+$=463.9541). $^1$H NMR (DMSO-$\underline{d}_6$): 8.11 (s, 1, 7-H), 7.99 (s, 1, 4-H), 6.14 (d, 1, 1'-H, J$_{1'-2'}$=6.5 Hz), 5.65 (t, 1, 2'-H, J$_{2',3'}$=7.0 Hz), 5.27 (dd, 1, 3'-H, J$_{3'-4'}$=5.5 Hz), 4.25 (m, 1, 4'-H, J$_{4'-5'}$=6.5 Hz), 2.13, 2.02 (2×s, 6, 2×Ac), 1.51 (d, 3, 5'-H). $^{13}$C NMR (DMSO-$\underline{d}_6$): δ169.61, 168.20, (2×$\underline{C}$OCH$_3$), 142.28 (C3a), 132.80 (C7A), 131.49 (C2),126.35, 126.07 (C5 and C6), 120.22 (C4), 113.37 (C7), 87.93 (C1'), 77.98 (C4'), 72.89 (C3'), 70.91 (C2'), 20.33, 20.07 (2×CO$\underline{C}$H$_3$), 17.78 (C5'). Anal. (C$_{16}$H$_{15}$BrCl$_2$N$_2$O$_5$) C, H, N. Evaporation of fractions 45–58 gave 0.38 g of 3b which was further purified on a silica column (2.2×8 cm, eluted with hexane, 30% EtOAc/hexane). Evaporation of fractions 9–12 (20 mL per fraction) gave 0.26 g (11 %) of 3b as a colorless syrup. HRMS: (EI) m/z 463.9529 (2%, M$^+$=463.9541). $^1$H NMR (DMSO-dhd 6): δ7.95 (s,1, 4-H), 7.89 (s, 1, 7-H), 6.68 (d, 1, 1'-H,J$_{1'-2'}$=4.5 Hz), 5.70 (t, 1, 2'-H, J$_{2'-3'}$=5.0 Hz), 5.28 (dd, 1, 3'-H, J$_{3'-4'}$=7.0 Hz), 4.72 (m, 1, 4'-H, J$_{4'-5'}$=6.5 Hz), 2.03, 1.51 (2×s, 6, 2×Ac), 1.39 (d, 3, 5'-H). $^{13}$C NMR (DMSO-$\underline{d}_6$): δ169.46, 168.30, (2×$\underline{C}$OCH$_3$), 142.13 (C3a), 133.58 (C7a), 131.10 (C2), 125.74, 125.42 (C5 and C6), 119.95 (C4), 114.24 (C7), 86.87 (C1'), 76.89 (C4'), 74.55 (C3'), 71.18 (C2'), 20.21, 19.58 (2×CO$\underline{C}$H$_3$), 18.12 (C5').

B. 2-Bromo-5,6-dichloro-1-(5-deoxy-β-D-ribofuranosyl)-1H-benzimidazole (4a)

To a stirred solution of Na$_2$CO$_3$ (0.325 g, 3 mmol) in H$_2$O (10 mL), were added successively 45 mL of EtOH, 45 mL of MeOH, and 0.46 g (1 mmol) of 2b. Stirring was continued at room temperature for 2 h. The reaction mixture was neutralized with glacial AcOH and then concentrated to about 10 mL. The yellow, oily residue was triturated with H$_2$O (10 mL) and the resulting yellow precipitate was collected by filtration. This precipitate was dissolved in EtOH, decolorized with charcoal, and recrystallized from H$_2$O/EtOH/dioxane. Final recrystallization from H$_2$O gave 0.206 g (61 %) of 4a. MP: 85–86° C. MS: (EI, with DCI probe) m/z 336 (4, M$^+$=336). $^1$H NMR (DMSO-$\underline{d}_6$): δ7.99 (s, 1, 4-H), 7.89 (s, 1, 7-H), 5.87 (d, 1, 1-H, J$_{1'-2'}$=6.5 Hz), 5.53 (d, 1, 2'-OH, J$_{2'-2'}$=6.0 Hz), 5.28 (d, 1, 3'-OH, J$_{3'-3'OH}$= 5.0 Hz), 4.49 (m, 1, 2'-H, J$_{2'-3'}$=6.0 Hz), 4.00 (M, 1, 4'-H, J$_{3'-4'}$=4.0 Hz, J$_{4'-5'}$=6.5 Hz), 3.89 (m, 1, 3'-H), 1.41 (d, 3, 5'-H). $^{13}$C NMR (DMSO-$\underline{d}_6$): δ142.09 (C2), 141.03 (C3a), 132.68 (C7a), 126.14, 125.93 (C5 and C6), 120.40 (C4), 113.42 (C7), 90.02 (C1'), 80.97 (C4'), 73.80 (C3'), 71.71 (C2'), 18.88 (C5'). Anal. (C$_{12}$H$_{11}$Cl$_3$N$_2$O$_3$) C, H, N.

Example 74

2-Bromo-5,6-dichloro-1-(5-deoxy-β-D-ribofuranosyl1H-benzimidazole (4b)

To a stirred solution of Na$_2$CO$_3$ (0.027 g, 0.25 mmol) in H$_2$O (1 mL), were added successively 4.5 mL of EtOH, 4.5 mL of MeOH, and 0.233 g (0.5 mmol) of 2b. The reaction mixture was stirred at room temperature for 1 h. AcOH (0.015 mL) was added and stirring was continued at room temperature for 10 min. Volatile materials were removed by evaporation (bath temperature <25° C.). The residue was dissolved in a small amount of EtOAc and absorbed onto silica. This was dried and placed onto a silica column (2.2×15 cm, eluted with CHCl$_3$, 30%, 50% EtOAc/CHCl$_3$ v/v). Evaporation of fractions 15–37 (20 mL per fraction) and recrystallization from MeCN gave 0.157 g (3 crops, 82%) of 4b as white crystals {the third crop (0.020 g) was obtained by recrystallization from MeCN/H$_2$O}. MP: 133–135° C. HRMS: (EI, with DCI probe) m/z 379.9338 (4%, M$^+$=379.9330). $^1$H NMR (DMSO-$\underline{d}_6$): δ7.99 (s, 1, 4-H), 7.86 (s, 1, 7-H), 5.86 (d, 1,1-H, J$_{1'-2'}$=7.0 Hz), 5.51 (d, 1,2'-OH, J$_{2'-2'OH}$=6.0 Hz), 5.29 (d, 1,3'-OH, J$_{3'-3'OH, J}$=5.0 Hz), 4.50 (m, 1,2'-H, J$_{2'-3'}$=6.0 Hz), 4.01 (M, 1, 4'-H, J$_{3'-4'}$=4.0 Hz, J$_{4'-5'}$=6.5 Hz) 3.90 (m, 1,3'-H), 1.42 (d, 3 5'-H). $^{13}$C NMR (DMSO-$\underline{d}_6$): δ142.61 (C3a), 132.70 (C7a), 132.50 (C2), 125.87, 125.73 (C5 and C6), 120.23 (C4), 113.24 (C7), 90.82 (C1'), 80.91 (C4'), 73.70 (C3'), 71.43 (C2'), 18.91 (C5'). Anal. (C$_{12}$H$_{11}$BrCl$_2$N$_2$O$_3$) C, H, N.

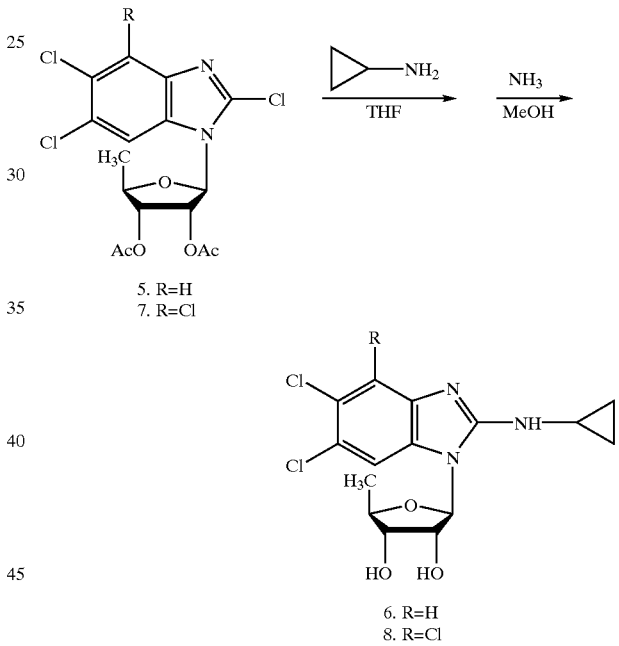

5. R=H
7. R=Cl

6. R=H
8. R=Cl

Example 75

2-Cyclopropylamino-5,6-dichloro-1-(5-deoxy-β-D-ribofuranosyl)-1H-benzimidazole (6)

A mixture of 5 (0.422 g, 1 mmol) and cyclopropylamine (0.694 mL, 10 mmol) in THF (10 mL) was stirred at room temperature for 18 days (with the addition of 0.694 mL of fresh cyclopropylamine on the 9th day). Volatile materials were removed by evaporation and the residue was treated with NH$_3$/MeOH (15 mL, sat. at 0° C.) at room temperature for 18 h. The reaction mixture was again evaporated and the residue was chromatographed on a silica column (2×15 cm, eluted successively with CHCl$_3$, 4%, 8% MeOH/CHCL$_3$, v/v). Evaporation of fractions 23~35 (15 mL per fraction) and recrystallization from MeCN gave 0.296 g (83%) of 6 as white crystals. MP: ~210° C. (dec). HRMS: (EI, with DCI probe) m/z 357.0645 (51%, M$^+$=357.0647). $^1$H NMR (DMSO-d-$_6$): δ7.48 (s, 1, 4-H), 7.35 (s,1,7-H), 7.14 (d, 1,2'-NH—, J$_{2'NH-1Cp}$=2 Hz), 5.62 (d, 1,1'-H, J$_{1'-2'}$=6.5 Hz), 5.26 (d, 1,3'-OH, J$_{3'-3'OH}$=4.5 Hz), 5.23 (d,1, 2'-OH, J$_{2'-2'OH}$=7.0 Hz),4.33 (m, 1,2'-H, J$_{2'-3'}$=5.5 Hz), 3.90 (m, 1,4'H, J$_{4'-3'}$=4.5 Hz, J$_{4'-5'}$=6.5 hz), 3.79 (m, 1, 3'-HO, 2.76 (m, 1,1,-Cp), 1.37 (d, 3,5'-H), 0.71, 0.53 (2×m, 4, 2-Cp and 3-Cp). $^{13}$C NMR (DMSO-d-$_6$): δ156.68 (C2), 143.53 (C3a), 132.05 (C7a), 123.27, 120.22 (C5 and C6), 116.38 (C4), 111.05 (C7), 87.56 (C1'), 80.00 (C4'), 73.65 (C3'), 70.85 (C2'), 25.17 (1-Cp), 18.93 (C5") 6.49, 6.15 (2-Cp and 3-Cp). Anal. Calcd. for C$_{15}$H$_{17}$Cl$_2$N$_3$O$_3$: C, 50.29, H, 4.78, N, 11.73. Found C, 50.42, H, 5.00, N, 11.99.

Example 76

2- Cyclopropylamino-4,5,6-trichloro-1-(5-deoxy-β-D-ribofuranosyl)-1H-benzimidazole (8)

A mixture of 7 (0.228 g, 0.5 mmol) and cyclopropylamine (0.346 mL, 5 mmol) in THF (5 mL) was stirred at room temperature for 7 days. Volatile materials were removed by evaporation and the residue was treated with NH$_3$/MeOH (10 mL, sat. at 0° C.) at room temperature for 4 h. The reaction mixture was again evaporated. The residue was coevaporated with toluene (3×), MeOH (2×), MeCN (2×), and then recrystallized from MeCN to give 0.128 g (65%) of 8 as white crystals. MP: ~195° C. (dec). HRMS: (EI, with DCI probe) m/z 391.0269 (29%, M$^+$=391.0257). $^1$H NMR (DMSO-d-$_6$): δ7.37 (s, 1,7-H), 7.28 (d, 1,2-NH- J$_{2NH-1Cp}$= 2.5 Hz), 5.64 (d,1, 1-H, J$_{1'-2'}$=7.0 Hz), 5.26 (d,1,3'-OH, J$_{3'-3'OH}$=4.5 Hz), 5.24 (d, 1, 2-OH, J$_{2'-2'OH}$7.0 Hz), 4.32 (m, 1, 2'H, J$_{2'-3'}$=6.0 Hz), 3.92 (m, 1, 4'-H, J$_{4'-3'}$=4.0 Hz, J$_{4'-5'}$=6.5 Hz), 3.80 (m, 1, 3'H), 2.85 (m, 1, 1,-Cp), 1.37 (d, 3,5'-H), 0.73, 0.56 (2×m, 4, 2-Cp and 3-Cp). $^{13}$C NMR (DMSO-d-$_6$): δ156.81 (C2), 141.08 (C3a), 131.64 (C7a), 121.96, 121.32 (C5 and C6), 118.62 (C4), 109.91 (C7), 80.30 (C4'), 73.55 (C3'), 70.97 (C2'), 25.24 (1-Cp), 18.93 (C5'), 6.48, 6.15 (2-Cp and 3-Cp). Anal. Calcd. for C$_{15}$H$_{16}$Cl$_3$N$_3$O$_3$: C, 45.88, H, 4.11, N. 10.70. Found C, 45.91, H, 4.29, N, 10.57.

Example 77

Tablet Formulation

The following formulations A, B and C are prepared by wet granulation of the ingredients with a solution of povidone, followed by addition of magnesium stearate and compression.

| Formulation A | mg/tablet |
|---|---|
| Active Ingredient | 250 |
| Lactose B.P. | 210 |
| Povidone B.P. | 15 |
| Sodium Starch Glycolate | 20 |
| Magnesium Stearate | 5 |
| | 500 |

| Formulation B | |
|---|---|
| Active Ingredient | 250 |
| Lactose B.P. | 150 |
| Avicel PH 101 | 60 |
| Povidone B.P. | 15 |
| Sodium Starch Glycolate | 20 |
| Magnesium Stearate | 5 |
| | 500 |

| Formulation C | |
|---|---|
| Active Ingredient | 250 |
| Lactose B.P. | 200 |
| Starch | 50 |
| Povidone | 5 |
| Magnesium Stearate | 4 |
| | 359 |

The following formulations, D and E, are prepared by direct compression of the admixed ingredients. The lactose in formulation E is of the direct compression type (Dairy Crest—"Zeparox").

| Formulation D | mg/tablet |
|---|---|
| Active Ingredient | 250 |
| Pregelatinized Starch NF15 | 150 |
| | 400 |

| Formulation E | |
|---|---|
| Active Ingredient | 250 |
| Lactose B.P. | 150 |
| Avicel | 100 |
| | 500 |

Formulation F (Controlled Release Formulation)

The formulation is prepared by wet granulation of the ingredients with a solution of povidone followed by the addition of magnesium stearate and compression.

| | mg/tablet |
|---|---|
| Active Ingredient | 500 |
| Hydroxypropylmethyl cellulose (Methocel K4M Premium) | 112 |
| Lactose B.P. | 53 |
| Povidone B.P. | 28 |
| Magnesium Stearate | 7 |
| | 700 |

Drug release takes place over a period of about 6–8 hours and is complete after 12 hours.

Example 78

Capsule Formulations

Formulation A

A capsule formulation is prepared by admixing the ingredients of formulation D in Example 1 above and filling into a two-part hard gelatin capsule. Formulation B (infra) is prepared in a similar manner.

|  | mg/capsule |
| --- | --- |
| Formulation B | |
| Active ingredient | 250 |
| Lactose B.P. | 143 |
| Sodium Starch Glycollate | 25 |
| Magnesium Stearate | 2 |
|  | 420 |
| Formulation C | |
| Active Ingredient | 250 |
| Macrogel 4000 B.P. | 350 |
|  | 600 |

Capsules of formulation C are prepared by melting the Macrogel 4000 B.P., dispersing the active ingredient in the melt and filling the melt into a two-part hard gelatin capsule.

| Formulation D | mg/capsule |
| --- | --- |
| Active Ingredient | 250 |
| Lecithin | 100 |
| Arachis Oil | 100 |
|  | 450 |

Capsules of formulation D are prepared by dispersing the active ingredient in the lecithin and arachis oil and filling the dispersion into soft, elastic gelatin capsules.

| Formulation E | mg/capsule |
| --- | --- |
| Active Ingredient | 150.0 |
| Vitamin E TPGS | 400.0 |
| Polyethylene Glycol 400 NF | 200.5 |
| Propylene Glycol USP | 39.5 |

Four (4) kilograms (kg) of Vitamin E TPGS (obtained from Eastman Chemical Co.) was heated at 50° C. until liquefied. To the liquefied Vitamin E TPGS, 2.005 kg of polyethylene glycol 400 (PEG400) (low aldehyde, <10 ppm, obtained from Union Carbide or Dow Chemical Co.) heated to 50° C. was added and mixed until a homogeneous solution was formed. The resultant solution was heated to 65° C. 1.5 kg of active ingredient was dissolved in the liquefied solution of Vitamin E TPGS and PEG 400. 0.395 kg of propylene glycol at room temperature was added and mixed until a homogenous solution was formed. The solution was cooled to 28–35° C. The solution was then de-gassed. The mixture was preferably encapsulated at 28–35° C. at a fill weight equivalent to 150 mg of volatiles-free compound, into Size 12 oblong, white opaque soft gelatin capsules using a capsule filling machine. The capsule shells were dried to a constant fill moisture of 3–6% water and a shell hardness of 7–10 newtons, and placed in a suitable container.
Formulation F (Controlled Release Capsule)
The following controlled release capsule formulation is prepared by extruding ingredients a, b, and c using an extruder, followed by spheronization of the extrudate and drying. The dried pellets are then coated with release-controlling membrane (d) and filled into a two-piece, hard gelatin capsule.

|  | mg/capsule |
| --- | --- |
| (a) Active Ingredient | 250 |
| (b) Microcrystalline Cellulose | 125 |
| (c) Lactose B.P. | 125 |
| (d) Ethyl Cellulose | 13 |
|  | 513 |

Example 79

Injectable Formulation

| Formulation A | mg |
| --- | --- |
| Active Ingredient | 200 |
| Hydro chloric Acid Solution 0.1M or Sodium Hydroxide Solution 0.1M q.s. to pH | 4.0 to 7.0 |
| Sterile water q.s. to | 10 ml |

The active ingredient is dissolved in most of the water (35°–40° C.) and the pH adjusted to between 4.0 and 7.0 with the hydrochloric acid or the sodium hydroxide as appropriate. The batch is then made up to volume with water and filtered through a sterile micropore filter into a sterile 10 ml amber glass vial (type 1) and sealed with sterile closures and overseals.

| Formulation B | |
| --- | --- |
| Active Ingredient | 125 mg |
| Sterile, Pyrogen-free, pH 7 Phosphate Buffer, q.s. to | 25 ml |

Example 80

Intramuscular Injection

| Active Ingredient | 200 mg |
| --- | --- |
| Benzyl Alcohol | 0.10 g |
| Glycofurol 75 | 1.45 g |
| Water for injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml amber glass vials (type 1).

Example 81

Syrup

| Active Ingredient | 250 mg |
| --- | --- |
| Sorbitol Solution | 1.50 g |
| Glycerol | 2.00 g |
| Sodium Benzoate | 0.005 g |

-continued

| | |
|---|---|
| Flavor, Peach 17.42.3169 | 0.0125 ml |
| Purified Water q.s. to | 5.00 ml |

The active ingredient is dissolved in a mixture of the glycerol and most of the purified water. An aqueous solution of the sodium benzoate is then added to the solution, followed by addition of the sorbital solution and finally the flavor. The volume is made up with purified water and mixed well.

Example 82

Suppository

| | mg/capsule suppository |
|---|---|
| Active Ingredient | 250 |
| Hard Fat, B.P. (Witepsol H15-Dynamit Nobel) | 1770 |
| | 2020 |

One-fifth of the Witepsol H15 is melted in a steam-jacketed pan at 45° C. maximum. The active ingredient is sifted through a 200 μm sieve and added to the molten base with mixing, using a Silverson fitted with a cutting head, until a smooth dispersion is achieved. Maintaining the mixture at 45° C., the remaining Witepsol H15 is added to the suspension and stirred to ensure a homogenous mix. The entire suspension is passed through a 250 μm stainless steel screen and, with continuous stirring, is allowed to cool to 45° C. At a temperature of 38° C. to 40° C., 2.02 g of the mixture is filled into suitable, 2 ml plastic molds. The suppositories are allowed to cool to room temperature.

Example 83

Pessaries

| | mg/pessary |
|---|---|
| Active Ingredient | 250 |
| Anhydrate Dextrose | 380 |
| Potato Starch | 363 |
| Magnesium Stearate | 7 |
| | 1000 |

The above ingredients are mixed directly.

Example 84

Human Cytomegalovirus Assay

HCMV strain AD169 was grown on monolayers of human embryonic lung cells (MRC5 cells) in 96 well plates. After infection of the cells at a ratio of approximately 0.01 infectious virus particles per cell; the compounds to be tested were added to selected wells at six different concentrations, each in triplicate. The same concentrations of compounds were also applied to wells containing monolayers of uninfected cells in order to assess compound cytotoxicity. The plates were incubated for 5 days, and the minimum cytotoxic dose was estimated from microscopic examination. The IC50 for antiviral effect was estimated from measurements of HCMV DNA in each well by blotting and quantitative specific DNA hybridization, similar to the method of Gadler (Antimicrob. Agents Chemother. 1983, 24, 370–374). Data for representative compounds follows:

| Example | HCMV IC50 |
|---|---|
| Example 9 | 6.9 μM |
| Example 12 | 3.5 μM |
| Example 44 | 7.0 μM |
| Example 46 | 6.1 μM |
| Example 50 | 7.0 μM |
| Example 59 | 1.1 μM |

What is claimed is:
1. A compound of formula (I):

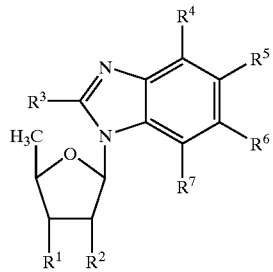

(I)

wherein:

$R_1$ is hydroxy; O-acetyl; or a halo atom;

$R^2$ is hydroxy; O-acetyl; or a halo atom;

$R^3$ is hydrogen; a halo atom; azido; $C_{2-6}$alkenyl; $C_{2-6}$alkynyl; $C_{6-14}$aryl $C_{2-6}$alkenyl; $C_{6-14}$aryl$C_{2-6}$ alkynyl —$NR^8R^9$ (where $R^8$ and $R^9$ are the same or different and are hydrogen, $C_{1-8}$alkyl, cyano$C_{1-8}$alkyl, hydroxy$C_{1-8}$alkyl, halo$C_{1-8}$alkyl, $C_{3-7}$cycloalkyl, $C_{1-8}$alkyl$C_{3-7}$cycloalkyl, $C_{2-6}$alkenyl, $C_{3-7}$cycloalkyl$C_{1-8}$alkyl, $C_{2-6}$alkynyl, $C_{6-14}$aryl, $C_{6-14}$aryl$C_{1-8}$alkyl, heterocycle$C_{1-8}$alkyl, $C_{1-8}$alkylcarbonyl, $C_{6-14}$arylsulfonyl, $C_{1-8}$alkysulfonyl, or $R^8R^9$ together with the N atom to which they are attached form a 3,4,5 or 6 membered heterocyclic ring); —$OR^{10}$ (where $R^{10}$ is hydrogen, $C_{1-8}$alkyl, $C_{6-14}$aryl, or $C_{6-14}$aryl$C_{1-8}$alkyl, $C_{2-6}$alkenyl, $C_{2-6}$alkynyl, $C_{6-14}$aryl$C_{2-6}$alkenyl or $C_{6-14}$aryl$C_{2-6}$alkynyl); or —$SR^{11}$ (where $R^{11}$ is hydrogen, $C_{1-8}$alkyl, $C_{6-14}$aryl, or $C_{6-14}$aryl$C_{1-8}$alkyl);

$R^4$, $R^5$, $R^6$, and $R^7$, which are the same or different, are each independently selected from hydrogen; a halo atom; cyano; nitro; $C_{6-14}$aryl; $C_{6-14}$aryl$C_{1-8}$alkyl; —$NR^8R^9$ (where $R^8$ and $R^9$ are the same or different and are hydrogen, $C_{1-8}$alkyl, cyano$C_{1-8}$alkyl, hydroxy$C_{1-8}$alkyl, halo$C_{1-8}$alkyl, $C_{3-7}$cycloalkyl, $C_{1-8}$alkyl$C_{3-7}$cycloalkyl, $C_{2-6}$alkenyl, $C_{3-7}$cycloalkyl$C_{1-8}$alkyl, $C_{2-6}$alkynyl, $C_{6-14}$aryl, $C_{6-14}$aryl$C_{1-8}$alkyl, heterocycle$C_{1-8}$alkyl, $C_{1-8}$alkylcarbonyl, $C_{6-14}$arylsulfonyl, $C_{1-8}$alkysulfonyl, or $R^8R^9$ together with the N atom to which they are attached form a 3,4,5 or 6 membered heterocyclic ring); —$OR^{10}$ (where $R^{10}$ is hydrogen, $C_{1-8}$alkyl, $C_{6-14}$aryl, $C_{6-14}$aryl$C_{1-8}$alkyl, $C_{2-6}$alkenyl, $C_{2-6}$alkynyl, $C_{6-14}$aryl $C_{2-6}$alkenyl or $C_{6-14}$aryl$C_{2-6}$alkynyl); —$SR^{12}$ (where $R^{12}$ is hydrogen, $C_{1-8}$alkyl, $C_{6-14}$aryl, or $C_{6-14}$aryl$C_{1-}$ salkyl); trifluoromethyl; —S(O)$_2$R$^{13}$ (where R$^{13}$ is hydrogen, C$_{1-8}$alkyl, C$_{6-14}$aryl, or C$_{6-14}$arylC$_{1-8}$alkyl); C(O)NR$^{14}$R$^{15}$ (where R$^{14}$ and R$^{15}$ are the same or different and are hydrogen, C$_{1-8}$alkyl, C$_{6-14}$aryl, or C$_{6-14}$arylC$_{1-8}$alkyl); heterocycle or heterocycleC$_{1-8}$alkyl;

provided that when R$^5$ and R$^6$ are Cl, R$^4$ and R$^7$ are hydrogen and R$^3$ is Cl or Br; then R$^1$ and R$^2$ are not hydroxy or O-acetyl;

or a pharmaceutically acceptable derivative thereof.

2. A compound of formula (Ia)

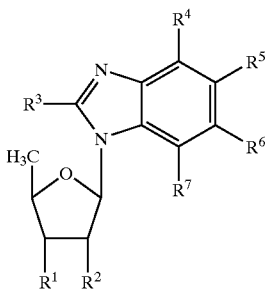

(Ia)

wherein:
R$^1$ is hydroxy or O-acetyl;
R$^2$ is hydroxy, O-acetyl, or a fluorine atom;
R$^3$ is a halo atom or —NR$^8$R$^9$ (wherein R$^8$ and R$^9$ are as hereinbefore defined).
R$^4$ is hydrogen, a halo atom, nitrile, trifluoromethyl, or nitro;
R$^5$ and R$^6$ are the same or different and are hydrogen, a halo atom, nitrile, trifluoromethyl, nitro, or —SR$^{12}$ (wherein R$^{12}$ is as hereinbefore defined);
R$^7$ is hydrogen or a halo atom;
provided that when R$^5$ and R$^6$ are Cl, R$^4$ and R$^7$ are hydrogen and R$^3$ is Cl or Br; then R$^1$ and R$^2$ are not hydroxy or O-acetyl;
or a pharmaceutically acceptable derivative thereof.

3. A compound of formula (Ib)

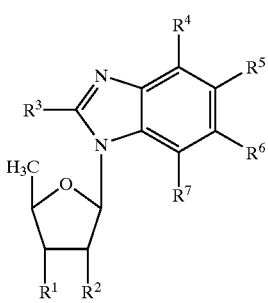

(Ib)

wherein:
R$^1$ is hydroxy or O-acetyl;
R$^2$ is hydroxy, O-acetyl, or a fluorine atom;
R$^3$ is a halo atom, or —NR$^8$R$^9$, wherein R$^8$ is hydrogen and R$^9$ is a C$_{1-6}$ alkyl, or C$_{3-7}$cycloalkyl;
R$^4$ is hydrogen or a halo atom;
R$^5$ and R$^6$ may be the same or different and are hydrogen, a halo atom, nitro, nitrile, trifluoromethyl or —SR$^{12}$ wherein R$^{12}$ is C$_{1-6}$alkyl;
R$^7$ is hydrogen or fluorine;

provided that when R$^5$ and R$^6$ are Cl, R$^4$ and R$^7$ are hydrogen and R$^3$ is Cl or Br; then R$^1$ and R$^2$ are not hydroxy or O-acetyl;

or a pharmaceutically acceptable derivative thereof.

4. A compound of formula (Ic)

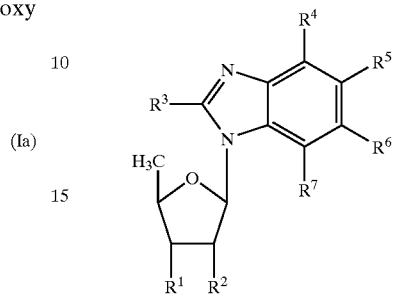

(Ic)

wherein:
R$^1$ is hydroxy;
R$^2$ is hydroxy, or a fluorine atom;
R$^3$ is a halo atom, or —NR$^8$R$^9$, wherein R$^8$ is hydrogen and R$^9$ is a C$_{1-6}$alkyl, or C$_{3-7}$cycloalkyl;
R$^4$ is hydrogen or a halo atom;
R$^5$ and R$^6$ are the same or different and are hydrogen, a halo atom, nitro, nitrile, trifluoromethyl, CH$_3$, or —SR$^{12}$ wherein R$^{12}$ is C$_{1-6}$alkyl;
R$^7$ is hydrogen or fluorine;
provided that when R$^5$ and R$^6$ are Cl, R$^4$ and R$^7$ are hydrogen and R$^3$ is Cl or Br; then R$^1$ and R$^2$ are not hydroxy or O-acetyl;
or a pharmaceutically acceptable derivative thereof.

5. A compound of formula (Id)

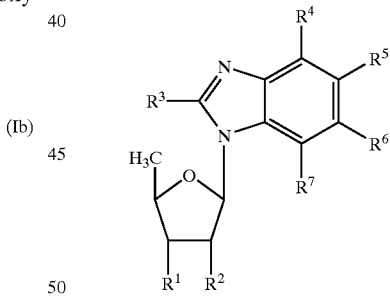

(Id)

R$^1$ is hydroxy;
R$^2$ is hydroxy, or a fluorine atom;
R$^3$ is a halo atom, or —NR$^8$R$^9$, wherein R$^8$ is hydrogen and R$^9$ is a C$_{1-6}$ alkyl, or C$_{3-7}$cycloalkyl;
R$^4$ is hydrogen or a halo atom;
R$^5$ and R$^6$ are the same or different and are hydrogen, a halo atom, nitro, nitrile, trifluoromethyl, CH$_3$, or —SR$^{12}$ wherein R$^{12}$ is C$_{1-6}$alkyl;
R$^7$ is hydrogen or fluorine;
provided that R$^1$ and R$^2$ are cis to each other; and further provided that when R$^5$ and R$^6$ are Cl, R$^4$ and R$^7$ are hydrogen and R$^3$ is Cl or Br; then R$^1$ and R$^2$ are not hydroxy or O-acetyl;
or a pharmaceutically acceptable derivative thereof.

6. A compound of formula (Ie)

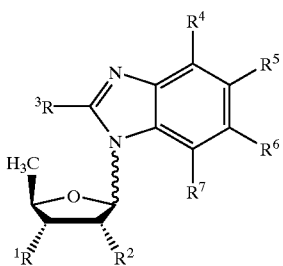

wherein:
R$^1$ is hydroxy; O-acetyl; or a halo atom;
R$^2$ is hydroxy; O-acetyl; or a halo atom;
R$^3$ is hydrogen; a halo atom; azido; C$_{2-6}$alkenyl; C$_{2-6}$alkynyl; aryl C$_{2-6}$alkenyl; C$_{6-14}$aryl C$_{2-6}$alkynyl; —NR$^8$R$^9$ (where R$^8$ and R$^9$ are the same or different and are hydrogen, C$_{1-8}$alkyl, cyanoC$_{1-8}$alkyl, hydroxyC$_{1-8}$alkyl, haloC$_{1-8}$alkyl, C$_{3-7}$cycloalkyl, C$_{1-8}$alkylC$_{3-7}$cycloalkyl, C$_{2-6}$alkenyl, C$_{3-7}$cycloalkylC$_{1-8}$alkyl, C$_{2-6}$alkynyl, C$_{6-14}$aryl, C$_{6-14}$arylC$_{1-8}$alkyl, heterocycleC$_{1-8}$alkyl,C$_{1-8}$alkylcarbonyl, C$_{6-14}$arylsulfonyl, C$_{1-8}$alkylsulfonyl, or R$^8$R$^9$ together with the N atom to which they are attached form a 3,4,5 or 6 membered heterocyclic ring); —OR$^{10}$ (where R$^{10}$ is hydrogen, C$_{1-8}$alkyl, C$_{6-14}$aryl, or C$_{6-14}$arylC$_{1-8}$alkyl, C$_{2-6}$alkenyl, C$_{2-6}$alkynyl, C$_{6-14}$aryl C$_{2-6}$alkenyl or C$_{6-14}$aryl C$_{2-6}$alkynyl); or —SR$^{11}$ (where R$^{11}$ is hydrogen, C$_{1-8}$alkyl, C$_{6-14}$aryl, or C$_{6-14}$arylC$_{1-8}$alkyl);
R$^4$, R$^5$, R$^6$, and R$^7$, which are the same or different, are each independently selected from hydrogen; a halo atom; cyano; nitro; C$_{6-14}$aryl; C$_{6-14}$arylC$_{1-8}$alkyl; —NR$^8$R$^9$ (where R$^8$ and R$^9$ are the same or different and are hydrogen, C$_{1-8}$alkyl, cyanoC$_{1-8}$alkyl, hydroxyC$_{1-8}$alkyl, haloC$_{1-8}$alkyl, C$_{3-7}$cycloalkyl, C$_{1-8}$alkylC$_{3-7}$cycloalkyl, C$_{2-6}$alkenyl, C$_{3-7}$cycloalkylC$_{1-8}$alkyl, C$_{2-6}$alkynyl, C$_{6-14}$aryl, C$_{6-14}$arylC$_{1-8}$alkyl, heterocycleC$_{1-8}$alkyl, C$_{1-8}$alkylcarbonyl, C$_{6-14}$arylsulfonyl, C$_{1-8}$alkylsulfonyl, or R$^8$R$^9$ together with the N atom to which they are attached form a 3,4,5 or 6 membered heterocyclic ring); —OR$^{10}$ (where R$^{10}$ is hydrogen, C$_{1-8}$alkyl, C$_{6-14}$aryl, C$_{6-14}$arylC$_{1-8}$alkyl, C$_{2-6}$alkenyl, C$_{2-6}$alkynyl, C$_{6-14}$aryl C$_{2-6}$alkenyl or C$_{6-14}$arylC$_{2-6}$alkynyl); —SR$^{12}$ (where R$^{12}$ is hydrogen, C$_{1-8}$alkyl, C$_{6-14}$aryl, or C$_{6-14}$arylC$_{1-8}$alkyl); trifluoromethyl; —S(O)$_2$R$^{13}$ (where R$^{13}$ is hydrogen, C$_{1-8}$alkyl, C$_{6-14}$aryl, or C$_{6-14}$arylC$_{1-8}$alkyl); —C(O)NR$^{14}$R$^{15}$ (where R$^{14}$ and R$^{15}$ are the same or different and are hydrogen, C$_{1-8}$alkyl, C$_{6-14}$aryl, or C$_{6-14}$arylC$_{1-8}$alkyl); heterocycle; or heterocycle C$_{1-8}$alkyl.
provided that when R$^5$ and R$^6$ are Cl, R$^4$ and R$^7$ are H and R$^3$ is Cl or Br; then R$^1$ and R$^2$ are not hydroxy or O-acetyl;
or a pharmaceutically acceptable derivative thereof.

7. A compound selected from
5,6-Dichloro-1-(5-deoxy-beta-D-ribofuranosyl)-N-(cyclopropyl)-1H-benzimidazol-2-amine;
5,6-Dichloro-1-(5-deoxy-beta-D-ribofuranosyl)-N-(1-methylethyl)-1H-benzimidazol-2-amine;
2-Azetidino-5,6-dichloro-1-(5-deoxy-beta-D-ribofuranosyl)-1H-benzimidazole;
5,6-Dichloro-1-(5-deoxy-beta-D-ribofuranosyl)-N-(cyclopentyl)-1H-benzimidazol-2-amine;
5,6-Dichloro-1-(5-deoxy-beta-D-ribofuranosyl)-O-(isopropyl)-1H-benzimidazol-2-one;
5,6-Dichloro-1-(5-deoxy-beta-D-ribofuranosyl)-N-(n-hexyl)-1H-benzimidazol-2-amine;
5,6-Dichloro-1-(5-deoxy-beta-D-ribofuranosyl)-N-((R)-sec-butyl)-1H-benzimidazol-2-amine;
5,6-Dichloro-1-(5-deoxy-beta-D-ribofuranosyl)-N-((S)-sec-butyl)-1H-benzimidazol-2-amine;
6-Trifluoromethyl-1-(5-deoxy-beta-D-ribofuranosyl)-N-(1-methylethyl)-1H-benzimidazol-2-amine;
2-Bromo-6-trifluoromethyl-1-(5-deoxy-beta-D-ribofuranosyl)-1H-benzimidazole;
5-Nitro-1-(5-deoxy-beta-D-ribofuranosyl)-N-(1-methylethyl)-1H-benzimidazol-2-amine;
6-Nitro-1-(5deoxy-beta-D-ribofuranosyl)-N-(1-methylethyl)-1H-benzimidazol-2-amine;
5-Chloro-6-trifluoromethyl-1-(5-deoxy-beta-D-ribofuranosyl)-N-(1-methylethyl)-1H-benzimidazol-2-amine;
6-Chloro-5-trifluoromethyl-1-(5-deoxy-beta-D-ribofuranosyl)-N-(1-methylethyl)-1H-benzimidazol-2-amine;
2-Bromo-6-chloro-1-(5-deoxy-beta-D-ribofuranosyl)-1H-benzimidazole;
2-Bromo-5-chloro-1-(5-deoxy-beta-D-ribofuranosyl)-1H-benzimidazole;
6-Chloro-4,5difluoro-1-(5-deoxy-beta-D-ribofuranosyl)-N-(1-methylethyl)-1H-benzimidazol-2-amine;
4,5,6-Trifluoro-1-(5-deoxy-beta-D-ribofuranosyl)-N-(1-methylethyl)-1H-benzimidazol-2-amine;
5-Chloro-6-methylthio-1-(5-deoxy-beta-D-ribofuranosyl)-N-(1-methylethyl)-1H-benzimidazol-2-amine;
5,6,-Dichloro-4-fluoro-1-(5-deoxy-beta-D-ribofuranosyl)-N-(1-methylethyl)-1H-benzimidazol-2-amine;
5,6-Dichloro-7-fluoro-1-(5-deoxy-beta-D-ribofuranosyl)-N-(1-methylethyl)-1H-benzimidazol-2-amine; and
2,5,6-trichloro-1-(5-deoxy-α-D-lyxofuranosyl) benzimidazole.

8. A pharmaceutical formulation comprising a compound of formula (I) as defined in claim 1 or a pharmaceutically acceptable derivative thereof, together with a pharmaceutically acceptable carrier therefor.

9. A method of treatment or prevention of the symptoms or effects of a herpes virus infection in an infected animal which comprises treating said animal with a therapeutically effective amount of a compound as defined according to claim 1.

10. A method according to claim 9 wherein the herpes virus infection is selected from the group consisting of herpes simplex virus 1, herpes simplex virus 2, varicella zoster virus, cytomegalovirus, Epstein Barr virus, human herpes virus 6 and human herpes virus 7 infections.

* * * * *

UNITED STATES PATENT AND TRADEMARK OFFICE
CERTIFICATE OF CORRECTION

PATENT NO. : 6,413,938 B1
DATED : July 2, 2002
INVENTOR(S) : Tidwell et al.

It is certified that error appears in the above-identified patent and that said Letters Patent is hereby corrected as shown below:

Column 60,
Line 40, delete "hydroxyC$_{1-8}$ alkyl, haloC$_{1-8}$alkyl, C$_{3-7}$cycloalky"
and insert -- hydroxyC$_{1-8}$ alkyl, haloC$_{1-8}$alkyl, C$_{3-7}$cycloalky --;

Column 64,
Line 33, delete "6-Chloro-4,5difluoro-1-(5-deoxy-beta-D-ribofuranosyl)-N-"
and insert -- 6-Chloro-4,5-difluoro-1-(5-deoxy-beta-D-ribofuranosyl)-N- --;
Line 48, delete "cally acceptable carrier therefor." and insert -- cally acceptable carrier therefore. --

Signed and Sealed this

Third Day of December, 2002

JAMES E. ROGAN
*Director of the United States Patent and Trademark Office*